United States Patent
Frenkel et al.

(10) Patent No.: US 10,720,230 B2
(45) Date of Patent: *Jul. 21, 2020

(54) METHOD FOR ADMINISTERING A CHECKPOINT BLOCKADE THERAPY TO A SUBJECT

(71) Applicant: BostonGene Corporation, Lincoln, MA (US)

(72) Inventors: Feliks Frenkel, Moscow (RU); Nikita Kotlov, Moscow (RU); Alexander Bagaev, Moscow (RU); Maksym Artomov, Kirkwood, MO (US); Ravshan Ataullakhanov, Moscow (RU)

(73) Assignee: BostonGene Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/006,129

(22) Filed: Jun. 12, 2018

(65) Prior Publication Data

US 2018/0357362 A1 Dec. 13, 2018
US 2019/0179998 A9 Jun. 13, 2019

Related U.S. Application Data

(60) Provisional application No. 62/598,440, filed on Dec. 13, 2017, provisional application No. 62/518,787, filed on Jun. 13, 2017.

(51) Int. Cl.

| | | |
|---|---|---|
| G16B 45/00 | (2019.01) | |
| G16H 50/30 | (2018.01) | |
| C12Q 1/6886 | (2018.01) | |
| G16H 50/20 | (2018.01) | |
| G16H 50/70 | (2018.01) | |
| G06F 16/28 | (2019.01) | |
| G16B 5/00 | (2019.01) | |
| G16B 20/00 | (2019.01) | |
| G16B 40/00 | (2019.01) | |
| G16B 50/00 | (2019.01) | |
| G16B 5/20 | (2019.01) | |
| G06F 17/18 | (2006.01) | |
| G16H 20/00 | (2018.01) | |
| G16H 50/50 | (2018.01) | |
| G16H 20/10 | (2018.01) | |
| G16H 20/40 | (2018.01) | |
| G16H 70/20 | (2018.01) | |
| G16H 10/20 | (2018.01) | |

(52) U.S. Cl.
CPC .......... *G16B 45/00* (2019.02); *C12Q 1/6886* (2013.01); *G06F 16/285* (2019.01); *G06F 17/18* (2013.01); *G16B 5/00* (2019.02); *G16B 5/20* (2019.02); *G16B 20/00* (2019.02); *G16B 40/00* (2019.02); *G16B 50/00* (2019.02); *G16H 10/20* (2018.01); *G16H 20/00* (2018.01); *G16H 20/10* (2018.01); *G16H 20/40* (2018.01); *G16H 50/20* (2018.01); *G16H 50/30* (2018.01); *G16H 50/50* (2018.01); *G16H 50/70* (2018.01); *G16H 70/20* (2018.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2006/0127928 A1 | 6/2006 | Bacus et al. |
| 2007/0172844 A1 | 7/2007 | Lancaster et al. |
| 2008/0153098 A1 | 6/2008 | Rimm et al. |
| 2009/0105167 A1 | 4/2009 | Potti et al. |
| 2012/0220580 A1 | 8/2012 | Li et al. |

(Continued)

FOREIGN PATENT DOCUMENTS

| | | |
|---|---|---|
| WO | WO 2015/073896 A2 | 5/2015 |
| WO | WO 2017/013436 A1 | 1/2017 |
| WO | WO 2017/093764 A1 | 6/2017 |

OTHER PUBLICATIONS

International Search Report and Written Opinion for International Application No. PCT/US2018/037008 dated Sep. 21, 2018.

(Continued)

*Primary Examiner* — Pablo S Whaley
(74) *Attorney, Agent, or Firm* — Wolf, Greenfield & Sacks, P.C.

(57) ABSTRACT

Techniques for determining whether a subject is likely to respond to an immune checkpoint blockade therapy. The techniques include obtaining expression data for the subject, using the expression data to determine subject expression levels for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether the subject is likely to respond to the immune checkpoint blockade therapy.

9 Claims, 28 Drawing Sheets

(56) References Cited

U.S. PATENT DOCUMENTS

| | | | |
|---|---|---|---|
| 2014/0342924 A1 | 11/2014 | Harkin et al. | |
| 2016/0123964 A1 | 5/2016 | Tumeh et al. | |
| 2016/0312286 A1 | 10/2016 | Brandon et al. | |

OTHER PUBLICATIONS

International Search Report and Written Opinion for International Application No. PCT/US2018/037018 dated Sep. 21, 2018.
International Search Report and Written Opinion for International Application No. PCT/US2018/037017 dated Sep. 25, 2018.
Bao et al., AbsCN-seq: a statistical method to estimate tumor purity, ploidy and absolute copy numbers from next-generation sequencing data. Bioinformatics. 2014;30(8):1056-063.
Beck et al., Significance Analysis of Prognostic Signatures. PLOS Computational Biology. 2013;9(1):1-17.
Burke, Predicting Clinical Outcomes Using Molecular Biomarkers. Biomarkers in Cancer. 2016;8:89-99.
Ding, Visualization and Integrative Analysis of Cancer Multi-Omics Data. Dissertation. The Ohio State University. 2016. 150 pages.
Feng et al., Differentially expressed genes between primary cancer and paired lymph node metastases predict clinical outcome of node-positive breast cancer patients. Breast Cancer Research and Treatment. 2007;103:319-29.
Finak et al., Stromal gene expression predicts clinical outcome in breast cancer. Nature Medicine. 2008;14:518-527.
Gyorffy et al., An online survival analysis tool to rapidly assess the effect of 22,277 genes on breast cancer prognosis using microarray date of 1,809 patients. Breast Cancer Research and Treatment. 2010;123:725-31.
Hermann et al., Analysis and Visualization of Gene Expression Data. Dissertation. Tubingen. 2011. 180 pages.
Jansen et al., Molecular Classification of Tamoxifen-Resistant Breast Carcinomas by Gene Expression Profiling. Journal of Clinical Oncology. 2005;23(4):732-40.
Mcart et al., PICan: An integromics framework for dynamic cancer biomarker discovery. Molecular Oncology. 2015;9(6):1234-40.
Merico et al., Enrichment Map: A Network-Based Method for Gene-Set Enrichment Visualization and Interpretation. Plos One. 2010;5(11):1-12.
Mustacchi et al., Identification and Validation of a New Set of Five Genes for Prediction of Risk in Early Breast Cancer. International Journal of Molecular Science. 2013;14:9686-702.
Nam et al., A pathway-based approach for identifying biomarkers of tumor progression to trastuzumab-resistant breast cancer. Cancer Letters. 2015;356:880-90.
Panse et al., Chemokine CXCLI3 is overexpressed in the tumor tissue and in the peripheral blood of breast cancer patients. British Journal of Cancer. 2008;99:930-38.
Pardoll, The blockade of immune checkpoints in cancer immunotherapy. Nature Reviews Cancer. 2012;12(4):252-64.
Sturm et al., Discovering Medical Knowledge Using Visual Analytics. Eurographics Workshop on Visual Computing for Biology and Medicine. 2015. 10 pages.
Tamburini et al., Gene expression profiling identifies inflammation and angiogenesis as distinguishing features of canine hemangiosarcoma. BMC Cancer. 2010;10(1):619. 16 pages.
Van Der Auwera et al., Increased Angiogenesis and Lymphangiogenesis in Inflammatory versus Noninflammatory Breast Cancer by Real-Time Reverse Transcriptase-PCR Gene Expression Quantification. Clinical Cancer Research. 2004;10:7965-971.
Vuaroqueaux et al. Low E2F1 transcript levels are a strong determinant of favorable breast cancer outcome. Breast Cancer Research 2007. 2007;9:1-10.
West et al., Tumor-infiltrating lymphocytes predict response to anthracycline-based chemotherapy in estrogen receptor-negative breast cancer. Breast Cancer Research. 2011;12:13 pages.

[No Author Listed] Atezolizumab (Tecentriq). FDA U.S. Food & Drug Administration. https://www.fda.gov/drugs/informationondrugs/approveddrugs/ucm525780.htm Last updated Oct. 19, 2016. Last accessed Jul. 26, 2018. 2 pages.
[No Author Listed] Bevacizumab. FDA U.S. Food & Drug Administration. https://web.archive.org/web/20170111231723/https://www.fda.gov/Drugs/InformationOnDrugs/ApprovedDrugs/ucm336763.htm Last updated Oct. 9, 2015. Last accessed via WayBackMachine Jul. 26, 2018. 1 page.
[No Author Listed] Elotuzumab. FDA U.S. Food & Drug Administration. https://web.archive.org/web/20170118085702/http://www.fda.gov/Drugs/InformationOnDrugs/ApprovedDrugs/ucm474719.htm Last updated Nov. 30, 2015. Last accessed via WayBackMachine Jul. 26, 2018. 1 page.
[No Author Listed] Nivolumab (Opdivo). FDA U.S. Food & Drug Administration. https://web.archive.org/web/20170118085700/https://www.fda.gov/Drugs/InformationOnDrugs/ApprovedDrugs/ucm436566.htm Last updated Apr. 6, 2015. Last accessed via WayBackMachine Jul. 26, 2018. 1 page.
[No Author Listed] Olaratumab (Lartruvo). FDA U.S. Food & Drug Administration. https://www.fda.gov/Drugs/InformationOnDrugs/ApprovedDrugs/ucm526087.htm Last updated Oct. 20, 2016. Last accessed Jul. 26, 2018. 2 pages.
[No Author Listed] Osimertinib. FDA U.S. Food & Drug Administration. https://web.archive.org/web/20170227152135/https://www.fda.gov/Drugs/InformationOnDrugs/ApprovedDrugs/ucm472565.htm Last updated Nov. 13, 2015. Last accessed via WayBackMachine Jul. 26, 2018. 1 page.
[No Author Listed] Pembrolizumab (Keytruda) Checkpoint Inhibitor. FDA U.S. Food & Drug Administration. https://www.fda.gov/Drugs/InformationOnDrugs/ApprovedDrugs/ucm526430.htm Last updated Oct. 25, 2016. Last accessed Jul. 26, 2018. 2 pages.
[No Author Listed] Rituximab Infusion. FDA U.S. Food & Drug Administration. https://web.archive.org/web/20161211125252/http://www.fda.gov:80/Drugs/InformationOnDrugs/ApprovedDrugs/ucm324890.htm Last updated May 4, 2016. Last accessed via WayBackMachine Jul. 26, 2018. 1 page.
[No Author Listed], A Phase 3 Study of Pembrolizumab + Epacadostat or Placebo in Subjects With Unresectable or Metastatic Melanoma (Keynote-252 / ECHO-301). Clinical Trials. https://clinicaltrials.gov/ct2/show/NCT02752074 Last updated May 8, 2018. Last accessed Jul. 26, 2018. 7 pages.
[No Author Listed], A Pilot Study to Evaluate the Safety of a 3 Weeks Sitagliptin Treatment in HCC Patients Undergoing Liver Resection (HCC-DPPIV). Clinical Trials. https://clinicaltrials.gov/ct2/show/NCT02650427 Last updated Sep. 28, 2017. Last accessed Jul. 26, 2018. 7 pages.
[No Author Listed], Combination of Interferon-gamma and Nivolumab for Advanced Solid Tumors. Clinical Trials. https://clinicaltrials.gov/ct2/show/NCT02614456 Last updated Feb. 7, 2018. Last accessed Jul. 26, 2018. 8 pages.
[No Author Listed], Evaluation of MGN1703 Maintenance Treatment in Patients with mCRC With Tumor Reduction During Induction Treatment (IMPALA). Clinical Trials. https://clinicaltrials.gov/ct2/show/NCT02077868 Last updated Jun. 23, 2017. Last accessed Jul. 26, 2018. 7 pages.
[No Author Listed], FDA Approves Merck's KEYTRUDA® (pembrolizumab) as First-Line Combination Therapy with Pemetrexed and Carboplatin for Patients with Metastatic Nonsquamous Non-Small Cell Lung Cancer (NSCLC), Irrespective of PD-L1 Expression. Merck. http://investors.merck.com/news/press-release-details/2017/FDA-Approves-Mercks-KEYTRUDA-pembrolizumab-as-First-Line-Combination-Therapy-with-Pemetrexed-and-Carboplatin-for-Patients-with-Metastatic-Nonsquamous-Non-Small-Cell-Lung-Cancer-NSCLC-Irrespective-of-PD-L1-Expression/default.aspx May 10, 2017. Last accessed Jul. 27, 2018. 10 pages.
[No Author Listed], FDA grants accelerated approval to pembrolizumab for first tissue/site agnostic indication. FDA U.S. Food & Drug Administration. https://www.fda.gov/drugs/informationondrugs/approveddrugs/ucm560040.htm Last updated May 30, 2017. Last accessed Jul. 27, 2018. 2 pages.
[No Author Listed], Immunotherapy Combination Study in Advanced Previously Treated Non-Small Cell Lung Cancer. Clinical Trials.

(56) References Cited

OTHER PUBLICATIONS https://clinicaltrials.gov/ct2/show/NCT02460367 Last updated Feb. 4, 2016. Last accessed Jul. 26, 2018. 9 pages.

[No Author Listed], L-NMMA Plus Docetaxel in Refractory Locally Advanced or Metastatic Triple Negative Breast Cancer Patients. Clinical Trials. https://clinicaltrials.gov/ct2/show/NCT02834403 Last updated Mar. 29, 2018. Last accessed Jul. 26, 2018. 10 pages.

[No Author Listed], NHS-IL12 for Solid Tumors. Clinical Trials. https://clinicaltrials.gov/ct2/show/NCT01417546 Last updated Jul. 6, 2018. Last accessed Jul. 26, 2018. 11 pages.

[No Author Listed], Ph2 NK Cell Enriched DCIs w/wo RLR9 Agonist, DUK-CPG-001 From Donors Following Allogeneic Sct (NK-DCI). Clinical Trials. https://clinicaltrials.gov/ct2/show/NCT02452697 Last updated Jul. 25, 2018. Last accessed Jul. 26, 2018. 10 pages.

[No Author Listed], Provenge Followed by Docetaxel in Castration-Resistant Prostate Cancer. Clinical Trials. https://clinicaltrials.gov/ct2/show/NCT02793219 Last updated Oct. 30, 2017. Last accessed Jul. 26, 2018. 11 pages.

[No Author Listed], SABR-ATAC: A Trial of TGF-beta Inhibition and Stereotactic Ablative Radiotherapy for Early Stage Non-small Cell Lung Cancer. Clinical Trials. https://clinicaltrials.gov/ct2/show/NCT02581787 Last updated May 7 4, 2018. Last accessed Jul. 26, 2018. 8 pages.

[No Author Listed], Study Evaluating the Safety and Pharmacokinetics of JCAR017 in B-cell Non-Hodgkin Lymphoma (TRANSCEND-NHL-001). Clinical Trials. https://clinicaltrials.gov/ct2/show/NCT02631044 Last updated Jun. 8, 2018. Last accessed Jul. 26, 2018. 12 pages.

[No Author Listed], Study of AM0010 With Folfox Compared to Folfox Alone Second-line Tx in Pts With Metastatic Pancreatic Cancer (Sequoia). Clinical Trials. https://clinicaltrials.gov/ct2/show/NCT02923921 Last updated Jul. 17, 2018. Last accessed Jul. 26, 2018. 6 pages.

[No Author Listed], The R Project for Statistical Computing. Getting Started. https://www.r-project.org/ last accessed Jul. 26, 2018. 5 pages.

[No Author Listed], Trial of TRX518 (Anti-GITR mAb) in Stage III or IV Malignant Melanoma or Other Solid Tumors (TRX518-001). Clinical Trials. https://clinicaltrials.gov/ct2/show/NCT01239134 Last updated Mar. 3, 2017. Last accessed Jul. 26, 2018. 9 pages.

Akbani et al., Genomic Classification of Cutaneous Melanoma. Cell. Jun. 18, 2015;161(7):1681-96. doi: 10.1016/j.cell.2015.05.044.

Aran et al., Systematic pan-cancer analysis of tumour purity. Nat Commun. Dec. 4, 2015;6:8971. doi: 10.1038/ncomms9971. 11 pages.

Ayers et al., Relationship between immune gene signatures and clinical response to PD-1 blockade with pembrolizumab (MK-3475) in patients with advanced solid tumors. Journal for Immuno Therapy of Cancer. 2015;3(22):1-2.

Barbie et al., Systematic RNA interference reveals that oncogenic KRAS-driven cancers require TBK1. Nature. 2009. 462. 108-12.

Becht et al., Estimating the population abundance of tissue-infiltrating immune and stromal cell populations using gene expression. Genome Biol. Oct. 20, 2016;17(1):218.

Blank et al., The "cancer immunogram" Science. 2016;352:658-60.

Blondel et al., Fast unfolding of communities in large networks. J Stat Mech Theory Exp. 2008. P10008. 12 pages.

Bolotin et al., Antigen receptor repertoire profiling from RNA-seq data. Nat Biotechnol. Oct. 11, 2017;35(10):908-911. doi: 10.1038/nbt.3979.

Bray et al. Near-optimal probabilistic RNA-seq quantification. Nature Biotechnology vol. 34, pp. 525-527 (2016).

Brown et al., Regression of Glioblastoma after Chimeric Antigen Receptor T-Cell Therapy. The New England Journal of Medicine. 2016. 9 pages.

Cantoni et al., NK Cells, Tumor Cell Transition, and Tumor Progression in Solid Malignancies: New Hints for NK-Based Immunotherapy. Journal of Immunology Research. 2016. 13 pages.

Carter et al., Absolute quantification of somatic DNA alterations in human cancer. Nat Biotechnol. May 2012; 30(5): 413-421.

Chanmee et al., Tumor-associated macrophages as major players in the tumor microenvironment. Cancers (Basel). Aug. 13, 2014;6(3):1670-90. doi: 10.3390/cancers6031670.

Charoentong et al., Pan-cancer Immunogenomic Analyses Reveal Genotype-Immunophenotye Relationships and Predictors of Response to Checkpoint Blockade. Cell Rep. Cold Spring Harbor Labs Journals. 2017;18:248-62.

Chaudhary et al., Regulatory T Cells in the Tumor Microenvironment and Cancer Progression: Role and Therapeutic Targeting. Vaccines (Basel). Aug. 6, 2016;4(3). pii: E28. doi: 10.3390/vaccines4030028. 25 pages.

Filatenkov et al., Ablative Tumor Radiation Can Change the Tumor Immune Cell Microenvironment to Induce Durable Complete Remissions. Clin Cancer Res. Aug. 15, 2015;21(16):3727-39. doi: 10.1158/1078-0432.CCR-14/2824. Epub Apr. 13, 2015.

Gordon et al., Using gene expression ratios to predict outcome among patients with mesothelioma. J Natl Cancer Inst. Apr. 16, 2003;95(8):598-605.

Grossman et al., Toward a Shared Vision for Cancer Genomic Data. Perspective. Sep. 22, 2016. 4 pages.

Haabeth et al., Inflammation driven by tumour-specific Th1 cells protects against B-cell cancer. Nat Commun. 2011;2:240. doi: 10.1038/ncomms1239. 12 pages.

Hagberg et al., Exploring network structure, dynamics, and function using NetworkX. Proceedings of the 7th Python in Science Conference (SciPy 2008). 5 pages.

Hanzelmann et al., GSVA: gene set variation analysis for microarray and RNA-seq data. BMC Bioinformatics. Jan. 16, 2013;14:7. doi: 10.1186/1471-2105-14-7.

Hua et al., Accumulation of FoxP3+ T regulatory cells in the tumor microenvironment of human colorectal adenomas. Pathol Res Pract. Feb. 2016;212(2):106-12. doi: 10.1016/j.prp.2015.12.002. Epub Dec. 14, 2015.

Hugo et al., Genomic and Transcriptomic Features of Response to Anti-PD-1 Therapy in Metastatic Melanoma. Cell. 2016;165(1):35-44.

Hunter, Matplotlib: A 2D Graphics Environment. Comput Sci Eng. 2007;9:90-5.

Jacquelot et al., Predictors of responses to immune checkpoint blockade in advanced melanoma. Nature Communications. 2017. 13 pages.

Ji et al., An immune-active tumor microenvironment favors clinical response to ipilimumab. Cancer Immunology, Immunotherapy. 2012;61(7):1019-31.

Kandoth et al., Mutational landscape and significance across 12 major cancer types. Nature. Oct. 17, 2013;502(7471):333-339. doi: 10.1038/nature12634.

Kaporis et al., Human basal cell carcinoma is associated with Foxp3+ T cells in a Th2 dominant microenvironment. J Invest Dermatol. Oct. 2007;127(10):2391-8. Epub May 17, 2007.

Kemper et al., BRAF(V600E) Kinase Domain Duplication Identified in Therapy-Refractory Melanoma Patient-Derived Xenografts. Cell Rep. Jun. 28, 2016;16(1):263-277. doi: 10.1016/j.celrep.2016.05.064. Epub Jun. 16, 2016.

Le et al., PD-1 Blockade in Tumors with Mismatch-Repair Deficiency. N Engl J Med. Jun. 25, 2015;372(26):2509-20. doi: 10.1056/NEJMoa1500596. Epub May 30, 2015.

Lu et al., Identification of Gene Expression Biomarkers for Predicting Radiation Exposure. Sci Rep 2015;4(1):6293. 7 pages.

Marvel et al., Myeloid-derived suppressor cells in the tumor microenvironment: expect the unexpected. J Clin Invest. Sep. 2015;125(9):3356-64. doi: 10.1172/JCI80005. Epub Jul. 13, 2015.

McKinney, Data Structures for Statistical Computing in Python. Proc. of the 9th Python in Science Conf. SCIPY 2010;51.

Nathanson et al., Somatic Mutations and Neoepitope Homology in Melanomas Treated with CTLA-4 Blockade. Cancer Immunology Research. 2017. 9 pages.

Newman et al., Robust enumeration of cell subsets from tissue expression profiles. Nat Methods. May 2015;12(5):453-7. doi: 10.1038/nmeth.3337. Epub Mar. 30, 2015.

(56) References Cited

OTHER PUBLICATIONS

Noguera et al., Extracellular matrix, biotensegrity and tumor microenvironment. An update and overview. Histol Histopathol. Jun. 2012;27(6):693-705. doi: 10.14670/HH-27.693.
O'Leary et al., Reference sequence (RefSeq) database at NCBI: current status, taxonomic expansion, and functional annotation. Nucleic Acids Res. Jan. 4, 2016;44(D1):D733-45. doi: 10.1093/nar/gkv1189. Epub Nov. 8, 2015.
Palmieri et al., Genetic instability and increased mutational load: which diagnostic tool best direct patients with cancer to immunotherapy? J Transl Med. 2017; 15: 17. 4 pages.
Papageorgis, TGFβ Signaling in Tumor Initiation, Epithelial-to-Mesenchymal Transition, and Metastasis. J Oncol. 2015;2015:587193. doi: 10.1155/2015/587193. Epub Mar. 25, 2015. 15 pages.
Passiglia et al., PD-L1 expression as predictive biomarker in patients with NSCLC: a pooled analysis. Oncotarget. Apr. 12, 2016;7(15):19738-47. doi: 10.18632/oncotarget.7582.
Pedregosa et al., Scikit-learn: Machine Learning in Python. J Mach Learn Res. 12(Oct):2825-2830, 2011.
Quail et al., Microenvironmental regulation of tumor progression and metastasis. Nat Med. Nov. 2013;19(11):1423-37. doi: 10.1038/nm.3394.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Rizvi et al., Cancer immunology. Mutational landscape determines sensitivity to PD-1 blockade in non-small cell lung cancer. Science. Apr. 3, 2015;348(6230):124-8. doi: 10.1126/science.aaa1348. Epub Mar. 12, 2015.
Roh et al., Integrated molecular analysis of tumor biopsies on sequential CTLA-4 and PD-1 blockade reveals markers of response and resistance. Cancer. Sci Transl Med. 2017. 13 pages.
Sato et al., Integrated molecular analysis of clear-cell renal cell carcinoma. Nat Genet. Aug. 2013;45(8):860-7. doi: 10.1038/ng.2699. Epub Jun. 24, 2013.
Schumacher et al., Editorial overview: Cancer immunology: genomics & biomarkers: Cancer immunity through the prism of genomics and proteomics. Curr Opin Immunol. Aug. 2016;41:ix-x. doi: 10.1016/j.coi.2016.07.006. Epub Aug. 6, 2016.
Senbabaoglu et al., Tumor immune microenvironment characterization in clear cell renal cell carcinoma identifies prognostic and immunotherapeutically relevant messenger RNA signatures. Genome Biol. Nov. 17, 2016;17(1):231. 25 pages.
Shalapour et al., Immunosuppressive plasma cells impede T-cell-dependent immunogenic chemotherapy. Nature. May 7, 2015;521(7550):94-8. doi: 10.1038/nature14395. Epub Apr. 29, 2015.
Shannon et al., Cytoscape: a software environment for integrated models of biomolecular interaction networks. Genome Res. Nov. 2003;13(11):2498-504.
Shiga et al., Cancer-Associated Fibroblasts: Their Characteristics and Their Roles in Tumor Growth. Cancers (Basel). Dec. 11, 2015;7(4):2443-58. doi: 10.3390/cancers7040902.
Singel et al., Neutrophils in the tumor microenvironment: trying to heal the wound that cannot heal. Immunol Rev. Sep. 2016;273(1):329-43. doi: 10.1111/imr.12459.
Snyder et al., Genetic Basis for Clinical Response to CTLA-4 Blockade in Melanoma. N Engl J Med. 2014;371(23):2189-99.
Subramanian et al., Gene set enrichment analysis: a knowledge-based approach for interpreting genome-wide expression profiles. Proc Natl Acad Sci U S A. Oct. 25, 2005;102(43):15545-50. Epub Sep. 30, 2005.
Tappeiner et al., TIminer: NGS data mining pipeline for cancer immunology and immunotherapy. Bioinformatics. Oct. 1, 2017;33(19):3140-3141. doi: 10.1093/bioinformatics/btx377.
Tirosh et al., Dissecting the multicellular ecosystem of metastatic melanoma by single-cell RNA-seq. Science. Apr. 8, 2016;352(6282):189-96. doi: 10.1126/science.aad0501.
Umansky et al., Tumor microenvironment and myeloid-derived suppressor cells. Cancer Microenviron. Aug. 2013;6(2):169-77. doi: 10.1007/s12307-012-0126-7. Epub Dec. 16, 2012.
Van Allen et al., Genomic correlates of response to CTLA-4 blockade in metastatic melanoma. Science. Oct. 9, 2015;350(6257):207-211. doi: 10.1126/science.aad0095. Epub Sep. 10, 2015.
Van Der Maaten, Accelerating t-SNE using Tree-Based Algorithms. Journal of Machine Learning Research. 2014;15:3221-3245.
Van Der Maaten, Visualizing Data using t-SNE. Journal of Machine Learning Research. 2008;9:2579-2605.
Van Der Walt et al., The NumPy Array: A Structure for Efficient Numerical Computation. Computing in Science and Engineering. 2011;13(2):22-30.
Vilgelm et al,. Combinatorial approach to cancer immunotherapy: strength in numbers. JLB. 2016. 16 pages.
Wargo et al., Monitoring immune responses in the tumor microenvironment. Curr Opin Immunol. Aug. 2016;41:23-31. doi: 10.1016/j.coi.2016.05.006. Epub May 27, 2016.
Yu et al., Cancer-associated fibroblasts induce epithelial-mesenchymal transition of breast cancer cells through paracrine TGF-β signalling. Br J Cancer. Feb. 4, 2014;110(3):724-32. doi: 10.1038/bjc.2013.768. Epub Dec. 12, 2013.
Zhang et al., Starved and Asphyxiated: How Can CD8(+) T Cells within a Tumor Microenvironment Prevent Tumor Progression. Front Immunol. Feb. 10, 2016;7:32. doi: 10.3389/fimmu.2016.00032. eCollection 2016.
U.S. Appl. No. 16/006,462, filed Jun. 12, 2018, Bagaev et al.
U.S. Appl. No. 16/006,481, filed Jun. 12, 2018, Bagaev et al.
U.S. Appl. No. 16/006,518, filed Jun. 12, 2018, Bagaev et al.
U.S. Appl. No. 16/006,555, filed Jun. 12, 2018, Bagaev et al.
U.S. Appl. No. 16/006,572, filed Jun. 12, 2018, Bagaev et al.
U.S. Appl. No. 16/006,593, filed Jun. 12, 2018, Bagaev et al.
U.S. Appl. No. 16/006,085, filed Jun. 12, 2018, Frenkel et al.
U.S. Appl. No. 16/006,200, filed Jun. 12, 2018, Bagaev et al.
U.S. Appl. No. 16/006,279, filed Jun. 12, 2018, Bagaev et al.
U.S. Appl. No. 16/006,340, filed Jun. 12, 2018, Bagaev et al.
U.S. Appl. No. 16/006,381, filed Jun. 12, 2018, Bagaev et al.

Hugo
aPD1
28 samples

SKCM17
aCTLA4/aPD1
17 samples

Nathanson
aCTLA4
24 samples

VanAllen
aCTLA4
42 samples

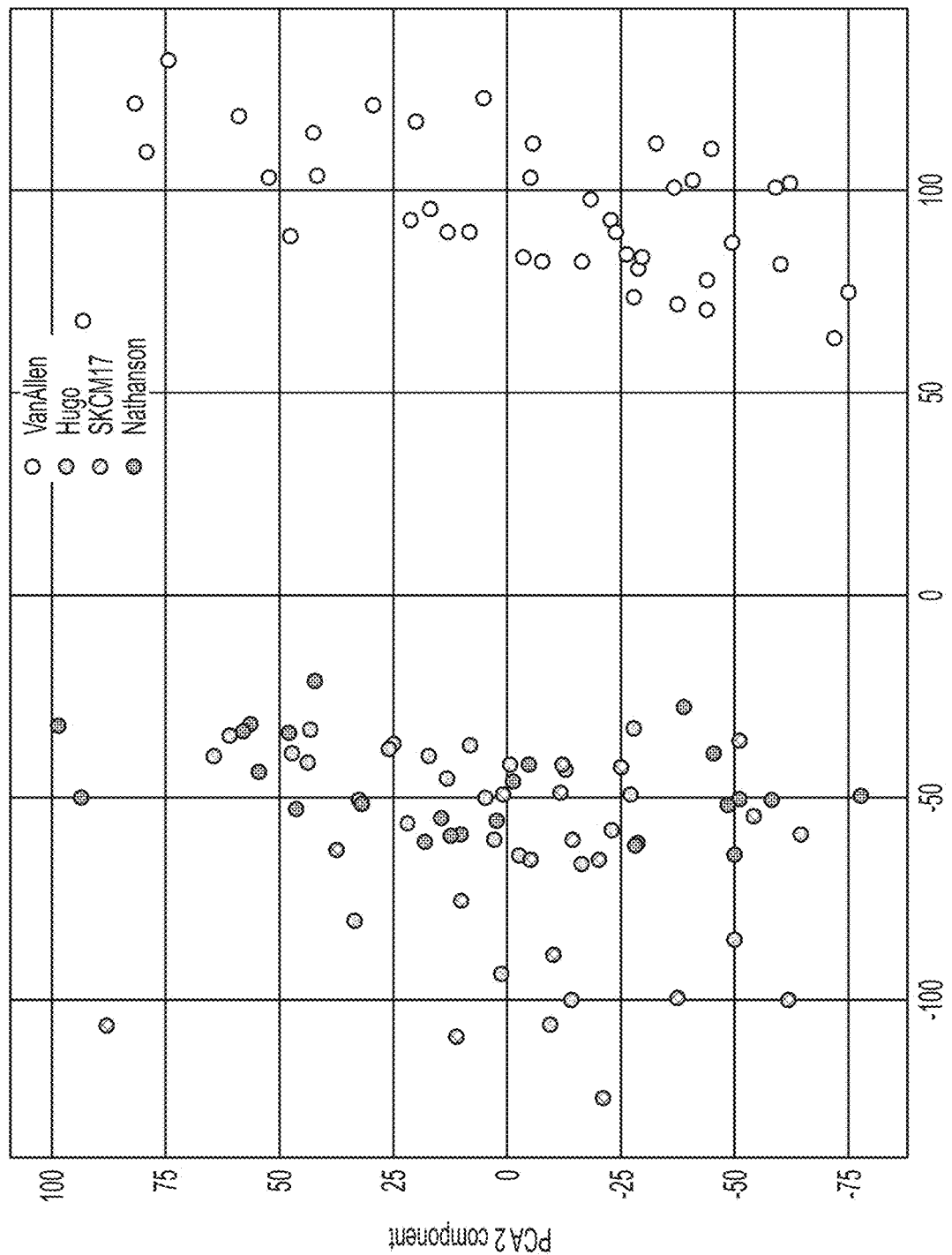

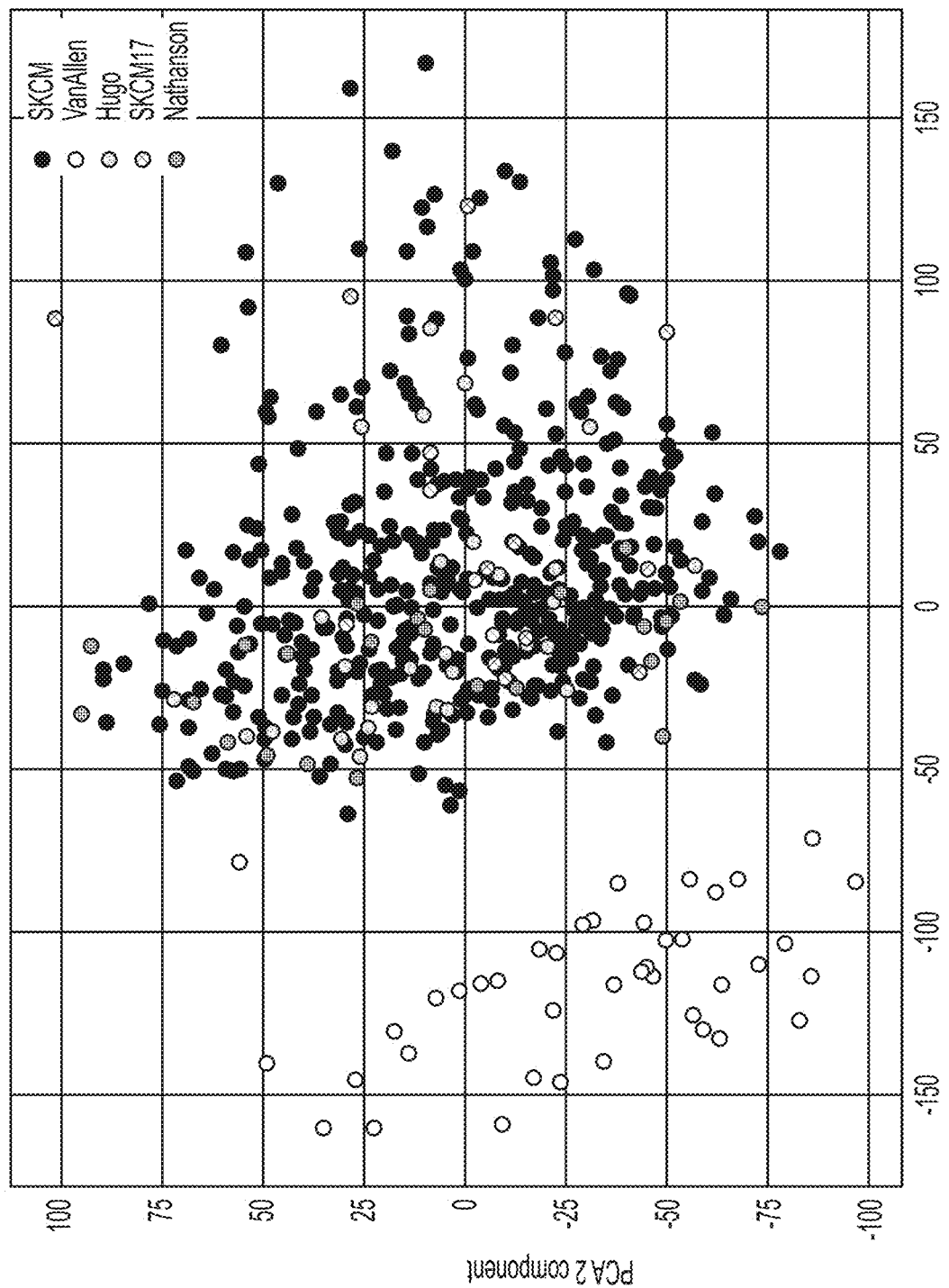

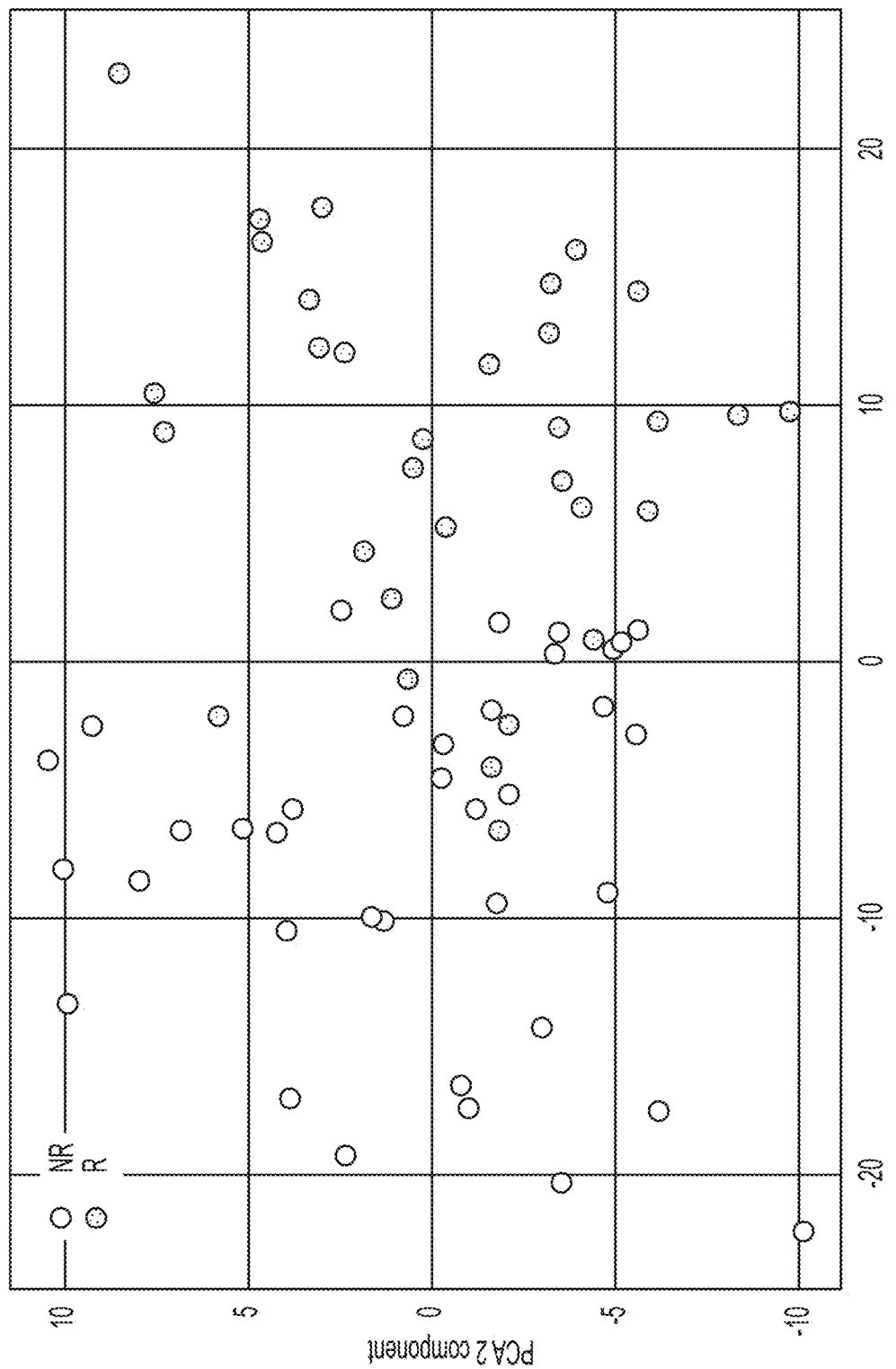

|  | Hugo | | SKCM17 | | Nathanson | |
|---|---|---|---|---|---|---|
|  | FC | pValue | FC | pValue | FC | pValue |
| BRAF/RAI14 | 2.12 | 0.0086 | 2.51 | 0.0013 | 3.48 | 0.0141 |
| ACVR1B/MPRIP | 2.12 | 0.0015 | 2.05 | 0.0131 | 1.84 | 0.0184 |
| ACVR1B/COPS3 | 2.08 | 0.0024 | 1.90 | 0.0402 | 2.21 | 0.0045 |
| PRKAG1/STX2 | 2.75 | 0.0006 | 1.75 | 0.0297 | 2.81 | 0.0184 |
| NLRX1/ELAC2 | 2.01 | 0.0129 | 2.25 | 0.0044 | 2.60 | 0.0081 |
| MON1B/STX2 | 2.59 | 0.0013 | 1.68 | 0.0402 | 2.67 | 0.0184 |
| ARF3/MPRIP | 1.96 | 0.0028 | 1.80 | 0.0184 | 1.98 | 0.0485 |
| ARPIN/MPRIP | 1.54 | 0.0075 | 1.73 | 0.0156 | 1.79 | 0.0033 |
| SPRYD3/FLII | 1.72 | 0.0188 | 2.16 | 0.0044 | 1.94 | 0.0304 |
| TIRAP/MPRIP | 1.53 | 0.0382 | 2.22 | 0.0016 | 1.86 | 0.0485 |
| GSE1/RAI14 | 2.57 | 0.0304 | 2.91 | 0.0217 | 4.71 | 0.0018 |
| POLR3K/HAUS8 | 1.89 | 0.0146 | 2.07 | 0.0064 | 2.26 | 0.0141 |
| RAB40C/HAUS8 | 1.76 | 0.0099 | 2.08 | 0.0053 | 1.91 | 0.0141 |
| PIGO/MPRIP | 1.77 | 0.0304 | 1.74 | 0.0077 | 2.38 | 0.0304 |
| MFHAS1/USP13 | 2.05 | 0.0146 | 2.59 | 0.0184 | 3.87 | 0.0304 |
| GSE1/NPIPA1 | 2.75 | 0.0129 | 2.25 | 0.0466 | 4.35 | 0.0033 |
| DPH6/STX2 | 4.02 | 0.0024 | 1.91 | 0.0466 | 2.14 | 0.0386 |
| ERLIN2/RAI14 | 1.99 | 0.0304 | 2.61 | 0.0184 | 3.49 | 0.0184 |
| CES2/LHFP | 3.00 | 0.0240 | 3.45 | 0.0156 | 2.08 | 0.0386 |
| NAIF1/HAUS8 | 1.99 | 0.0057 | 1.95 | 0.0217 | 2.37 | 0.0108 |

FIG. 4E

METHOD FOR ADMINISTERING A CHECKPOINT BLOCKADE THERAPY TO A SUBJECT

RELATED APPLICATIONS

This application claims the benefit under 35 U.S.C. § 119(e) of the filing date of U.S. provisional patent application Ser. No. 62/518,787, entitled "Systems and Methods for Identifying Cancer Treatments from Sequence Data", filed Jun. 13, 2017 and U.S. provisional patent application Ser. No. 62/598,440, entitled "Systems and Methods Identifying Cancer Treatments from Sequence Data," filed Dec. 13, 2017, the entire contents of each of which are incorporated herein by reference.

This application is filed on the same day as International Application No.: PCT/US18/37017, entitled "SYSTEMS AND METHODS FOR GENERATING, VISUALIZING AND CLASSIFYING MOLECULAR FUNCTIONAL PROFILES"; International Application No.: PCT/US18/37018, entitled "SYSTEMS AND METHODS FOR IDENTIFYING RESPONDERS AND NON-RESPONDERS TO IMMUNE CHECKPOINT BLOCKADE THERAPY"; and International Application No.: PCT/US18/37008, entitled "SYSTEMS AND METHODS FOR IDENTIFYING CANCER TREATMENTS FROM NORMALIZED BIOMARKER SCORES", the entire contents of each of which are incorporated herein by reference.

FIELD

Aspects of the technology described herein relate to predicting whether a subject (e.g., a patient) is likely to respond positively or not likely to respond positively to an immune checkpoint blockade therapy based on subject-specific information such as, for example, the subject's gene expression data. In particular, some aspects of the technology described herein relate to training a statistical model for predicting efficacy of an immune checkpoint blockade therapy using gene expression data, and using the trained statistical model to identify a subject as a "responder" or "non-responder" with regard to their response to an immune checkpoint blockade therapy. In some embodiments, the statistical model may include variables representing ratios of gene expression levels of pairs of genes.

BACKGROUND

Immune checkpoint blockade therapies have shown long-term efficacy for various cancer types, yet only a subset of patients respond to these treatments. Techniques for identifying patients that will respond to immune checkpoint blockade therapy, as well as patients that will not respond to immune checkpoint blockade therapy, are needed.

SUMMARY

Provided herein, inter alia, are systems and methods for determining whether a subject is likely to respond positively or not likely to respond positively to an immune checkpoint blockade therapy. Such information, in some embodiments, is output to a user in a graphical user interface (GUI).

Systems and methods for determining whether the subject is a responder or non-responder to an immune checkpoint blockade therapy comprises, in some embodiments, obtaining expression data for each subject in a plurality of subjects having responders to an immune checkpoint blockade therapy and non-responders to the immune checkpoint blockade therapy, determining expression level differences between the responders and non-responders using the expression data, identifying a subset of genes differentially expressed in responders and non-responders, generating a statistical model for predicting efficacy of the immune checkpoint blockade therapy using at least some of the subset of genes as a predictor set of genes and the expression data, obtaining additional expression data for an additional subject, and determining whether the additional subject is likely to respond positively to the immune checkpoint blockade therapy.

Provided herein, inter alia, are systems and methods for determining whether a subject is likely to have or not likely to have an adverse reaction to an immune checkpoint blockade therapy. Such information, in some embodiments, is output to a user in a graphical user interface (GUI).

Systems and methods for determining whether the subject is likely to have or not likely to have an adverse reaction to an immune checkpoint blockade therapy comprises, in some embodiments, obtaining expression data for each subject in a plurality of subjects having and subjects not having an adverse reaction to the immune checkpoint blockade therapy, determining expression level differences between the subjects having and subjects not having an adverse reaction using the expression data, identifying a subset of genes differentially expressed in subjects having and subjects not having an adverse reaction, generating a statistical model for predicting adverse effects of the checkpoint blockade therapy using at least some of the subset of genes as a predictor set of genes and the expression data, obtaining additional expression data for an additional subject, and determining whether the additional subject is likely to have the adverse reaction to the checkpoint blockade therapy.

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with the checkpoint blockade therapy in the plurality of genes, wherein identifying the subset of genes associated with the checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is at least one non-transitory computer-readable storage medium storing processor-executable instructions that, when executed by at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with the checkpoint blockade therapy in the plurality of genes, wherein identifying the subset of genes associated with the checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is a method, comprising: using at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with the checkpoint blockade therapy in the plurality of genes, wherein identifying the subset of genes associated with the checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with the checkpoint blockade therapy in the plurality of genes, wherein identifying the subset of genes associated with the checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying predictor set of genes to include in the statistical model; estimating, using the expression data, parameters of the statistical model that are associated with the predictor set of genes; and storing the statistical model.

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: accessing a statistical model, wherein the statistical model was obtained by: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with the checkpoint blockade therapy in the plurality of genes, wherein identifying the subset of genes associated with the checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is a method for determining whether or not a subject is likely to respond to a checkpoint blockade therapy, the method comprising: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

In one aspect provided herein is a system for determining whether or not a subject is likely to respond to a checkpoint blockade therapy, the system comprising: at least one computer hardware processor; and at least one non-transitory computer readable storage medium storing processor-executable instructions that, when executed by the at least one computer hardware processor, causes the at least one computer hardware processor to perform: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

In one aspect provided herein is at least one non-transitory computer readable storage medium storing processor-executable instructions that, when executed at least one computer hardware processor, causes the at least one computer hardware processor to perform a method for determining whether or not a subject is likely to respond to a checkpoint blockade therapy: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

BRIEF DESCRIPTION OF THE DRAWINGS

Various aspects and embodiments will be described with reference to the following figures. The figures are not necessarily drawn to scale.

FIG. 3D shows data from a principal component analysis of the merged datasets, in accordance with some embodiments of the technology described herein.

FIG. 3E shows data from a principal component analysis of merged datasets combined with non-immune checkpoint blockade treated TCGA samples for SKCM melanoma (453 samples, SKCM453), in accordance with some embodiments of the technology described herein.

FIG. 4C shows data from a principal component analysis of 201 generated gene ratios for responders (R) and non-responders (NR), in accordance with some embodiments of the technology described herein.

FIG. 4E is a chart showing fold change (FC) values and U-test p values for 20 gene ratios for each dataset, in accordance with some embodiments of the technology described herein.

DETAILED DESCRIPTION

Figure 1A:
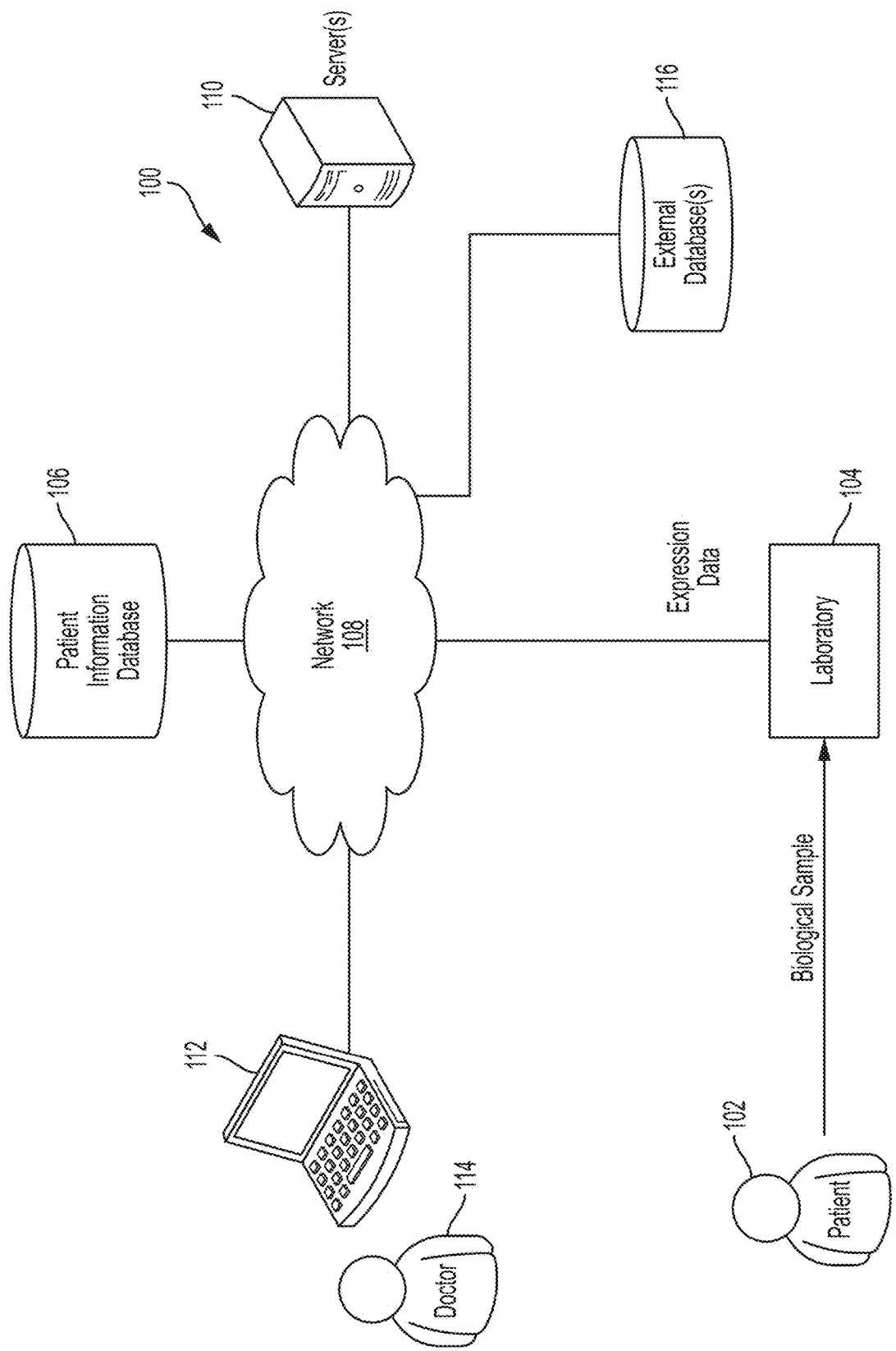
FIG. 1A is a block diagram of an illustrative environment 100 in which some embodiments of the technology described herein may be implemented.

Immune checkpoint blockade therapy has shown remarkable benefit in the treatment of a wide range of cancer types. Unfortunately, immune checkpoint blockade therapy is, at best, effective in only 50% of patients. Non-responsive patients experience a high risk of so-called "immune-related adverse events" in which patients develop organ specific immune-related adverse events (e.g., colitis and hepatitis) and general adverse events related to immune activation (e.g., fatigue and diarrhea). Conventional techniques for predicting a patient's response to an immune checkpoint blockade therapy (e.g., anti-PD1 therapy) based on characterization of a target ligand (e.g., PDL1) have shown limited success.

The inventors have developed techniques for both predicting the efficacy of immune checkpoint blockade therapy for a subject, and predicting likelihood of an adverse reaction for a subject treated with an immune checkpoint blockade therapy. In particular, the inventors have developed a novel statistical model for predicting efficacy of an immune checkpoint blockade therapy using gene expression data, and using the trained to statistical model to identify a subject as a "responder" or "non-responder" with regard to their response to an immune checkpoint blockade therapy. The statistical model may include variables representing ratios of gene expression levels for pairs of genes whose expression ratios may be indicative of a subject's response to an immune checkpoint blockade therapy.

In some embodiments, determining a patient's response to an immune checkpoint blockade therapy or lack thereof was correctly predicted for 94% of patients treated with an anti-PD1 therapy or an anti-CTLA4 therapy using a 12-gene expression ratio based statistical model. Unlike conventional techniques for predicting response to an immune checkpoint blockade therapy based on characterization of an immune checkpoint-related target, techniques provided herein determined therapeutic efficacy from expression of genes having diverse functions. For example, the 12-gene expression ratio based model included FYN encoding a tyrosine kinase, HAUS8 encoding a protein involved in mitotic spindle assembly, AGPAT3 encoding an acyltransferase, and RAI14 encoding a protein involved in actin bundling. In some embodiments, the 12-gene expression ratio may include ratios using genes selected from the group comprising: AGPAT3, BRAF, CMIP, FYN, HAUS8, PRKAG1, RAB40C, RAI14, ROBO4, SNAP23, SNX6, and STX2. In certain embodiments, the 12-gene expression ratio includes the following ratios: BRAF:RAI14, PRKAG1:STX2, AGPAT3:FYN, CMIP:ROBO4, RAB40C:HAUS8, and SNAP23:SNX6.

The 12-gene expression ratio based statistical model described herein was generated by a robust and global analysis of patient expression data made possible, in part, by recent advances in personalized genomic sequencing and cancer genomic sequencing technologies that have made it possible to readily obtain a patient's gene expression. The inventors identified the 12-gene expression ratio based statistical model by analyzing 10,000 highly expressed genes from four melanoma patient datasets, calculating approximately 50 million gene expression ratios, and evaluating the predictive efficacy of the ratios. In some embodiments, the statistical model may be based on more than 12 gene ratios. As a set of non-limiting examples, the statistical model may be based on 13, 14, 15, 16, 17, 18, 19, 20, 21, 22, 23, 24, 25, 26, 27, 28, 29, 30, or more ratios. In some embodiments, the 12-gene expression ratio may include or comprise ratios using genes selected from the group comprising: AGPAT3, BRAF, CMIP, FYN, HAUS8, PRKAG1, RAB40C, RAI14, ROBO4, SNAP23, SNX6, and STX2. In certain embodiments, the 12-gene expression ratio includes or comprises the following ratios: BRAF:RAI14, PRKAG1:STX2, AGPAT3:FYN, CMIP:ROBO4, RAB40C:HAUS8, and SNAP23:SNX6.

The inventors have recognized that several of the elements described herein add something more than what is well understood, routine, or conventional activity proposed by others in the field. These meaningful non-routine steps result in the improvements seen in the methods, systems, and GUIs described herein and include, but are not limited to; identification of gene expression ratios that may be used to more accurately predict a patient's response to an immune checkpoint blockade therapy than conventional techniques based on characterization of immune checkpoint targets; technical improvements in analyses that allow for more accurate prediction of a patient's response to an immune checkpoint blockade therapy and resulting improvements in outcome for the patient; and the creation of improved graphical user interfaces to aid in the selection of a therapy.

Therefore, aspects of the technology described herein relate to systems and methods for predicting a patient's response to an immune checkpoint blockade therapy based on patient-specific information such as, for example, a patient's gene expression data. In some embodiments, predicting a patient's response to an immune checkpoint blockade therapy comprises determining ratios of gene expression levels or transformed gene expression levels for certain pairs of genes using sequencing data for the patient.

Such methods and systems may be useful for clinical purposes including, for example, evaluating likelihood of a beneficial response to an immune checkpoint blockade therapy for a subject (e.g., a patient), evaluating suitability of a patient for participating in a clinical trial, or determining a course of treatment with an immune checkpoint blockade therapy for a subject.

The methods and systems described herein may also be useful for non-clinical applications including (for example) research purposes such as, e.g., studying the biological pathways and/or biological processes targeted by an immune checkpoint blockade therapy, and developing new immune checkpoint therapies for cancer based on such studies.

Accordingly, some embodiments include techniques for training a statistical model to predict a subject's response to an immune checkpoint blockade therapy. Such techniques may include: (A) obtaining, for each subject in a plurality of subjects having responders to an immune checkpoint blockade therapy (e.g., a PD1 inhibitor therapy, a CTLA4 inhibitor therapy) and non-responders to the immune checkpoint blockade therapy, expression data (e.g., RNA expression data, DNA expression data, and/or protein expression data) indicating expression levels for a plurality of genes; (B) determining, for the plurality of genes, expression level differences between the responders and the non-responders using the expression data; (C) identifying, using the determined expression level differences, a subset of genes associated with an immune checkpoint blockade therapy in the plurality of genes, wherein identifying the subset of genes associated with an immune checkpoint blockade therapy comprises identifying genes that are differentially expressed between the responders and non-responders with at least a threshold level of statistical significance; and (D) training, using the expression data, a statistical model for predicting efficacy of the immune checkpoint blockade therapy.

In some embodiments, the training may include: (A) identifying at least some of the subset of genes as a predictor set of genes to include in the statistical model; and (B) estimating, using the expression data, parameters of the statistical model that are associated with the predictor set of genes;

In some embodiments, the trained statistical model may be saved for subsequent use and/or may be used to predict efficacy of an immune checkpoint blockade therapy for one or more other subjects. Using the trained statistical model to predict efficacy of an immune checkpoint blockade therapy may include: (A) obtaining additional expression data for an additional subject; and (B) determining, using the additional expression data and the trained statistical model, whether the additional subject is likely to respond positively to the immune checkpoint blockade therapy and/or whether the additional subject is not likely to respond positively to the immune checkpoint blockade therapy.

In some embodiments, the statistical model may be a generalized linear model (e.g., a logistic regression model, a probit regression model, etc.) having a regression variable for each of the predictor set of genes. In some embodiments, each variable in the statistical model (e.g., each regression variable in the generalized linear model) may represent a ratio of a pair of genes for respective pairs of members of the predictor set of genes. Thus, in some embodiments, each variable of the statistical model may represent an individual gene expression level, while in other embodiments, each variable of the statistical model may represent a gene expression level ratio for a pair of genes.

It should be appreciated that, in some embodiments, the statistical model may not be a generalized linear model and may be a different type of statistical model such as, for example, a random forest regression model, a neural network, a support vector machine, a Gaussian mixture model, a hierarchical Bayesian model, and/or any other suitable statistical model, as aspects of the technology described herein are not limited to using generalized linear models for the prediction of immune checkpoint blockade therapy efficacy.

In some embodiments, the generalized linear model includes a respective weight for each of its regression variables and estimating the parameters of the generalized linear model includes estimating the weights using the expression data for the plurality of subjects and information indicating which of the plurality of subjects responded to the immune checkpoint blockade therapy and/or which of the plurality of subjects did not respond to the immune checkpoint blockade therapy.

In some embodiments, training the statistical model includes selecting variables to include in the statistical model. This may be done in any suitable way and, for example, may be done by iteratively adding regression variables for respective genes to the statistical model.

In some embodiments, iteratively adding regression variables comprises: identifying a candidate gene in the subset of genes; augmenting a current statistical model with a regression variable for the candidate gene to obtain an augmented statistical model; evaluating performance of the augmented statistical model (e.g., by calculating the area under a receiver operating characteristic curve statistic or in any other suitable way); and determining to add the regression variable for the candidate gene to the current statistical model based on results of evaluating the performance.

As may be appreciated from the foregoing, selecting which variables to include in the statistical model is done in two stages. The first stage involves identifying the subset of genes associated with an immune checkpoint blockade therapy comprises identifying genes that are differentially expressed between the responders and non-responders with at least a threshold level of statistical significance. Any number of genes may be analyzed in order to determine which genes are differentially expressed between the responders and non-responders with at least a threshold level of statistical significance (e.g., 1,000 genes, 1,250 genes, 1,500 genes, 1.750 genes, 2,000 genes, 2,250 genes, 2,500 genes, 2.750 genes, 3,000 genes, 3,250 genes, 3,500 genes, 3.750 genes, 4,000 genes, 5,000 genes, 6,000 genes, 7,000 genes, 8,000 genes, 9,000 genes, 10,000 genes, or more). The subset of genes identified during the first stage as being differentially expressed between the responders and non-responders with at least a threshold level of statistical significance may be any subset of the tested genes including, for example, 250 genes, 300 genes, 350 genes, 400 genes, 450 genes, 500 genes, 550 genes, 600 genes, 650 genes, 700 genes, 750 genes, 800 genes, 850 genes, 900 genes, 950 genes, 1,000 genes, 1,050 genes, 1,100 genes, 1,150 genes, 1,200 genes, 1,250 genes, 1,300 genes, 1,350 genes, 1,400 genes, 1,450 genes, 1,500 genes, or more. The second stage involves selecting, from the subset of genes identified during the first stage, a predictor set of genes to use as part of the statistical model. The predictor set of genes will be a significantly smaller set of genes than that identified in the first stage and may be, for example, 6, 7, 8, 9, 10, 11, 12, 13, 14, 15, 16, 17, 18, 19, 20, 21, 22, 23, 24, 25, or 26 genes.

The inventors appreciated that, after the first stage, too many combinations of genes existed in order to accurately identify a set of genes with the greatest predictive capacity for whether a subject would be a responder or a non-responder to a particular immune checkpoint blockade therapy (here, a predictor set). Therefore, the inventors recognized that a second (greedy) stage of identification as required in order to identify such a predictor set of genes. As an illustrative example, if 10,000 gene levels were initially analyzed, 1,000 genes might be identified as being differentially expressed between the responders and non-responders with at least a threshold level of statistical significance. There would not be enough training data to train a statistical model for predicting whether a subject will respond to an immune checkpoint blockade therapy with 1,000 variables. If the identified subset of genes were to be systematically analyzed in (for example) groups of 10 in order to determine which genes had the best predictive capacity, approximately 2.6340956e+23 sets of analyses would need to be performed. Such calculations become even more onerous when ratios are analyzed, because each possible ratio would need to be analyzed with each gene in the numerator and in the denominator. Therefore, the inventors' use of an iterative approach has proven to be the most powerful method of identifying predictor sets of genes for use in the statistical models described herein.

Figure 4A:
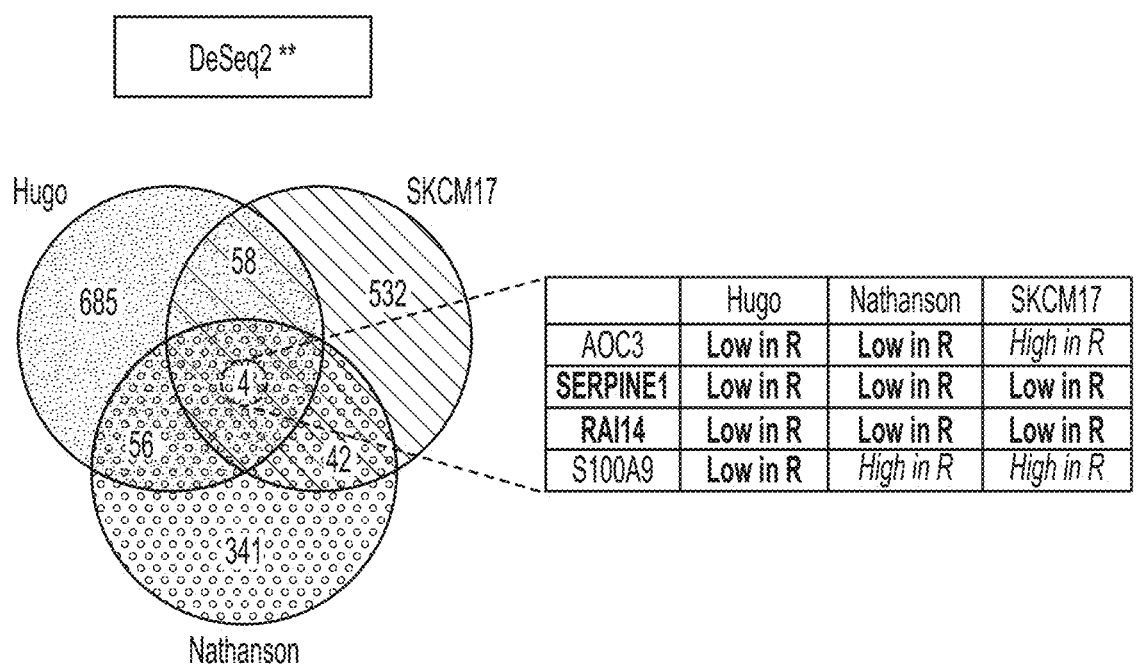
FIG. 4A is a graph showing shared differentially expressed genes between the Hugo, Nathanson, and SKCM17 datasets, in accordance with some embodiments of the technology described herein.
Figure 4B:
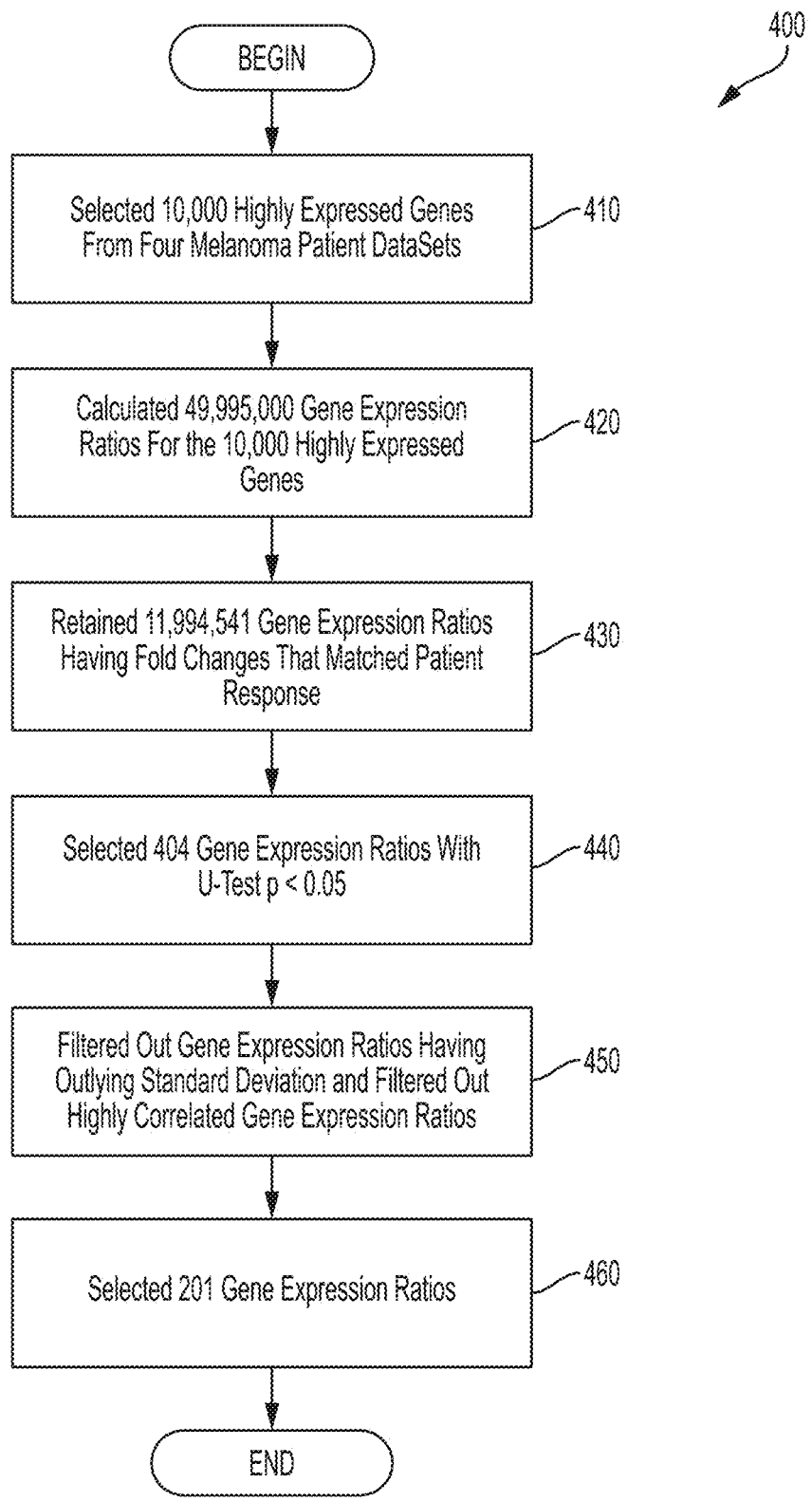
FIG. 4B is a flowchart of an illustrative process for identifying genes whose expression level ratios may be used to predict whether a subject will respond or will not respond to an immune checkpoint blockade therapy, in accordance with some embodiments of the technology described herein.

As shown in FIG. 4B, identifying the subset of genes associated with an immune checkpoint blockade therapy begins with selecting 10,000 highly expressed genes from four melanoma patient datasets, and calculating approximately 50 million gene expression ratios among the 10,000 highly expressed genes. Next, gene expression ratios having fold changes that matched the patient response (e.g., positive fold change matched with positive response) were selected yielding approximately 12 million gene expression ratios. The gene expression ratios most predictive of a therapy response were further selected to yield 201 highly predictive gene ratios.

Predicting Immune Checkpoint Blockade Therapy Response from Expression Data

Aspects of the technology described herein relate to systems and methods for predicting whether a subject (e.g., a patient) will respond positively to an immune checkpoint blockade therapy (e.g., a responder) or the subject will not respond positively to an immune checkpoint blockade therapy (e.g., a non-responder) based on patient-specific information such as a patient's expression data (e.g., expression levels and/or expression level differences).

Additionally, the systems and methods described herein may be used to predict whether a patient may or may not have one or more adverse reactions to an immune checkpoint blockade therapy, based on the patient's expression data.

The terms "subject" or "patient" may be used interchangeably and refer to a subject who needs the analysis as described herein. In some embodiments, the subject is a human or a non-human mammal (e.g., a non-human primate). In some embodiments, the subject is suspected to have cancer or is at risk for cancer. In some embodiments, the subject has (e.g., is known to have) cancer. Examples of cancer include, without limitation, adrenocortical carcinoma, bladder urothelial carcinoma, breast invasive carcinoma, cervical squamous cell carcinoma, endocervical adenocarcinoma, colon adenocarcinoma, esophageal carcinoma, kidney renal clear cell carcinoma, kidney renal papillary cell carcinoma, liver hepatocellular carcinoma, lung adenocarcinoma, lung squamous cell carcinoma, ovarian serous cystadenocarcinoma, pancreatic adenocarcinoma, prostate adenocarcinoma, rectal adenocarcinoma, skin cutaneous melanoma, stomach adenocarcinoma, thyroid carcinoma, uterine corpus endometrial carcinoma, one or more types of lymphoma, leukemia, and cholangiocarcinoma.

In some embodiments, the subject is a human patient having one or more cancer symptoms. For example, the subject may have fatigue, pain, weakness or numbness, loss of bladder or bowel control, cough, blood-tinged saliva, anemia, breast lump or discharge, or a combination thereof. In some embodiments, the subject has a symptom of cancer or has a history of a symptom of cancer. In some embodiments, the subject has more than one symptom of cancer or has a history of more than one symptoms of cancer. In some embodiments, the subject has no symptom of cancer, has no history of a symptom of cancer, or has no history of cancer.

Such a subject may exhibit one or more symptoms associated with a cancer. Alternatively or in addition, such a subject may have one or more risk factors for cancer, for example, an environmental factor associated with cancer (e.g., geographic location or exposure to a mutagen), a family history of cancer, and/or a genetic predisposition to developing cancer.

Alternatively, the subject who needs the analysis described herein may be a patient having cancer or suspected of having cancer. Such a subject may currently be having a relapse, or may have suffered from the disease in the past (e.g., may be currently relapse-free), or may have cancer. In some examples, the subject is a human patient who may be on a treatment (i.e., the subject may be receiving treatment) for the disease including, for example, a treatment involving chemotherapy or radiation therapy. In other instances, such a human patient may be free of such a treatment.

A variety of techniques may be used to determine whether a patient is a responder or a non-responder to an immune checkpoint blockade therapy and/or to determine whether that patient is likely to have an adverse reaction to such treatment. One example approach that may be used in some embodiments is identifying a patient as a responder or non-responder based on their gene expression level differences compared to those of responders and non-responders.

Another example approach that may be used in some embodiments is identifying a patient as likely to have an adverse reaction or not likely to have an adverse reaction based on their gene expression level differences compared to those having had a reaction and those that have not. Another example approach that may be used in some embodiments is identifying a patient as a responder or non-responder based on their expression level of certain genes compared to those of responders and non-responders.

It should be appreciated that the various aspects and embodiments described herein may be used individually, all together, or in any combination of two or more, as the technology described herein is not limited in this respect.

Computer Implemented Methods for Predicting or Describing Therapy Response

Aspects of the technology described herein provide computer implemented methods for determining, using expression data for a subject, gene expression level differences indicative of a patient's response or lack thereof to an immune checkpoint blockade therapy.

In some embodiments, a software program may provide a user with a visual representation presenting information related to a patient's expression data (e.g., expression levels and/or expression level differences), and predicted efficacy or determined efficacy of one or more checkpoint blockade therapies using a graphical user interface (GUI). Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

For example, in some embodiments, the techniques described herein may be implemented in the illustrative environment 100 shown in FIG. 1A. As shown in FIG. 1A, within illustrative environment 100, one or more biological samples of a patient 102 may be provided to a laboratory 104. Laboratory 104 may process the biological sample(s) to obtain expression data (e.g., DNA, RNA, and/or protein expression data) and provide it, via network 108, to at least one database 106 that stores information about patient 102.

Network 108 may be a wide area network (e.g., the Internet), a local area network (e.g., a corporate Intranet), and/or any other suitable type of network. Any of the devices shown in FIG. 1A may connect to the network 108 using one or more wired links, one or more wireless links, and/or any suitable combination thereof.

In the illustrated embodiment of FIG. 1A, the at least one database 106 may store expression data for the patient, medical history data for the patient, test result data for the patient, and/or any other suitable information about the patient 102. Examples of stored test result data for the patient include biopsy test results, imaging test results (e.g., MRI results), and blood test results. The information stored in at least one database 106 may be stored in any suitable format and/or using any suitable data structure(s), as aspects of the technology described herein are not limited in this respect. The at least one database 106 may store data in any suitable way (e.g., one or more databases, one or more files). The at least one database 106 may be a single database or multiple databases.

As shown in FIG. 1A, illustrative environment 100 includes one or more external databases 116, which may store information for patients other than patient 102. For example, external databases 116 may store expression data (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 116 may store information available in one or more publically accessible databases such as TCGA (The Cancer Genome Atlas), one or more databases of clinical trial information, and/or one or more databases maintained by commercial sequencing suppliers. The external database(s) 116 may store such information in any suitable way using any suitable hardware, as aspects of the technology described herein are not limited in this respect.

In some embodiments, the at least one database 106 and the external database(s) 116 may be the same database, may be part of the same database system, or may be physically co-located, as aspects of the technology described herein are not limited in this respect.

In some embodiments, information stored in patient information database 106 and/or in external database(s) 116 may be used to perform any of the techniques described herein related to determining whether a subject is likely to respond positively or not likely to respond positively to an immune checkpoint blockade therapy. For example, the information stored in the database(s) 106 and/or 116 may be accessed, via network 108, by software executing on server(s) 110 to perform any one or more of the techniques described herein in connection with FIGS. 2A, 2B, and 2C.

For example, in some embodiments, server(s) 110 may access information stored in database(s) 106 and/or 116 and use this information to perform process 200, described with reference to FIG. 2A, for determining whether a subject is likely to respond positively or not likely to respond positively to an immune checkpoint blockade therapy. In some embodiments, the server(s) 110 may use information stored in database(s) 106 and/or 116 to train a statistical model for predicting whether the subject is likely to respond positively or not to an immune checkpoint blockade therapy.

As another example, server(s) 110 may access information stored in database(s) 106 and/or 116 and use this information to perform process 220, described with reference to FIG. 2B, for determining whether a subject is likely to have an adverse reaction or not likely to have an adverse reaction to an immune checkpoint blockade therapy. In some embodiments, the server(s) 110 may use information stored in database(s) 106 and/or 116 to train a statistical model for predicting whether the subject is likely to have an adverse reaction or not likely to have an adverse reaction to an immune checkpoint blockade therapy.

As yet another example, server(s) 110 may access information stored in database(s) 106 and/or 116 and use this information to perform process 240, described with reference to FIG. 2C, for determining whether a subject is likely or not likely to respond to a PD1 inhibitor and/or a CTLA4 inhibitor.

In some embodiments, server(s) 110 may include one or multiple computing devices. When server(s) 110 include multiple computing devices, the device(s) may be physically co-located (e.g., in a single room) or distributed across multi-physical locations. In some embodiments, server(s) 110 may be part of a cloud computing infrastructure. In some embodiments, one or more server(s) 110 may be co-located in a facility operated by an entity (e.g., a hospital, research institution) with which doctor 114 is affiliated. In such embodiments, it may be easier to allow server(s) 110 to access private medical data for the patient 102.

As shown in FIG. 1A, in some embodiments, the results of the analysis performed by server(s) 110 may be provided to doctor 114 through a computing device 114 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 1A, the results are provided to a doctor, in other embodiments, the results of the analysis may be provided to patient 102 or a caretaker of patient 102, a healthcare provider such as a nurse, or a person involved with a clinical trial.

In some embodiments, the results may be part of a graphical user interface (GUI) presented to the doctor 114 via the computing device 112. In some embodiments, the GUI may be presented to the user as part of a webpage displayed by a web browser executing on the computing device 112. In some embodiments, the GUI may be presented to the user using an application program (different from a web-browser) executing on the computing device 112. For example, in some embodiments, the computing device 112 may be a mobile device (e.g., a smartphone) and the GUI may be presented to the user via an application program (e.g., "an app") executing on the mobile device.

The GUI presented on computing device 112 provides a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology.

Figure 1B:
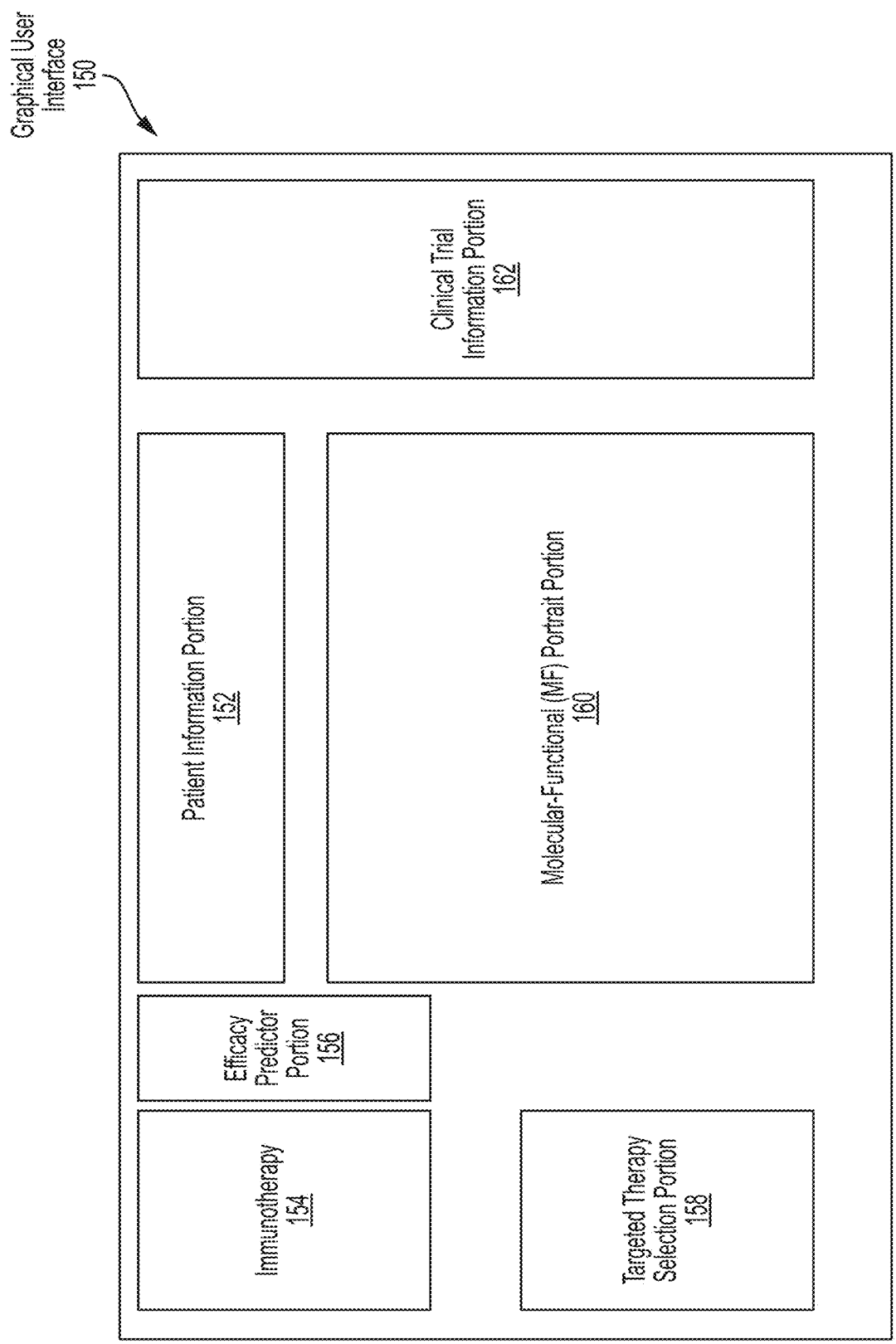
FIG. 1B is a block diagram of an illustrative graphical user interface 150 including patient data that may be presented to a user (e.g., a doctor), in accordance with some embodiments of the technology described herein.

FIG. 1B shows a block diagram of an illustrative GUI 150 containing information about patient 102. GUI 150 may include separate portions providing different types of information about patient 102. Illustrative GUI 150 includes the following portions: Patient Information Portion 152, Molecular-Functional (MF) Portrait Portion 160, Clinical Trial Information Portion 162, Immunotherapy Portion 154, Efficacy Predictor Portion 156, and Targeted Therapy Selection Portion 158.

Patient Information Portion 152 may provide general information about the patient and the patient's cancer. General information about the patient may include such information as the patient's name and date of birth, the patient's insurance provider, and contact information for the patient such as address and phone number. General information about the patient's cancer may include the patient's diagnosis, the patient's history of relapse and/or remission, and information relating to stage of the patient's cancer. Patient Information Portion 152 may also provide information relating to potential treatment options for the patient and/or previously administered treatments.

Molecular-Functional (MF) Portrait Portion 160 may include a molecular functional tumor portrait (MF profile) which refers to a graphical depiction of a tumor with regard to its molecular and cellular composition, and biological processes that are present within and/or surrounding the tumor. Further aspects relating to a patient's MF profile are provided in International patent application number PCT/US18/37017, entitled "Systems and Methods for Generating, Visualizing and Classifying Molecular Functional Profiles," filed Jun. 12, 2018, the entire contents of which are incorporated herein by reference.

Clinical Trial Information Portion 162 may include information relating to a clinical trial for a therapy that may be and/or will be administered to the patient. Clinical Trial Information Portion 162 may provide information about an ongoing clinical trial or a completed clinical trial. Information that may be provided in Clinical Trial Information Portion 162 may include information related to a therapy used in the clinical trial such as dosage and dosage regimen, number and diagnosis of patients participating in the clinical trial, and patient outcomes.

Immunotherapy Portion 154 may include patient specific information as it relates to an immunotherapy. Immunotherapy Portion 154 may provide such information for different immunotherapies, for example, immune checkpoint blockade therapies, anti-cancer vaccine therapies, and T cell therapies. Patient specific information relating to an immunotherapy may include information about the patient such as the patient's biomarkers associated with an immunotherapy and/or information about the patient's cancer such as composition of immune cells in the patient's tumor.

Efficacy Predictor Portion 156 may include information indicative of the patient's predicted response to an immunotherapy based on patient specific information presented in Immunotherapy Portion 154. Efficacy Predictor Portion 156 may provide predicted efficacy of an immunotherapy determined, in some embodiments, using a patient's biomarkers as described in International patent application number PCT/US18/37008, entitled "Systems and Methods for Identifying Cancer Treatments from Normalized Biomarker Scores," filed Jun. 12, 2018, the entire contents of which are incorporated herein by reference. Additionally or alternatively, Efficacy Predictor Portion 156 may provide predicted efficacy of an immune checkpoint blockade therapy determined as described herein using patient specific information such as gene expression data.

Targeted Therapy Selection Portion 158 may include patient specific information as it relates to a targeted therapy. Targeted Therapy Selection Portion 158 may provide such information for different targeted therapies, for example, a kinase inhibitor therapy, a chemotherapy, and anti-cancer antibody therapy. Patient specific information relating to a targeted therapy may include information about the patient such as the patient's biomarkers associated with a targeted therapy and/or information about the patient's cancer such as whether a mutation is present in the patient's tumor.

Figure 1C:
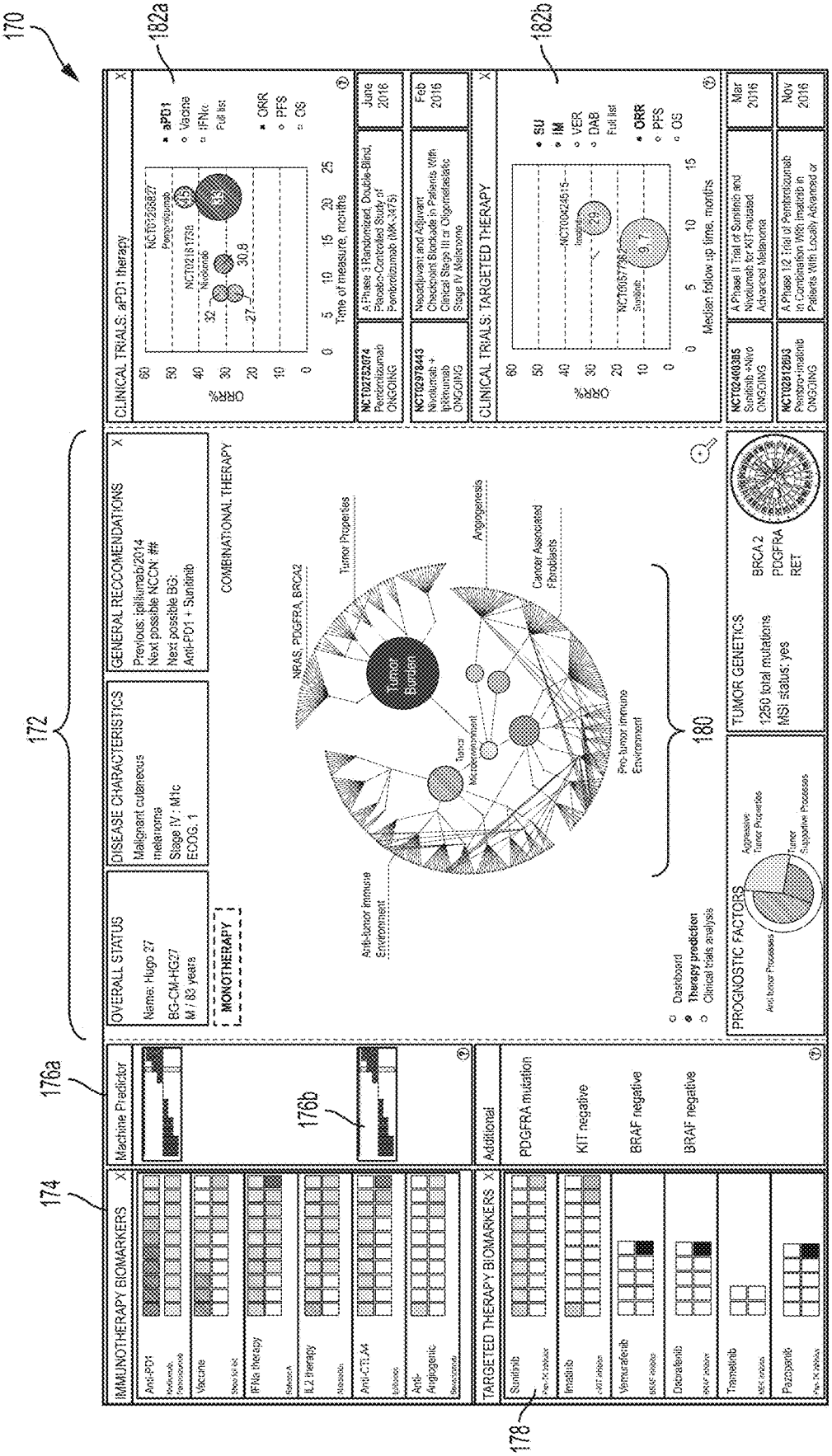
FIG. 1C is an illustrative example of the graphical user interface 150 of FIG. 1B, in accordance with some embodiments of the technology described herein.

An illustrative example of the graphical user interface 150 of FIG. 1B is shown as graphical user interface 170 of FIG. 1C. As shown in FIG. 1C, Patient Information Portion 172 may provide different information in different panels, for example, Overall Status panel, Disease Characteristics panel, and General Recommendations panel. Overall Status panel, in some embodiments, may provide general information about the patient such as patient name and patient age. Disease Characteristics panel, in some embodiments, may provide information about the patient's cancer such as type of cancer and stage of cancer. General Recommendations panel, in some embodiments, may provide previous treatments and possible treatment options for the patient.

Clinical Trial Information Portion 182a provides information relating to a clinical trial for anti-PD1 therapy. Clinical Trial Information Portion 182a (as shown in the upper portion) shows a graph providing patient overall response rate (ORR) for anti-PD1 therapy and other therapies such as vaccine or IFNα therapies. A user may select portions of the Clinical Trial Information Portion 182a to access information related to patient progression-free survival (PFS) and/or patient overall survival (OS). Clinical Trial Information Portion 182a (as shown in the lower portion) provides information relating to different clinical trials that may be presented to a user including a brief description of the clinical trial.

Clinical Trial Information Portion 182b provides information relating to a clinical trial for different targeted therapies. Clinical Trial Information Portion 182b (as shown in the upper portion) shows a graph providing patient overall response rate (ORR) for different targeted therapies including sunitinib (SU), imatinib (IM), vemurafenib (VER) and dabrafenib (DAB). A user may select portions of the Clinical Trial Information Portion 182b to access information related to patient progression-free survival (PFS) and/or patient overall survival (OS). Clinical Trial Information Portion 182b (as shown in the lower portion) provides information relating to different clinical trials that may be presented to a user including a brief description of the clinical trial.

Immunotherapy Portion 174 provides patient specific information associated with an immunotherapy and information indicative of the patient's predicted response to that immunotherapy. Immunotherapy Portion 174 provides such information for anti-PD1 therapy, a therapeutic cancer vaccine, IFNα therapy, IL2 therapy, anti-CTLA4 therapy, and anti-angiogenic therapy. Patient specific information shown in Immunotherapy Portion 174 includes the patient's biomarker information relating to various immunotherapies and the patient's therapy scores calculated from their biomarkers.

Efficacy Predictor Portion 176a provides information indicative of the patient's predicted response to anti-PD1 therapy based on patient specific information presented in Immunotherapy Portion 174. Efficacy Predictor Portion 176b provides information indicative of the patient's predicted response to anti-CTLA4 therapy based on patient specific information presented in Immunotherapy Portion 174.

Targeted Therapy Selection Portion 178 provides patient specific information associated with a targeted therapy and information indicative of the patient's predicted response to the targeted therapy. Targeted Therapy Selection Portion 178 provides such information for sunitinib (SU), imatinib (IM), vemurafenib (VER), dabrafenib (DAB), trametinib, and pazopanib. Patient specific information shown in Targeted Therapy Selection Portion 178 includes a patient's biomarker information relating to various targeted therapies and the patient's therapy scores calculated from their biomarkers.

Figure 6:
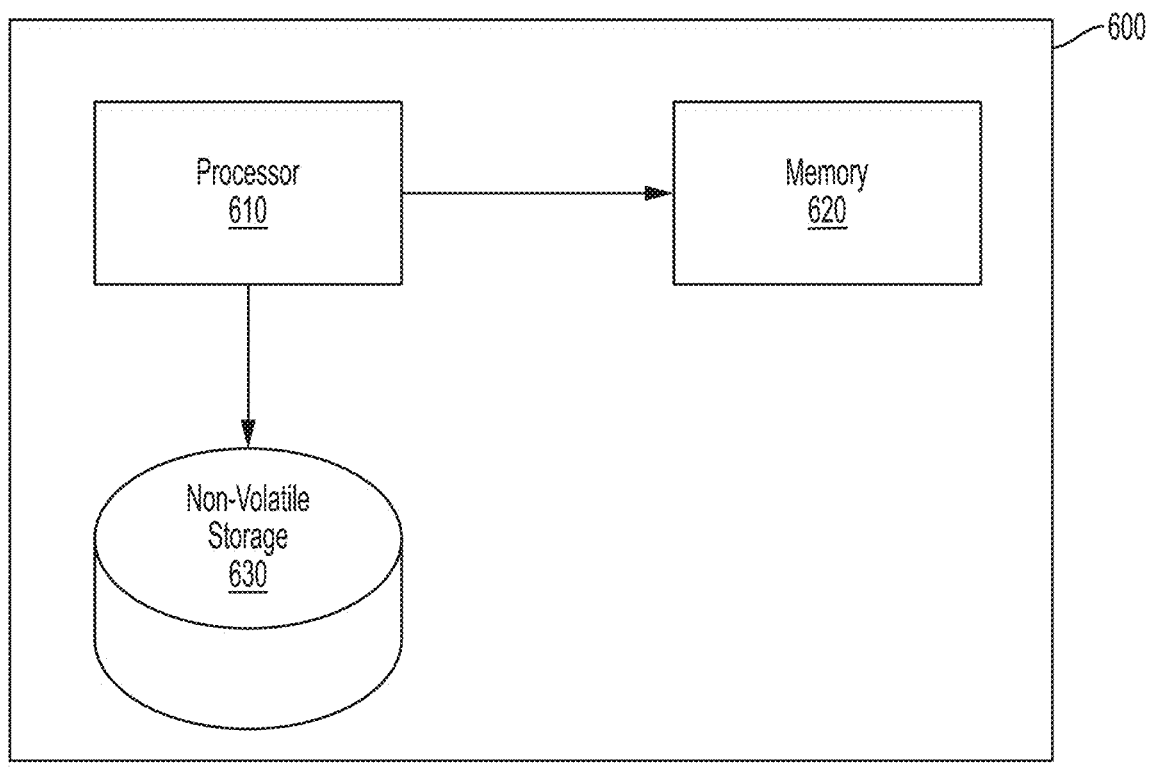
FIG. 6 shows components of an illustrative computer system on which some embodiments of the technology described herein may be implemented.

An illustrative implementation of a computer system 600 that may be used in connection with any of the embodiments of the technology described herein is shown in FIG. 6. The computer system 600 may include one or more computer hardware processors 600 and one or more articles of manufacture that comprise non-transitory computer-readable storage media (e.g., memory 620 and one or more non-volatile storage devices 630). The processor(s) 610 may control writing data to and reading data from the memory 620 and the non-volatile storage device(s) 630 in any suitable manner. To perform any of the functionality described herein, the processor(s) 610 may execute one or more processor-executable instructions stored in one or more non-transitory computer-readable storage media (e.g., the memory 620), which may serve as non-transitory computer-readable storage media storing processor-executable instructions for execution by the processor(s) 610.

Figure 2A:
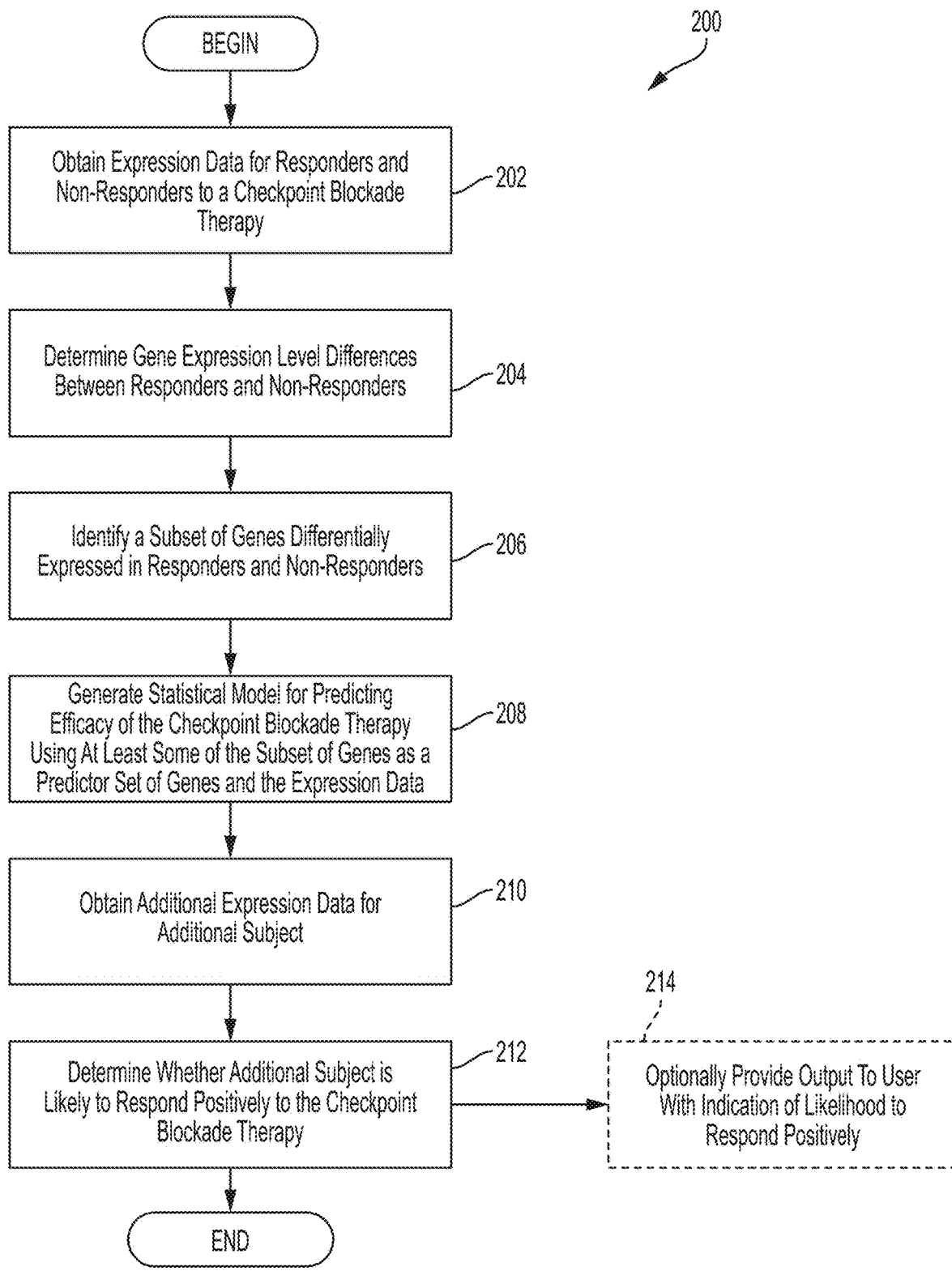
FIG. 2A is a flowchart of an illustrative process for determining whether a subject is likely to respond positively to an immune checkpoint blockade therapy, in accordance with some embodiments of the technology described herein.

FIG. 2A is a flowchart of an illustrative computer-implemented process 200 for determining whether an additional subject is likely to respond positively to an immune checkpoint blockade therapy, in accordance with some embodiments of the technology described herein. Process 200 may be performed by any suitable computing device(s). For example, may be performed by a laptop computer, a desktop computer, one or more servers, in a cloud computing environment, or in any other suitable way.

Process 200 begins at act 202, where expression data for responders and non-responders to an immune checkpoint blockade therapy is obtained. Examples of expression data include, but are not limited to, RNA expression data, DNA expression data, and protein expression data. In some embodiments, obtaining expression data comprises obtaining expression data from a biological sample of any number patients and/or from a database storing such expression data. Expression data may be obtained for any number of patients and/or for a single patient in need of the analysis provided herein. Further aspects relating to obtaining expression data are provided in section "Obtaining Expression Data".

Next, process 200 proceeds to act 204, where gene expression level differences between responders and non-responders are determined. For example, gene expression level differences may be determined by comparing an expression level or a transformed expression level such as a log transformed expression level. Gene expression level differences may be determined as an absolute value that is independent of whether the gene expression level was elevated or reduced between responders and non-responders. Gene expression level differences for any number of genes and for any number of responders and non-responders may be determined. Further aspects relating to determining gene expression level differences between responders and non-responders are provided in section "Expression Levels and Expression Level Differences".

Next, process 200 proceeds to act 206, where a subset of genes differentially expressed in responders and non-responders are identified. For example, a subset of genes differentially expressed in responders and non-responders may be identified as any gene having an expression level that is altered in a responder compared to an expression level of that gene in a non-responder. An altered level of gene expression may be an increase or a decrease in expression of that gene between a responder and a non-responder. Any number of subsets of differentially expressed genes for any number of genes and/or for any number of responders and non-responders may be identified. Further aspects relating to identifying subsets of genes differentially expressed in responders and non-responders are provided in section "Expression Levels and Expression Level differences".

Next, process 200 proceeds to act 208, where a statistical model for predicting efficacy of the immune checkpoint blockade therapy is trained. In some embodiments, the training includes two stages: (1) a variable selection stage that involves identifying at least some of the subset of genes as a predictor set of genes to include into the statistical model; and (2) a parameter estimation stage that involves estimating, using the expression data for the subject obtained at act 202, parameters of the statistical model that are associated with the predictor set of genes. For example, in some embodiments in which the statistical model is a regression model (e.g., a linear regression model, a logistic regression model, a generalized linear model, etc.), the training performed at act 208 may involve: (1) identifying a predictor set of genes and adding a variable in the regression model for each of the genes to represent the gene's expression level or some suitable function thereof; and (2) estimating regression weights for each of the regression variables. As another example, in some embodiments in which the statistical model is a regression model (e.g., a linear regression model, a logistic regression model, a generalized linear model, etc.), the training performed at act 208 may involve: (1) identifying a predictor set of genes and adding a variable in the regression model for each of one or more pairs of genes in the predictor set the ratio of their expression levels or some suitable function thereof; and (2) estimating regression weights for each of the regression variables.

In some embodiments, the variable selection stage portion of the training may be performed iteratively. In some embodiments, the statistical model may be a regression model and the variable selection stage may involve iteratively adding regression variables by: (1) identify a candidate gene (or a candidate gene ratio) in the subset of genes associated with an immune checkpoint blockade therapy, which subset was identified at act 206; (2) augmenting the statistical model with a regression variable representing an expression level for the candidate gene (or the ratio of expression levels for a candidate gene ratio); (3) evaluating the performance augmented statistical model with the identified candidate gene (or candidate gene ratio); and determining whether to retain the candidate gene (or candidate gene ratio) in the augmented statistical model. The performance may be evaluated in any suitable way including by calculating a receiver operating characteristic (ROC) curve and determining the area underneath it. Further aspects of a statistical model as used herein are provided in section "Statistical Model".

Next, process 200 proceeds to act 210, where additional expression data for an additional subject is obtained. Expression data for an additional subject may be obtained by any suitable means as described in further detail in section "Obtaining Expression Data". Expression data for the additional subject may be obtained in the same manner used for obtaining expression data of the responders and non-responders. Alternatively or in addition to, expression data for the additional subject may be obtained in a manner different from that used to obtain expression data of the responders and non-responders. Further aspects relating to obtaining expression data are provided in section "Obtaining Expression Data".

Next, process 200 proceeds to act 212, where it is determined whether the addition subject is likely to respond positively to the immune checkpoint blockade therapy and/or is not likely to respond positively to the immune checkpoint blockade therapy. Such information may be output to a user, in some embodiments, by displaying the information to the user in a graphical user interface (GUI), including the information in a report, sending an email to the user, and/or in any other suitable way.

Figure 5A:
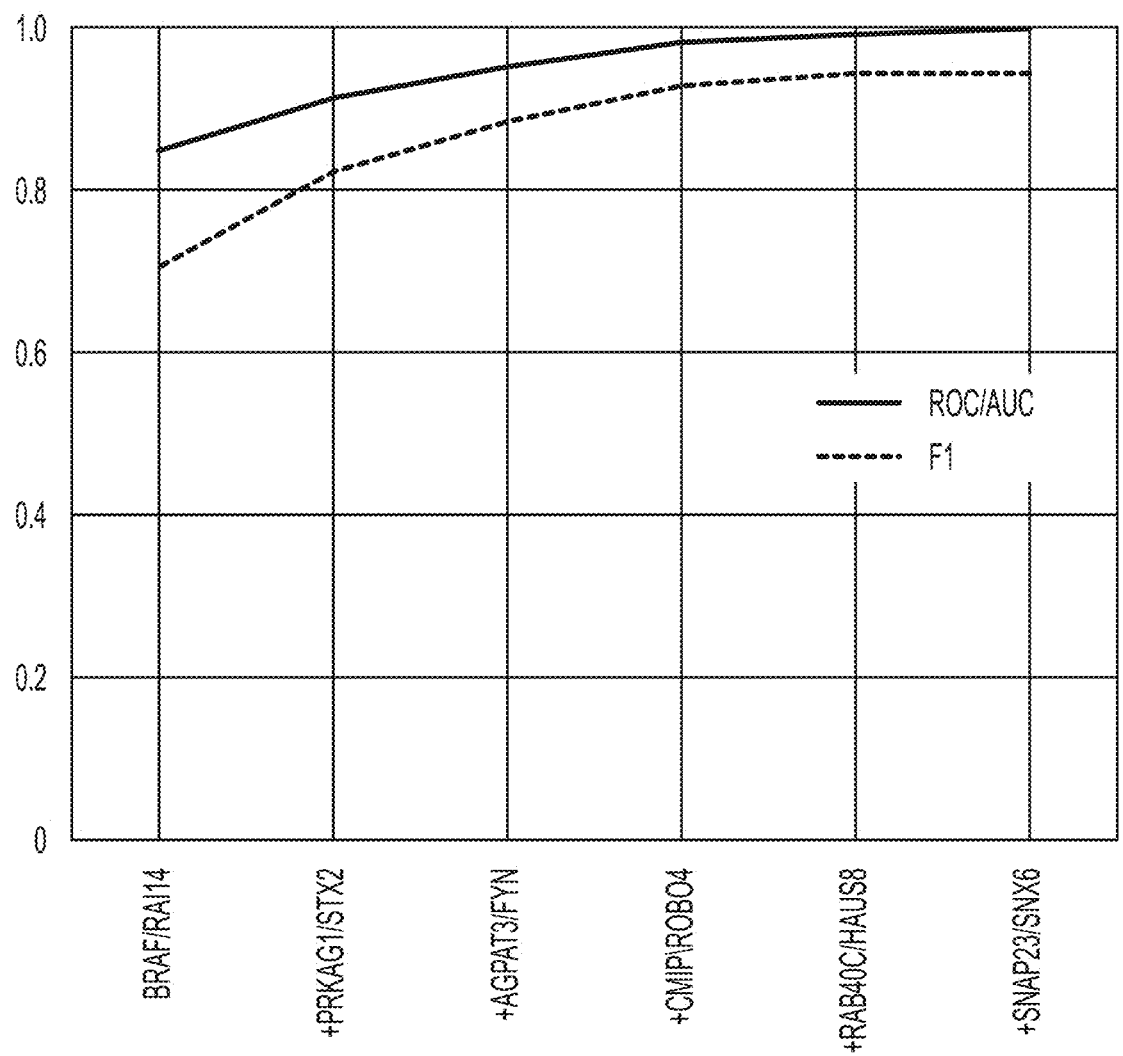
FIG. 5A is a graph showing ROC/AUC prediction scores from the statistical model for predicting whether a subject will response to an immune checkpoint blockade therapy, in accordance with some embodiments of the technology described herein.
Figure 5B:
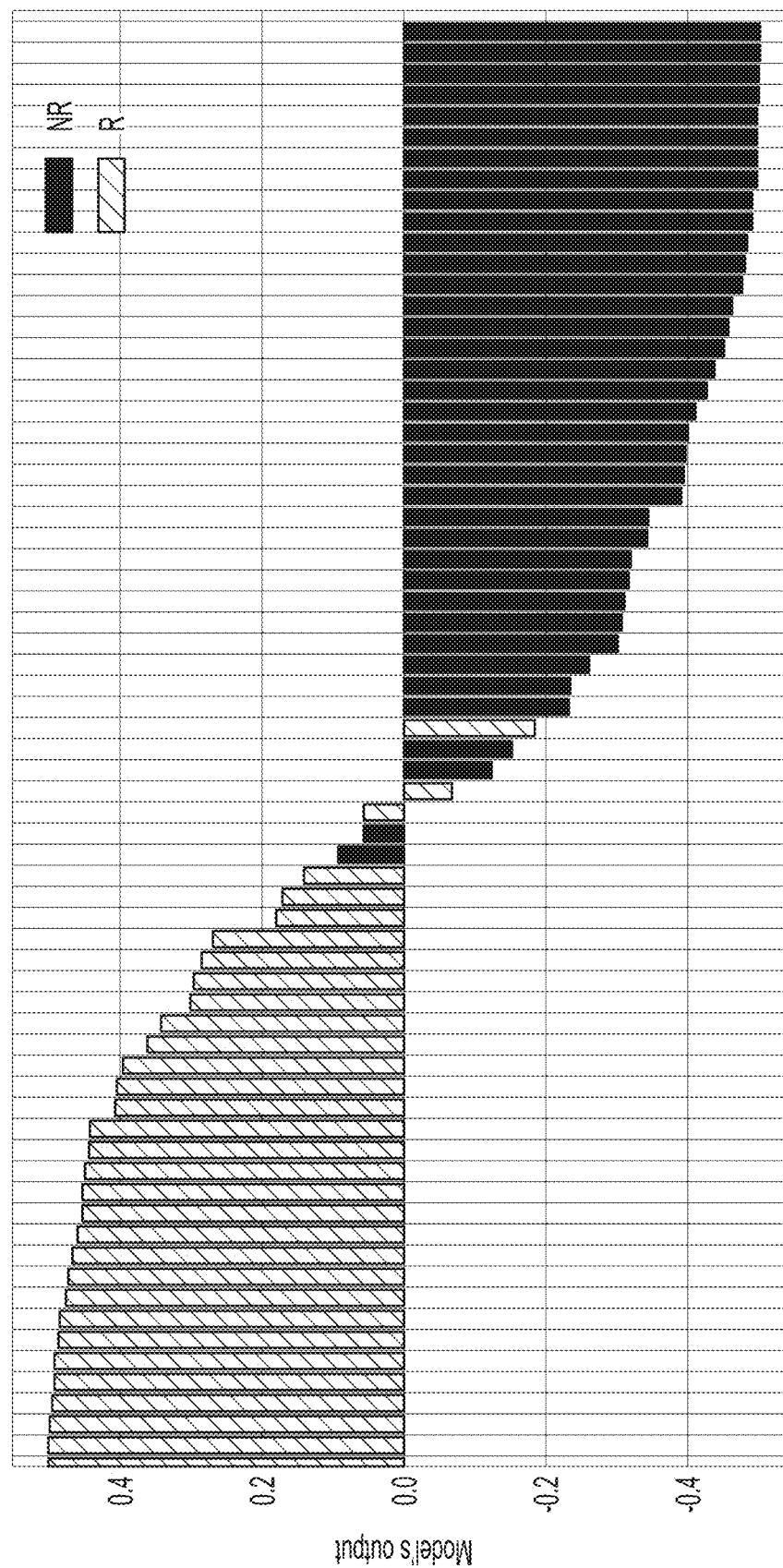
FIG. 5B is a waterfall plot of output scores from the statistical model for predicting whether a subject will response to an immune checkpoint blockade therapy over merged datasets, in accordance with some embodiments of the technology described herein. Responders are represented as "R" and non-responders are represented as "NR".
Figure 5C:
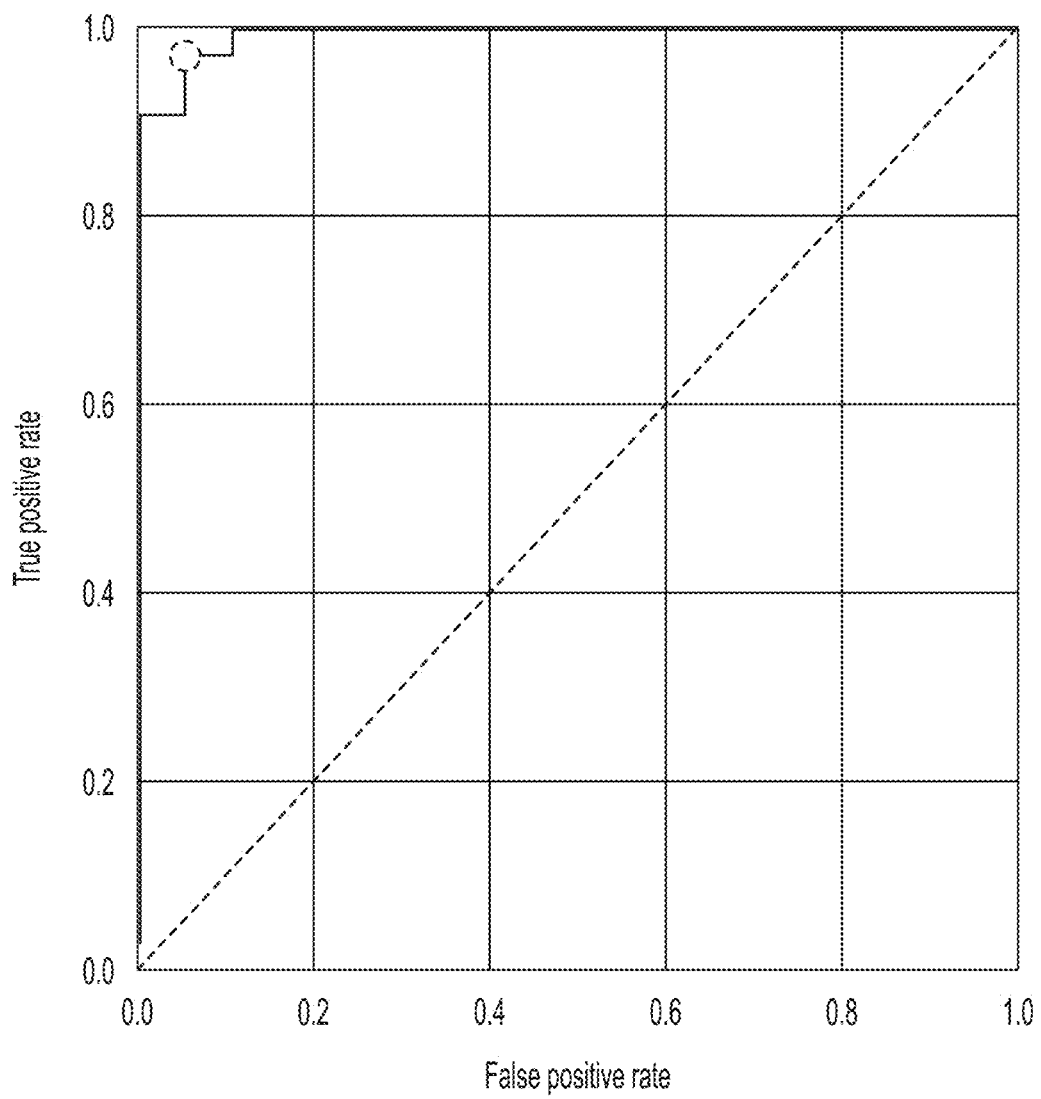
FIG. 5C is a graph showing a ROC curve of the statistical model for predicting whether a subject will response to an immune checkpoint blockade therapy over merged datasets, in accordance with some embodiments of the technology described herein.

In this way, a patient can be identified as a responder or non-responder based on their expression data compared to that of known responders and non-responders. One example of such an analysis is shown in FIG. 5B in which the statistical model's accuracy rate was approximately 94%.

Administration of an immune checkpoint blockade therapy exposes a patient to a high risk of experiencing an immune-related adverse reaction. Accordingly, a variety of techniques provided herein may be used to determine whether a patient will experience such adverse reactions.

Figure 2B:
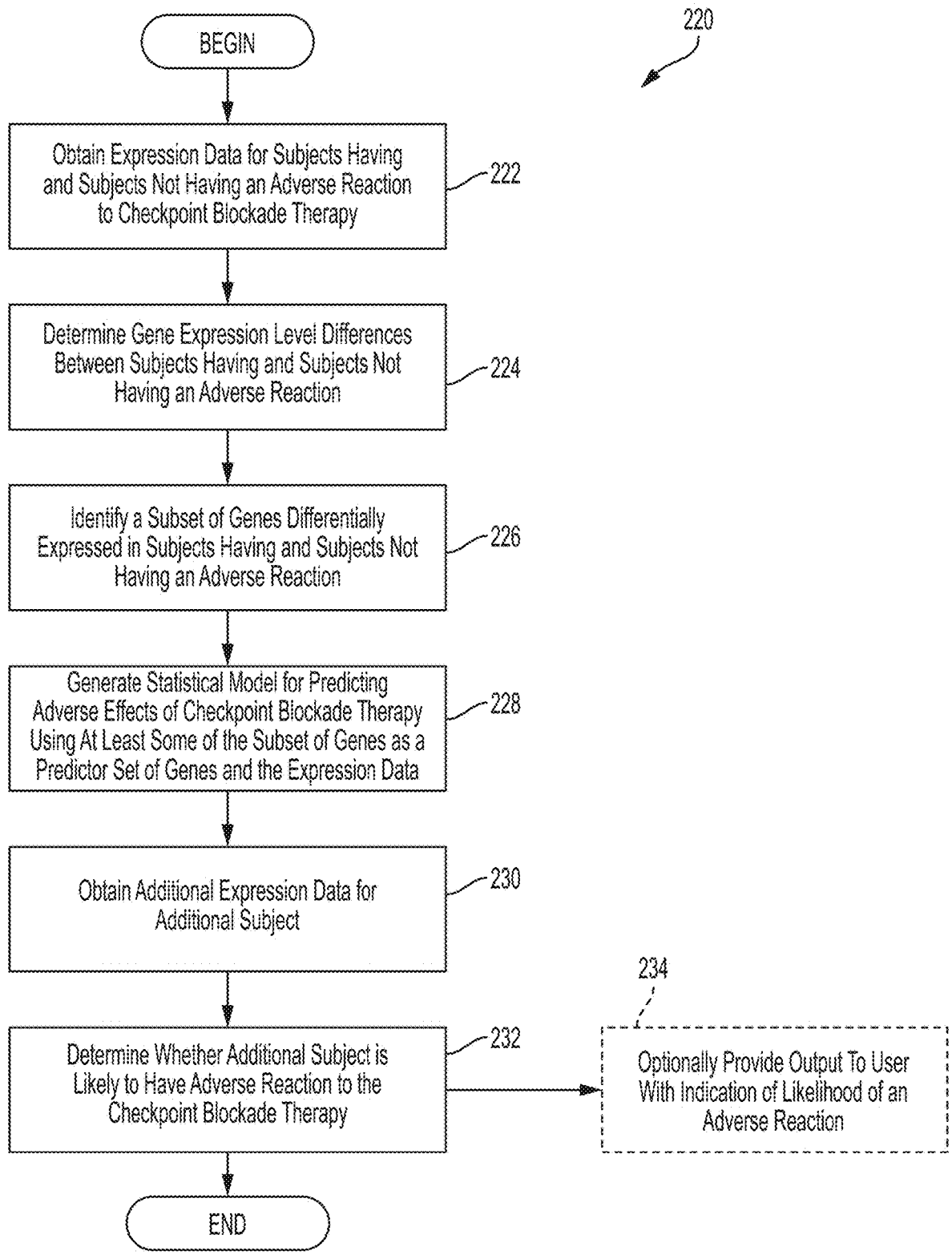
FIG. 2B is a flowchart of an illustrative process for determining whether a subject is likely to have an adverse reaction to an immune checkpoint blockade therapy, in accordance with some embodiments of the technology described herein.

FIG. 2B is a flowchart of an illustrative computer-implemented process 220 for determining whether an additional subject is likely to have an adverse reaction to an immune checkpoint blockade therapy, in accordance with some embodiments of the technology described herein.

Process 220 begins at act 222, wherein expression data for subjects having an adverse reaction and subjects not having an adverse reaction to an immune checkpoint blockade therapy is obtained. As described above, expression data may be obtained from a biological sample of a subject and/or from a database in which such information is stored. For example, RNA expression data, DNA expression data, and protein expression data may be obtained in act 222. Expression data may be obtained for any number of patients and/or for a single patient in need of the analysis provided herein. Further aspects relating to obtaining expression data are provided in section "Obtaining Expression Data".

A subject may have any immune-mediated adverse reaction to an immune checkpoint blockade therapy. An immune-mediated adverse reaction, in some embodiments, is an autoimmune toxicity in a system of organs, an organ, or a tissue. Examples of an organ or a system of organ and a tissue include, but is not limited to, skin, lung, gastrointestinal tract, liver, muscle, heart, and an endocrine organ (e.g., thyroid, adrenal glands, pituitary gland, and kidney).

Examples of immune-mediated adverse reactions include, but are not limited to, diarrhea, pruritus, infusion-related reactions, rash, transaminitis, rhabdomyolysis, colitis, hypothyroidism, pneumonitis, nephritis, hepatitis, cytokine release syndrome, paraplegia, pericardial effusion, increase in alkaline phosphatase, chronic kidney disease, hypotension, musculoskeletal pain, sepsis, adrenal insufficiency, diabetes, and hypophysitis.

Next, process 220 proceeds to act 224, where gene expression level differences between subjects having and subjects not having an adverse reaction are determined. For example, gene expression level differences may be determined by comparing an expression level or a transformed expression level such as a log transformed expression level. Gene expression level differences may be determined as an absolute value that is independent of whether the gene expression level was elevated or reduced between patients having and patients not having an adverse reaction. Gene expression level differences for any number of genes and for any number of subjects having and subjects not having an adverse reaction may be determined. Further aspects relating to determining gene expression level differences between patients having an adverse reaction and those that did not are provided in section "Expression Levels and Expression Level Differences".

Next, process 220 proceeds to act 226, where a subset of genes differentially expressed in subjects having and subjects not having an adverse reaction are identified. For example, a subset of genes differentially expressed in patient having or not having an adverse reaction may be identified as any gene having an expression level that is altered in a patient having an adverse reaction compared to an expression level of that gene in a patient not having an adverse reaction. An altered level of gene expression may be an increase or a decrease in expression of that gene between a patient having and a patient not having an adverse reaction. Any number of subsets of differentially expressed genes for any number of genes and/or for any number of subjects having and subjects not having an adverse reaction may be identified as described herein. Further aspects of identifying a subset of genes differentially expressed in subjects having and not having an adverse reaction are provided in section "Expression Levels and Expression Level differences".

Next, process 220 proceeds to act 228, wherein a statistical model for predicting adverse events of the immune checkpoint blockade therapy using at least some of the subset of genes and the expression data is generated. Aspects of a statistical model as used herein are provided in section "Statistical Model". Aspects of training the statistical model have been described above for FIG. 2A.

Next, process 220 proceeds to act 230, where additional expression data for an additional subject is obtained. Expression data for an additional subject may be obtained by any suitable means as described in further detail in section "Obtaining Expression Data". Expression data for the additional subject may be obtained in the same manner used for obtaining expression data of the subjects having and subjects not having an adverse reaction. Alternatively or in addition to, expression data for the additional subject may be obtained in a manner different from that used to obtain expression data of the subjects having and subjects not having an adverse reaction.

Next, process 220 proceeds to act 232, where it is determined whether the addition subject is likely to have an adverse event to the immune checkpoint blockade therapy and/or is not likely to have an adverse event to the immune checkpoint blockade therapy. Such information may be output to a user, in some embodiments, by displaying the information to the user in a graphical user interface (GUI), including the information in a report, sending an email to the user, and/or in any other suitable way.

In this way, a patient can be identified as likely to have or not likely to have an adverse reaction based on their expression data compared to that from patients previously identified as having or not having an adverse reaction.

It should be appreciated that expression levels or expression level differences may be used for determining whether a subject is likely to respond to an immune checkpoint blockade therapy. For example, expression levels of certain genes described herein may be used for determining whether a subject is likely to respond to a PD1 inhibitor and/or a CTLA4 inhibitor.

Figure 2C:
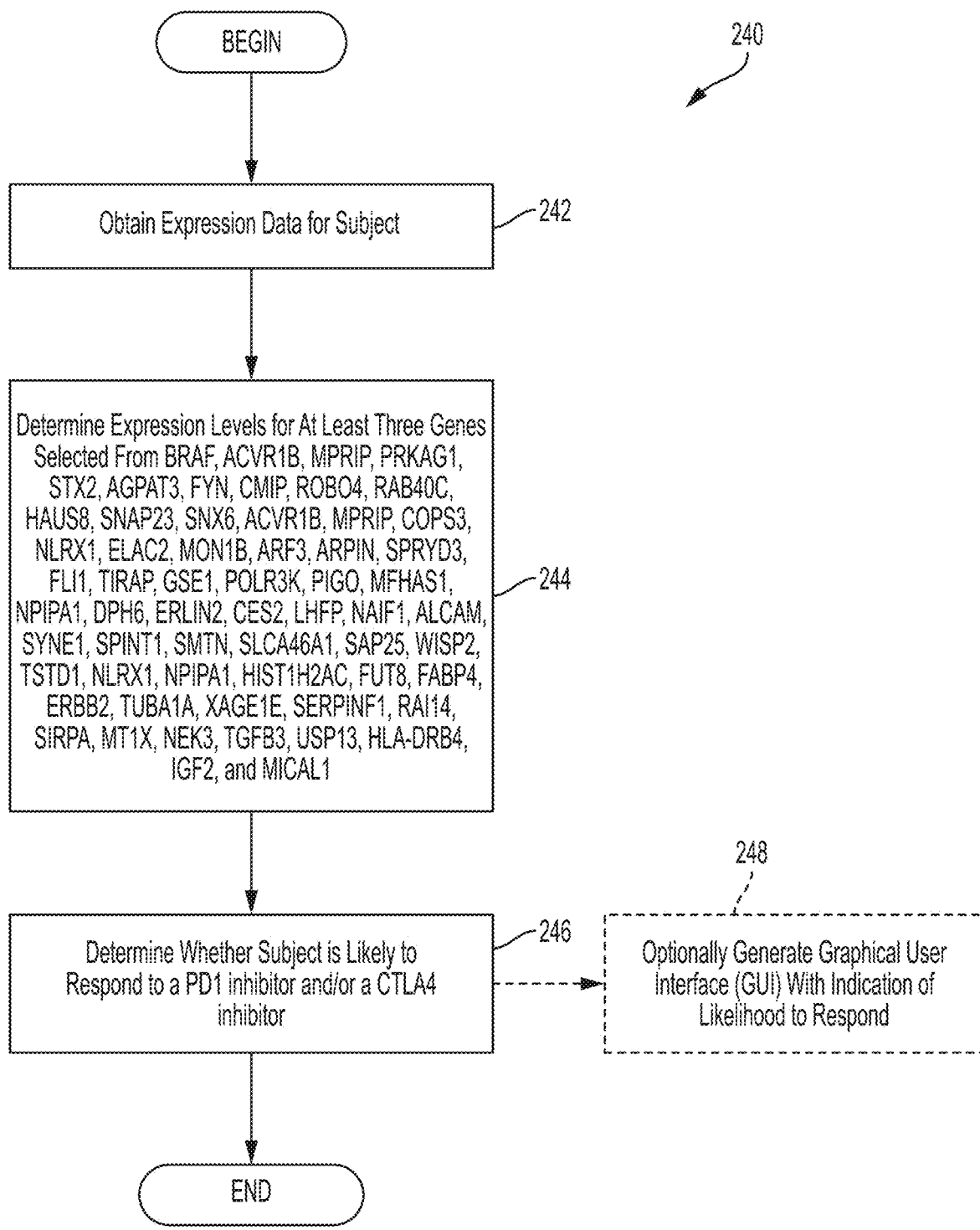
FIG. 2C is a flowchart of an illustrative process for determining whether a subject is likely to respond to a PD1 inhibitor and/or a CTLA4 inhibitor, in accordance with some embodiments of the technology described herein.

FIG. 2C is a flowchart of an illustrative computer-implemented process 240 for determining whether an additional subject is likely to respond positively to a PD1 inhibitor and/or a CTLA4 inhibitor. Process 240 may be used for determining a response to a PD1 inhibitor such as a molecule or antibody that inhibits PD1, PDL1 and/or PDL2, for example, pembrolizumab. Process 240 may also be used for determining a response to a CTLA4 inhibitor such as a molecule or antibody that inhibits CTLA4, for example, ipilimumab or tremelimumab.

Process 240 begins at act 242, wherein expression data for responders and non-responders to a PD1 inhibitor and/or a CTLA4 inhibitor is obtained. Expression data may be obtained from various sources using any suitable means as described in further detail in section "Obtaining Expression Data". As described above, expression data may be obtained from a biological sample of a subject and/or from a database in which such information is stored. For example, RNA expression data, DNA expression data, and protein expression data may be obtained in act 242. Expression data may be obtained for any number of patients and/or for a single patient in need of the analysis provided herein. Further aspects relating to obtaining expression data are provided in section "Obtaining Expression Data".

Next, process 240 proceeds to act 244, where gene expression levels of at least three genes are determined. Expression levels of at least three of the following genes may be determined as described herein: BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAH1.

Expression levels for any combination of 3 genes or any combination of more than 3 genes may be determined including determining expression levels for each gene. An expression level may be an RNA expression level, a DNA expression level, and/or a protein expression level. Gene expression levels for any number of responders and non-responders may be determined as described herein. Further aspects relating to determining gene expression level between responders and non-responders are provided in section "Expression Levels and Expression Level Differences".

Next, process 240 proceeds to act 246, where it is determined whether the subject is likely to respond positively to the PD1 inhibitor and/or the CTLA4 inhibitor based on the at least three determined gene expression levels and a statistical model trained using the expression data. Aspects relating to training the statistical model using expression data have been previously described for FIG. 2A and FIG. 2B. Information relating to a patient's response or lack thereof may be output to a user, in some embodiments, by displaying the information to the user in a graphical user interface (GUI), including the information in a report, sending an email to the user, and/or in any other suitable way.

In this way, a patient can be identified as a responder or non-responder to a PD1 inhibitor and/or a CTLA4 inhibitor based on their gene expression levels. This information may be useful for determining a course of treatment with a PD1 inhibitor and/or CTLA4 inhibitor, and/or for evaluating suitability of a patient for participating in a clinical trial.

Expression Data

Systems and methods described herein are based, at least in part, on the identification of genes that were found to be differentially expressed in responders to an immune checkpoint blockade therapy compared to non-responders to the immune checkpoint blockade therapy. Differential expression of genes indicative of a patient's response to an immune checkpoint blockade therapy or lack thereof may be obtained from patient specific information such as a patient's expression data.

As used herein, the term "expression data" refers to any data indicative of expression of a gene or a product thereof (e.g., RNA and/or protein). In some embodiments, expression data is DNA expression data. In some embodiments, expression data is RNA expression data. In some embodiments, expression data is protein expression data. Expression data may be obtained from a variety of sources as described herein.

Systems and methods described herein, in some embodiments, provide for obtaining expression data for a plurality of genes. In some embodiments, the plurality of genes comprises at least 3 genes. In some embodiments, the plurality of genes comprises at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more genes.

Expression data encompasses expression data for any gene or product thereof. Examples of genes include, but are not limited to, BRAF, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAH1.

Expression data, in some embodiments, is utilized by systems and methods provided herein to predict a patient's response or lack thereof to an immune checkpoint blockade therapy. In some embodiments, expression data is utilized by systems and methods provided herein to predict whether a patient may or may not have one or more adverse reactions to an immune checkpoint blockade therapy.

Expression Levels and Expression Level Differences

Expression data, in some embodiments, may be used for determining an expression level of a gene or product thereof indicative of a patient's response or lack thereof to an immune checkpoint blockade therapy. As used herein, the term "expression level" refers to an expression level of a gene or a product thereof (e.g., RNA and/or protein). Accordingly, an expression level, in some embodiments, may refer to a level of DNA, RNA and/or protein.

An expression level as described herein may be an expression level in a sample obtained from a subject that responded to an immune checkpoint blockade therapy (e.g., a responder) that deviates (e.g., is increased or decreased) when compared to a corresponding expression level in a sample obtained from a subject that was non-responsive to an immune checkpoint blockade therapy (e.g., a non-responder) by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

An expression level of a gene as described herein may be an expression level of a gene in a sample obtained from a subject that responded to an immune checkpoint blockade therapy (e.g., a responder) that deviates (e.g., is increased or decreased) when compared to an expression level of the same gene in a sample obtained from a subject that was non-responsive to an immune checkpoint blockade therapy (e.g., a non-responder) by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

An expression level of DNA as described herein may be an expression level of DNA in a sample obtained from a subject that responded to an immune checkpoint blockade therapy (e.g., a responder) that deviates (e.g., is increased or decreased) when compared to an expression level of the same DNA in a sample obtained from a subject that was non-responsive to an immune checkpoint blockade therapy (e.g., a non-responder) by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

An expression level of RNA as described herein may be an expression level of RNA in a sample obtained from a subject that responded to an immune checkpoint blockade therapy (e.g., a responder) that deviates (e.g., is increased or decreased) when compared to an expression level of the same RNA in a sample obtained from a subject that was non-responsive to an immune checkpoint blockade therapy (e.g., a non-responder) by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

An expression level of a protein as described herein may be an expression level of a protein in a sample obtained from a subject that responded to an immune checkpoint blockade therapy (e.g., a responder) that deviates (e.g., is increased or decreased) when compared to an expression level of the same protein in a sample obtained from a subject that was non-responsive to an immune checkpoint blockade therapy (e.g., a non-responder) by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

Systems and methods described herein provide for obtaining any number of expression levels of a gene or product thereof in a subject (e.g., a responder or a non-responder). In some embodiments, systems and methods described herein provide for obtaining at least one expression level of a gene or product thereof. In some embodiments, systems and methods described herein provide for obtaining at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more expression levels of a gene or product thereof in a subject.

Expression levels may be determined for any number of subjects. In some embodiments, expression levels are determined for at least one subject. In some embodiments, expression levels are determined for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more subjects.

Expression data, in some embodiments, may be used for determining expression level differences for a gene or product thereof indicative of a patient's response or lack thereof to an immune checkpoint blockade therapy. As used herein, the term "expression level differences" refers to an expression level of a gene or a product thereof (e.g., RNA and/or protein) in a responder to an immune checkpoint blockade therapy that differs from an expression level of the gene or product thereof (e.g., RNA and/or protein) in a non-responder to the immune checkpoint blockade therapy. For example, an expression level of a gene or product thereof may have an elevated level or a reduced level in a responder relative to the expression level of the same gene or product thereof in a non-responder by at least 1% (e.g., 2%, 3%, 4%, 5%, 6%, 7%, 8%, 9%, 10%, 15%, 20%, 30%, 40%, 50%, 60%, 70%, 80%, 90%, 100%, 2-fold, 5-fold, 10-fold, 20-fold, 50-fold, 100-fold or more).

An expression level difference may be determined by comparing an expression level or a transformed expression level (e.g., a log transformation of a level) of a gene or product thereof in a responder to that of a non-responder and vice versa. In some embodiments, an expression level difference is determined by comparing an expression level of a gene or product thereof or a transformed expression level (e.g., a log transformation of a level) of a gene or product thereof in a responder to that of a non-responder. In some embodiments, an expression level difference is determined by comparing an expression level of a gene or product thereof or a transformed expression level (e.g., a log transformation of a level) of a gene or product thereof in a non-responder to that of a responder.

Systems and methods described herein provide for determining any number of expression level differences between a responder and non-responder. In some embodiments, systems and methods described herein provide for determining at least one expression level difference between a responder and non-responder. In some embodiments, systems and methods described herein provide for obtaining at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more expression level differences between a responder and non-responder.

In some embodiments, expression level differences may be determined for each subject in a plurality of subjects. As used herein, the term "a plurality of subjects" refers to a group of subjects having responders to an immune checkpoint blockade therapy and non-responders to the immune checkpoint blockade therapy. A plurality of subjects is not limited in number of responders to an immune checkpoint blockade therapy and/or number of non-responders to the immune checkpoint blockade therapy.

In some embodiments, a plurality of subjects comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more responders to an immune checkpoint blockade therapy.

In some embodiments, a plurality of subjects comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more non-responders to an immune checkpoint blockade therapy.

Systems and methods described herein provide for identifying a subset of genes associated with an immune checkpoint blockade therapy using determined expression level differences. In some embodiments, identifying the subset of genes associated with an immune checkpoint blockade therapy comprises identifying genes that are differentially expressed between responders and non-responders with at least a threshold level of statistical significance.

Any number of genes may be included in a subset of genes associated with an immune checkpoint blockade therapy. In some embodiments, a subset of genes associated with an immune checkpoint blockade therapy comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 200, at least 300, at least 400, at least 500, at least 1000, at least 2000, at least 3000, at least 4000, at least 5000, at least 10000, at least 100000, or more genes.

A threshold level, in some embodiments, can be a predetermined level. Such a predetermined level can represent an expression level in responders or in non-responders. The predetermined level can take a variety of forms. For example, it can be a single cut-off value, such as a median or mean. In some embodiments, a predetermined level can be established based upon comparison of expression levels in responders to those in non-responders. Alternatively, the predetermined level can be a range including, for example, a range representing expression levels in responders or non-responders.

Systems and methods described herein provide for obtaining additional expression data for an additional subject. As used herein, the term "additional expression data" refers to expression data of a single additional subject that is not a subject in the plurality of subjects having responders to an immune checkpoint blockade therapy and non-responders to the immune checkpoint blockade therapy. Using additional expression data and a statistical model, systems and methods described herein provide for determining the additional subject's response or lack thereof to an immune checkpoint blockade therapy.

Statistical Model

Aspects of the present disclosure provide system and methods that relate to a statistical model for predicting efficacy of an immune checkpoint blockade therapy using expression data.

Training a statistical model may be accomplished using various techniques. In some embodiments, training the statistical model comprises training a generalized linear model having a plurality of regression variables. In some embodiments, training the statistical model comprises training a logistic regression model having a plurality of regression variables. In some embodiments, training the statistical model comprises iteratively adding regression variables for respective genes to the statistical model.

A logistic regression model, in some embodiments, comprises a respective plurality of weights for the plurality of regression variables, wherein estimating the parameters of the statistical model comprises estimating the plurality of weights using the expression data for the plurality of subjects and information indicating which of the plurality of subjects responded to the immune checkpoint blockade therapy and/or which of the plurality of subjects did not respond to the immune checkpoint blockade therapy.

Iteratively adding regression variables, in some embodiments, comprises identifying a candidate gene in the subset of genes; augmenting a current statistical model with a regression variable for the candidate gene to obtain an augmented statistical model; evaluating performance of the augmented statistical model; and determining to add the regression variable for the candidate gene to the current statistical model based on results of evaluating the performance. In some embodiments, evaluating performance of the augmented statistical model comprises obtaining an area under a receiver operating characteristic curve (ROC AUC) statistic.

Different groups of regression variables may be used when training the statistical model. In some embodiments, the group of regression variables includes a regression variable for each of a predictor set of genes. In some embodiments, each of the group of regression variables represents a ratio of a pair of genes for respective pairs of members of the predictor set of genes. As used herein, the term "subset of genes associated with a checkpoint blockade therapy" refers to a set of genes for which expression levels and/or expression level differences indicate a response or lack thereof to an immune checkpoint blockade therapy. As used herein, the term "predictor set of genes" is a set of genes selected from the subset of genes associated with a checkpoint blockade therapy for use in a statistical model for predicting response or lack thereof to an immune checkpoint therapy as described herein.

A predictor set of genes may comprise any number of genes. In some embodiments, the predictor set of genes comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, or more genes. A predictor set of genes may comprise any number of genes. In some embodiments, the predictor set of genes comprises up to 6, up to 7, up to 8, up to 9, up to 10, up to 11, up to 12, up to 13, up to 14, up to 15, up to 16, up to 17, up to 18, up to 19, up to 20, up to 25, up to 30, up to 40, or up to 50 genes.

In some embodiments, the predictor set of genes includes at least 2 (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) of the group of genes consisting of: BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the predictor set of genes includes at least 2 (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the group of genes consisting of: BRAF, PRKAG1, STX2, AGPAT3, FYN, CMIP, ROBO4, RAB40C, HAUS8, SNAP23, SNX6, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the predictor set of genes comprises BRAF, PRKAG1, STX2, AGPAT3, FYN, CMIP, ROBO4, RAB40C, HAUS8, SNAP23, SNX6, XAGE1E, SERPINF1, RAI14, SIRPA, MT1X, NEK3, TGFB3, USP13, HLA-DRB4, IGF2, and MICAL1.

In some embodiments, the predictor set of genes consists of XAGE1E, SERPINF1, RAI14, SIRPA, MT1X, NEK3, TGFB3, USP13, HLA-DRB4, IGF2, and MICAL1.

A statistical model as described herein may comprise one or more sets of dependent variables. In some embodiments, the statistical model comprises a first set of dependent variables each representing a ratio of a pair of genes.

Any number of ratios may be used in systems and methods described herein. In some embodiments, the ratios comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 or more ratios. In some embodiments, the ratios comprise up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, or up to 30 ratios.

In some embodiments, the genes are selected from BRAF, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAH1.

In some embodiments, the genes are selected from BRAF, PRKAG1, STX2, AGPAT3, FYN, CMIP, ROBO4, RAB40C, HAUS8, SNAP23, SNX6, XAGE1E, SERPINF1, RAI14, SIRPA, MT1X, NEK3, TGFB3, USP13, HLA-DRB4, IGF2, and MICAL1. In some embodiments, the genes comprise BRAF, RAI14, PRKAG1, STX2, AGPAT3, FYN, CMIP, ROBO4, RAB40C, HAUS8, SNAP23, and SNX6. In some embodiments, the genes consist of BRAF, RAI14, PRKAG1, STX2, AGPAT3, FYN, CMIP, ROBO4, RAB40C, HAUS8, SNAP23, and SNX6.

In some embodiments, the at least two (e.g., 3, 4, 5, 6, 7, 8, 9, 10, 11, 12, 13, 14, 15, 16, 17, 18, 19, or 20) gene ratios are selected from BRAF:RAI14, ACVR1B:MPRIP, ACVR1B:COPS3, PRKAG1:STX2, NLRX1:ELAC2, MON1B:STX2, ARF3:MPRIP, ARPIN:MPRIP, SPRYD3:FLI1, TIRAP:MPRIP, GSE1:RAI14, POLR3K:HAUS8, RAB40C:HAUS8, PIGO:MPRIP, MFHAS1:USP13, GSE1:NPIPA1, DPH6:STX2, ERLIN2:RAI14, CES2:LHFP, and NAIF1:HAUS8.

In some embodiments, the at least two (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, 150, 155, 160, 165, 170, 175, 180, 185, 190, or 200) gene ratios are selected from MON1B:STX2, FAM234A:LIN37, DPH6:STX2, BRAF:RAI14, ADCK2:C14ORF80, POLR3K:HAUS8, URB1:TMEM181, GCLC:NEK3, RAB40C:HAUS8, NLRX1:ELAC2, CMIP:ROBO4, NXT2:FBXO5, EIF3H:NEK3, EHHADH:SNX6, DMTN:RASD1, SLC46A1:RBM8A, ACVR1B:GTF2H2, NPEPPS:HDAC2, CXCL16:BASP1, MFHAS1:DYRK3, ACVR1B:USP13, DPH6:C14ORF166, CES2:LHFP, ACVR1B:DCP1B, NAIF1:HDGFRP2, ABCC1:TRIO, GPR107:STX2, ZDHHC7:USP13, PRKAG1:TSEN2, PC:HAUS8, LRBA:CEP192, POM121C:CNPY4, KAT14:SETD5, SLC35A5:SNX6, ATP6V1A:GTDC1, TXNL4B:AKAP8L, SLC36A1:HAUS8, PSAP:SH3BP5, CMIP:OLFML2B, TATDN3:NEK3, TASP1:DDX5, SDC4:FUT8, TMEM254:COPS3, ARF3:MPRIP, SLC46A1:PMF1-BGLAP, ATP6V1A:FBXO30, MFHAS1:C2CD5, ERAP1:SYNE1, F11R:FYN, RCHY1:RNF146, ATP6V1A:PDCD5, ACVR1B:ELAC2, CLN3:HAUS8, NAIF1:HAUS8, PRKAG1:SOCS4, HNRNPH2:USP13, TPD52:MTRF1L, ACVR1B:C14ORF80, IST1:NPIPA1, DPH6:TCEAL1, CSNK2A1:MRGBP, CXCL16:FILIP1L, AGK:USP13, MYO18A:FYN, SIRPA:FLII, C16ORF58:FLII, TRIM11:AKAP8L, MFHAS1:DMPK, JMJD8:AKAP8L, DIAPH1:SYNE1, BCKDHA:HAUS8, TMEM254:PSMC5, ACVR1B: HTRA2, MON1B:SYNE1, DCAKD:PMF1-BGLAP, VWA5A:RASD1, TPD52:TRA2A, ZMIZ1:STX2, NUB1: C2CD5, GSE1:RAI14, AGFG1:STX2, NXT2:TRA2A, ACSS1:NPIPA5, FBXW8:USP13, CMIP:TRIO, AGPAT3: FYN, PSMF1:PTOV1, CREG1:TARS, SLC46A1:CEP131, SIRPA:SERPINTF1, DNAJA2:HDAC2, ERLIN2:RAI14, FAM234A:ZNF428, CHMP1A:LIN37, FAM110A:TCF7, ACVR1B:COPS3, GSE1:DDX11, CREG1:ARFGAP3, BRPF3:USP13, MFHAS1:USP13, LAMP1:MAPK7, ACSS1:PMF1-BGLAP, SUFU:TRIO, ARF3:DAD1, NLRX1:TRA2A, NLRX1:SLC39A13, CMIP:SH3BP5, PPIF:HAUS8, ANKRD13A:SOCS4, F8:SYNE1, ATP6V1A:USP48, ACVR1B:MPRIP, TMEM141:HAUS8, TIRAP:MPRIP, ZDHHC12:HAUS8, SLC46A1:MED9, MFHAS1:NCAPD2, ERBB2:CENPL, JMJD7:PQBP1, PHKG2:AKAP8L, SLC36A1:SLC26A6, ATP6V1A: SPDL1, DCTN5:CEP89, IPPK:STX2, LAMB3:ADM, ARPIN:MPRIP, SLC46A1:FYN, ACVR1B:LTV1, GDE1: ZNF576, DMTN:GFPT2, LCMT2:RDH11, ACVR1B: CCDC66, ACVR1B:NEK3, SEC24B:MAP3K7, ZNF764: AKAP8L, CHMP1A:HAUS8, PIGO:USP13, ARF3: MAPK7, GSE1:CCDC66, ACVR1B:METTL17, C200RF196:HAUS8, ARF3:CBY1, BRPF3:MPRIP, SLC46A1:PSMC5, CMTR2:MAP3K7, TASP1:CCDC66, BRPF3:PIP5K1A, PIGO:FLII, MYO18A:ACIN1, PSMF1: AKAP8L, FBXW11:LTV1, CXCL16:ADAMTS2, SPRYD3:FLII, DPH6:FRA10AC1, PDXK:HAUS8, ACVR1B:WDR45B, MON1B:SMIM10L1, LAT:PRRX1, WDR24:AKAP8L, EHHADH:CCDC174, ACVR1B: CEP89, MFHAS1:ODF2, ALDH6A1:GOPC, GSE1: NBPF14, EHHADH:MEX3C, BRPF3:STX2, EHHADH: GTF2H2, PIGO:MPRIP, PRKAG1:STX2, EHHADH: SMIM10L1, SLC36A1:SH3PXD2A, ADCK2:STX2, SORD:PDCD5, ACVR1B:LLGL1, LAMTOR3:ZNF644, PIM1:MICAL2, CREG1:NPIPA1, GSE1:NPIPA1, PRR13: HAUS8, WDR55:RAD1, CMIP:NID2, DIAPH1:TARS, SNAP23:SNX6, GSE1:TSPYL2, C2ORF68:NPIPA1, MFHAS1:TRIO, DPH6:CGRRF1, KIF13B:STX2, PTK2B: TCF7, ATP2A2:STX2, ANKS1A:USP13, JRK:NEK3, LRBA:DDX5, IDH2:HAUS8, CCNF:HAUS8, CMIP: CHN1, STAU2:STX2, ACSS1:LHFP, GSR:STX2, IGF2R: FYN, CXCL16:ACVRL1.

In some embodiments, the ratios consists of BRAF: RAI14, PRKAG1:STX2, AGPAT3:FYN, CMIP:ROBO4, RAB40C:HAUS8, SNAP23:SNX6.

Obtaining Expression Data

Expression data as described herein may be obtained from a variety of sources. In some embodiments, expression data may be obtained by analyzing a biological sample from a patient. The biological sample may be analyzed prior to performance of the methods described herein for predicting the efficacy of one or more immune checkpoint blockade treatments for the patient. In some such embodiments, data obtained from the biological sample may be stored (e.g., in a database) and accessed during performance of the techniques described herein for predicting the efficacy of one or more treatments for the patient. Accordingly, in some embodiments, expression data is obtained from a database containing expression data for at least one patient.

Biological Samples

Any biological sample from a subject (i.e., a patient or individual) may be analyzed as described herein to obtain expression data. In some embodiments, the biological sample may be any sample from a subject known or suspected of having cancerous cells or pre-cancerous cells.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

The biological sample may be any type of sample including, for example, a sample of a bodily fluid, one or more cells, a piece of tissue, or some or all of an organ. In certain embodiments, one sample will be taken from a subject for analysis. In some embodiments, more than one (e.g., 2, 3, 4, 5, 6, 7, 8, 9, 10, 11, 12, 13, 14, 15, 16, 17, 18, 19, 20, or more) samples may be taken from a subject for analysis. In some embodiments, one sample from a subject will be analyzed. In certain embodiments, more than one (e.g., 2, 3, 4, 5, 6, 7, 8, 9, 10, 11, 12, 13, 14, 15, 16, 17, 18, 19, 20, or more) samples may be analyzed. If more than one sample from a subject is analyzed, the samples may be procured at the same time (e.g., more than one sample may be taken in the same procedure), or the samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure). A second or subsequent sample may be taken or obtained from the same region (e.g., from the same tumor or area of tissue) or a different region (including, e.g., a different tumor). A second or subsequent sample may be taken or obtained from the subject after one or more treatments, and may be taken from the same region or a different region. As an example, the second or subsequent sample may be useful in determining whether the cancer in each sample has different characteristics (e.g., in the case of samples taken from two physically separate tumors in a patient) or whether the cancer has responded to one or more treatments (e.g., in the case of two or more samples from the same tumor or different tumors prior to and subsequent to a treatment).

Any of the biological samples described herein may be obtained from the subject using any known technique. In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, each of the at least one biological samples is a bodily fluid sample, a cell sample, or a tissue biopsy.

In some embodiments, one or more than one cell (i.e., a cell sample) may be obtained from a subject using a scrape or brush method. The cell sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) samples from one or more tumors or tissues known or suspected of having cancerous cells.

Sample Analysis

Systems and methods described herein are based, at least in part, on expression level differences for a plurality of genes of a patient and/or the patient's cancer. Such information may be obtained from a biological sample of the subject (e.g., the patient) as described herein.

Any type of analysis may be performed on a biological sample from a subject. In some embodiments, a blood analysis is performed on a biological sample from a subject. In some embodiments, a cytometry analysis is performed on a biological sample from a subject. In some embodiments, a histological analysis is performed on a biological sample from a subject. In some embodiments, a immunohistological analysis is performed on a biological sample from a subject.

Any type of sequencing data may be obtained from a biological sample of a subject. In some embodiments, the sequencing data is DNA sequencing data. In some embodiments, the sequencing data is RNA sequencing data. In some embodiments, the sequencing data is proteome sequencing data.

Such sequencing data may be obtained by any known technique. In some embodiments, the sequencing data is obtained from whole genome sequencing (WGS). In some embodiments, the sequencing data is obtained from whole exome sequencing (WES). In some embodiments, the sequencing data is obtained from whole transcriptome sequencing. In some embodiments, the sequencing data is obtained from mRNA sequencing. In some embodiments, the sequencing data is obtained from DNA/RNA-hybridization. In some embodiments, the sequencing data is obtained from microarray. In some embodiments, the sequencing data is obtained from DNA/RNA chip. In some embodiments, the sequencing data is obtained from PCR. In some embodiments, the sequencing data is obtained from single nucleotide polymorphism (SNP) genotyping.

Expression data (e.g., indicating expression levels) for a plurality of genes may be obtained from a biological sample. There is no limit to the number of genes which may be examined. For example, there is no limit to the number of genes for which the expression levels may be examined.

As an example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of examples, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be used for any evaluation described herein. As a further set of examples, up to four, up to five, up to six, up to seven, up to eight, up to nine, up to ten, up to eleven, up to twelve, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 40, up to 50, up to 60, up to 70, up to 80, up to 90, up to 100, up to 125, up to 150, up to 175, up to 200, up to 225, up to 250, up to 275, or up to 300 genes may be used for any evaluation described herein.

Any method may be used on a sample from a subject in order to acquire expression data (e.g., indicating expression levels) for the plurality of genes. As a set of examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data for DNA (or gene) expressed in a sample, for example, sequencing data for a gene that is expressed in a patient's sample. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods and systems described herein. As a set of examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

Datasets

Any dataset containing expression data may be used to obtain expression data as described herein. In some embodiments, expression data may be obtained from one or more databases and/or any other suitable electronic repository of data. Examples of databases include, but are not limited to, CGP (Cancer Genome Project), CPTAC (Clinical Proteomic Tumor Analysis Consortium), ICGC (International Cancer Genome Consortium), and TCGA (The Cancer Genome Atlas). In some embodiments, expression data may be obtained from data associated with a clinical trial. In some embodiments, expression data may be predicted in association with a clinical trial based on one or more similar drugs (e.g., drugs of a similar class such as PD-1 inhibitors). In some embodiments, expression data may be obtained from a hospital database. In some embodiments, expression data may be obtained from a commercial sequencing supplier. In some embodiments, expression data may be obtained from a subject (e.g., a patient) and/or a subject's (e.g., a patient's) relative, guardian, or caretaker.

Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a protein in a sample and/or by detecting a level of activity of a protein in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of a protein may be measured using an immunoassay. Examples of immunoassays include any known assay (without limitation), and may include any of the following: immunoblotting assay (e.g., Western blot), immunohistochemical analysis, flow cytometry assay, immunofluorescence assay (IF), enzyme linked immunosorbent assays (ELIS As) (e.g., sandwich ELISAs), radioimmunoas says, electrochemiluminescence-based detection assays, magnetic immunoassays, lateral flow assays, and related techniques. Additional suitable immunoassays for detecting a level of a protein provided herein will be apparent to those of skill in the art.

Such immunoassays may involve the use of an agent (e.g., an antibody) specific to the target protein. An agent such as an antibody that "specifically binds" to a target protein is a term well understood in the art, and methods to determine such specific binding are also well known in the art. An antibody is said to exhibit "specific binding" if it reacts or associates more frequently, more rapidly, with greater duration and/or with greater affinity with a particular target protein than it does with alternative proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen. In some embodiments, a sample may be contacted, simultaneously or sequentially, with more than one binding agent that binds different proteins (e.g., multiplexed analysis).

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source including, but not limited to, primate (human and non-human primate) and primatized (such as humanized) antibodies.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., (3-galactosidase) that produces a colored product from a colorless substrate.

It will be apparent to those of skill in the art that this disclosure is not limited to immunoassays. Detection assays that are not based on an antibody, such as mass spectrometry, are also useful for the detection and/or quantification of a protein and/or a level of protein as provided herein. Assays that rely on a chromogenic substrate can also be useful for the detection and/or quantification of a protein and/or a level of protein as provided herein.

Alternatively, the level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Genes

The various genes recited herein are, in general, named using human gene naming conventions. The various genes, in some embodiments, are described in publically available resources such as published journal articles. The gene names may be correlated with additional information (including sequence information) through use of, for example, the NCBI GENBANK® databases available at www <dot> ncbi <dot> nlm <dot> nih <dot> gov; the HUGO (Human Genome Organization) Gene Nomination Committee (HGNC) databases available at www <dot> genenames <dot> org; the DAVID Bioinformatics Resource available at www <dot> david <dot> ncifcrf <dot> gov. It should be appreciated that a gene may encompass all variants of that gene. For organisms or subjects other than human subjects, corresponding specific-specific genes may be used. Synonyms, equivalents, and closely related genes (including genes from other organisms) may be identified using similar databases including the NCBI GENBANK® databases described above.

In some embodiments, gene BRAF may be identified as GENBANK® Accession number NM_004333.5 or NR_148928.1 or NM_001354609.1; gene PRKAG1 may be identified as GENBANK® Accession number NM_001206710.1 or NM_001206709.1 or NM_002733.4; gene STX2 may be identified as GENBANK® Accession number NM_194356.3 or NM_001351049.1 or NM_001351052.1 or NM_001980.4 or NM_001351051.1 or NM_001351050.1; gene AGPAT3 may be identified as GENBANK® Accession number NM_020132.4 or NM_001037553.1; gene FYN may be identified as GENBANK® Accession number NM_153047.3 or NM_153048.3 or NM_002037.5; gene CMIP may be identified as GENBANK® Accession number NM_198390.2 or NM_030629.2; gene ROBO4 may be identified as GENBANK® Accession number NM_001301088.1 or NM_019055.5; gene RAB40C may be identified as GENBANK® Accession number NM_001172666.1 or NM_001172665.1 or NM_001172664.1 or NM_001172663.1 or NM_021168.4; gene HAUS8 may be identified as GENBANK® Accession number NM_001011699.1 or NM_033417.1; gene SNAP23 may be identified as GENBANK® Accession number NM_130798.2 or NM_003825.3; gene SNX6 may be identified as GENBANK® Accession number NM_152233.3 or NM_021249.4; gene ACVR1B may be identified as GENBANK® Accession number NM_020328.3 or NM_004302.4 or NM_020327.3; gene MPRIP may be identified as GENBANK® Accession number NM_015134.3 or NM_201274.3; gene COPS3 may be identified as GENBANK® Accession number NM_003653.3 or NM_001199125.1 or NM_001316354.1 or NM_001316355.1 or NM_001316356.1 or NM_001316357.1 or NM_001316358.1; gene NLRX1 may be identified as GENBANK® Accession number NM_001282358.1 or NM_001282144.1 or NM_024618.3 or NM_001282143.1; gene ELAC2 may be identified as GENBANK® Accession number NM_173717.1 or NM_001165962.1 or NM_018127.6; gene MON1B may be identified as GENBANK® Accession number NM_001286640.1 or NM_001286639.1 or NM_014940.3; gene ARF3 may be identified as GENBANK® Accession number NM_001659.2; gene ARPIN may be identified as GENBANK® Accession number NM_001282380.1 or NM_182616.3; gene SPRYD3 may be identified as GENBANK® Accession number NM_032840.2; gene FLI1 may be identified as GENBANK® Accession number NM_001271012.1 or NM_001271010.1 or NM_002017.4 or NM_001167681.2; gene TIRAP may be identified as GENBANK® Accession number NM_001318776.1 or NM_001318777.1 or NM_148910.2 or NM_001039661.1; gene GSE1 may be identified as GENBANK® Accession number NM_014615.4 or NM_001278184.2 or NM_001134473.2; gene POLR3K may be identified as GENBANK® Accession number NM_016310.4; gene PIGO may be identified as GENBANK® Accession number NM_001201484.1 or NM_152850.3 or NM_032634.3; gene MFHAS1 may be identified as GENBANK® Accession number NM_004225.2; gene NPIPA1 may be identified as GENBANK® Accession number NM_006985.3; gene DPH6 may be identified as GENBANK® Accession number NM_001141972.1 or NM_080650.3; gene ERLIN2 may be identified as GENBANK® Accession number NM_001362880.1 or NM_001362878.1 or NM_007175.7 or NM_001003790.3 or NM_001003791.2; gene CES2 may be identified as GENBANK® Accession number NM_198061.2 or NR_036684.1 or NM_003869.5; gene LHFP may be identified as GENBANK® Accession number NM_005780.2; gene NAIF1 may be identified as GENBANK® Accession number NM_197956.3; gene ALCAM may be identified as GENBANK® Accession number NM_001243283.1 or NM_001243281.1 or NM_001243280.1 or NM_001627.3; gene SYNE1 may be identified as GENBANK® Accession number NM_001347702.1 or NM_001347701.1 or NM_033071.3 or NM_182961.3; gene SPINT1 may be identified as GENBANK® Accession number NM_001032367.1 or NM_003710.3 or NM_181642.2; gene SMTN may be identified as GENBANK® Accession number NM_001207018.1 or NM_001207017.1 or NM_134270.2 or NM_134269.2 or NM_006932.4; gene SLCA46A1 may be identified as GENBANK® Accession number NM_001242366.2 or NM_080669.5; gene SAP25 may be identified as GENBANK® Accession number NM_001168682.2 or NM_001348680.1 or NM_001348677.1; gene WISP2 may be identified as GENBANK® Accession number NM_001323369.1 or NM_001323370.1 or NM_003881.3; gene TSTD1 may be identified as GENBANK® Accession number NM_001113207.1 or NM_001113206.1 or NM_001113205.1; gene HIST1H2AC may be identified as GENBANK® Accession number NM_003512.3; gene FUT8 may be identified as GENBANK® Accession number NM_178155.2 or NM_178156.2 or NM_004480.4; gene FABP4 may be identified as GENBANK® Accession number NM_001442.2; gene ERBB2 may be identified as GENBANK® Accession number NR_110535.1 or NM_001289938.1 or NM_001289937.1 or NM_001289937.1 or NM_001005862.2 or NM_004448.3; gene TUBA1A may be identified as GENBANK® Accession number NM_001270400.1 or NM_001270399.1 or NM_006009.3; gene XAGE1E may be identified as GENBANK® Accession number NM_001097605.2 or NM_001097604.2; gene SERPINF1 may be identified as GENBANK® Accession number NM_001329905.1 or NM_001329904.1 or NM_001329903.1 or NM_002615.6; gene RAI14 may be identified as GENBANK® Accession number NM_001145525.1 or NM_001145523.1 or NM_001145522.1 or NM_001145521.1 or NM_001145520.1 or NM_015577.2; gene SIRPA may be identified as GENBANK® Accession number NM_001330728.1 or NM_080792.2 or NM_001040023.1 or NM_001040022.1; gene MT1X may be identified as GENBANK® Accession number NM_005952.3; gene NEK3 may be identified as GENBANK® Accession number NM_152720.2 or NM_001146099.1 or NM_002498.2; gene TGFB3 may be identified as GENBANK® Accession number NM_003239.4 or NM_001329939.1 or NM_001329938.1; gene USP13 may be identified as GENBANK® Accession number NM_003940.2; gene HLA-DRB4 may be identified as GENBANK® Accession number NM_021983.4; gene IGF2 may be identified as GENBANK® Accession number NM_001291862.2 or NM_001291861.2 or NM_001127598.2 or NM_001007139.5 or NM_000612.5; gene MICAL1 may be identified as GENBANK® Accession number NM_001286613.1 or NM_001159291.1 or NM_022765.3.

Immune Checkpoint Blockade Therapy

In certain methods or systems described herein, no recommendation is made regarding administration of an immune checkpoint blockade therapy to a subject (e.g., a human). In certain methods described herein, an immune checkpoint blockade therapy described herein may not be recommended for administration to a subject (e.g., a human). In certain methods described herein, an immune checkpoint blockade therapy described herein may be recommended for administration to a subject (e.g., a human).

In certain methods described herein, an effective amount of an immune checkpoint blockade therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. The subject to be treated by the methods described herein may be a mammal (e.g., may be a human). Mammals may include, but are not limited to: farm animals (e.g., livestock), sport animals, laboratory animals, pets, primates, horses, dogs, cats, mice, and rats.

A subject having a cancer may be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer may be a subject having one or more of the risk factors for that disorder. For example, risk factors associated with cancer include, but are not limited to, (a) viral infection (e.g., herpes virus infection), (b) age, (c) family history, (d) heavy alcohol consumption, (e) obesity, and (f) tobacco use.

Any immune checkpoint blockade therapy may be used in conjunction with the methods and systems described herein. In some embodiments, the immune checkpoint blockade therapy targets Programmed Death 1 (PD1) or a ligand of PD1 such as PDL1 and/or PDL2.

In some embodiments, the immune checkpoint blockade therapy is a molecule that inhibits PD1. In some embodiments, the immune checkpoint blockade therapy is a molecule that inhibits PDL1. In some embodiments, the immune checkpoint blockade therapy is a molecule that inhibits PDL2.

A molecule that inhibits PD1, PDL1 and/or PDL2, in some embodiments, is an antibody or antigen binding fragment thereof. Examples of a molecule that inhibits PD1, PDL1 and/or PDL2 include, but are not limited to, atezolizumab, avelumab, durvalumab, nivolumab, pembrolizumab, pidilizumab, BGB-A317, BMS-936559, or analogs, derivatives, fragments, or salts thereof.

In some embodiments, the immune checkpoint blockade therapy targets cytotoxic T lymphocyte antigen 4 (CTLA4) or a ligand of CTLA4 such as CD80 and/or CD86. In some embodiments, the immune checkpoint blockade therapy is a molecule that inhibits CTLA4. In some embodiments, the immune checkpoint blockade therapy is a molecule that inhibits CD80. In some embodiments, the immune checkpoint blockade therapy is a molecule that inhibits CD86.

A molecule that inhibits CTLA4, CD80 and/or CD86, in some embodiments, is an antibody or antigen binding fragment thereof. Examples of a molecule that inhibits CTLA4, CD80 and/or CD86 include, but are not limited to, ipilimumab or tremelimumab.

An immune checkpoint blockade therapy as described herein may have targets other than PD1 and/or CTLA4 and their ligands. In some embodiments, the immune checkpoint blockade therapy targets lymphocyte activating gene 3 (LAG-3, CD223) or a ligand thereof. In some embodiments, the immune checkpoint blockade therapy targets killer inhibitory receptors (e.g., KIR2DL-1, KIR2DL-2, and KIR2DL-3) or a ligand thereof. In some embodiments, the immune checkpoint blockade therapy targets B7-H3 (CD276) or a ligand thereof. In some embodiments, the immune checkpoint blockade therapy targets T cell immunoglobulin and mucin3 (TIM-3) or a ligand thereof. In some embodiments, the immune checkpoint blockade therapy targets V-domain Ig-containing suppressor of T cell activation (VISTA) or a ligand thereof. In some embodiments, the immune checkpoint blockade therapy targets T cell ITIM Domain (TIGIT) or a ligand thereof. In some embodiments, the immune checkpoint blockade therapy targets immune inhibitory enzyme (IDO) or a ligand thereof.

"An effective amount" as used herein refers to the amount of each active agent (e.g., an immune checkpoint blockade therapy) required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient or clinician may insist upon a lower dose or tolerable dose for medical reasons, psychological reasons, or for virtually any other reason(s).

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an immune checkpoint therapeutic agent may be appropriate. Various formulations and devices for achieving sustained release are known in the art.

In some embodiments, dosages for an immune checkpoint therapeutic agent as described herein may be determined empirically in individuals who have been administered one or more doses of the immune checkpoint therapeutic agent. Individuals may be administered incremental dosages of the immune checkpoint therapeutic agent. To assess efficacy of an administered immune checkpoint therapeutic agent, one or more aspects of a cancer (e.g., tumor formation or tumor growth) may be analyzed.

Generally, for administration of any of the immune checkpoint antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays and/or by monitoring the progress of the disease or cancer as described herein. The dosing regimen (including the therapeutic used) may vary over time.

When the immune checkpoint therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an immune checkpoint therapeutic agent will depend on the specific immune checkpoint therapeutic agent(s) (or compositions thereof) employed, the type and severity of cancer, whether the immune checkpoint therapeutic agent is administered for preventive or therapeutic purposes, previous therapy, the patient's clinical history and response to the immune checkpoint therapeutic agent, and the discretion of the attending physician. Typically the clinician will administer an immune checkpoint therapeutic agent, such as an antibody, until a dosage is reached that achieves the desired result.

Administration of an immune checkpoint therapeutic agent can be continuous or intermittent, depending, for example, upon the recipient's physiological condition, whether the purpose of the administration is therapeutic or prophylactic, and other factors known to skilled practitioners. The administration of an immune checkpoint therapeutic agent (e.g., a PD1 inhibitor) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer. In some embodiments, the methods and systems herein may comprise recommendation of a treatment rather than treatment itself. In some embodiments, no recommendation of a treatment will be made. In certain embodiments, a subject (e.g., a patient) may be identified as a "responder" to one or more immune checkpoint therapies if the subject is predicted to likely respond positively to such treatment. In certain embodiments, a subject (e.g., a patient) may be identified as a "non-responder" to one or more immune checkpoint therapies if the subject is predicted to not likely respond positively to such treatment. In some embodiments, information about an immune checkpoint blockade therapy for a patient will be outputted. In specific embodiments, such information may be outputted to a user (e.g., a doctor or clinician).

Alleviating a cancer includes delaying the development or progression of the disease, or reducing disease severity (e.g., by at least one parameter). Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development or progress of a disease, or delays the onset of one or more complications of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively or in addition to the clinical techniques known in the art, development of the disease may be detectable and assessed based on biomarkers described herein. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the immune checkpoint therapeutic agent (e.g., an antibody) described herein is administered to a subject in need of the treatment at an amount sufficient to reduce cancer (e.g., tumor) growth by at least 10% (e.g., 20%, 30%, 40%, 50%, 60%, 70%, 80%, 90% or greater). In some embodiments, the immune checkpoint therapeutic agent (e.g., an antibody) described herein is administered to a subject in need of the treatment at an amount sufficient to reduce cancer cell number or tumor size by at least 10% (e.g., 20%, 30%, 40%, 50%, 60%, 70%, 80%, 90% or more). In other embodiments, the immune checkpoint therapeutic agent is administered in an amount effective in altering cancer type (e.g., from a more severe to a less severe type; or from a worse prognosis to a better prognosis). Alternatively, the immune checkpoint therapeutic agent is administered in an amount effective in reducing tumor formation, size, or metastasis.

Conventional methods, known to those of ordinary skill in the art of medicine, may be used to administer the immune checkpoint therapeutic agent to the subject, depending upon the type of disease to be treated or the site of the disease. The immune checkpoint therapeutic agent can also be administered via other conventional routes, e.g., administered orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, an immune checkpoint therapeutic agent may be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (e.g., glycerol, propylene glycol, liquid polyethylene glycol, and the like). For intravenous injection, water soluble immune checkpoint therapeutic agents can be administered by the drip method, whereby a pharmaceutical formulation containing the antibody and a physiologically acceptable excipients is infused. Physiologically acceptable excipients may include, for example, 5% dextrose, 0.9% saline, Ringer's solution, and/or other suitable excipients. Intramuscular preparations, e.g., a sterile formulation of a suitable soluble salt form of the immune checkpoint therapeutic agent, can be dissolved and administered in a pharmaceutical excipient such as Water-for-Injection, 0.9% saline, and/or 5% glucose solution.

In one embodiment, an immune checkpoint therapeutic agent is administered via site-specific or targeted local delivery techniques. Examples of site-specific or targeted local delivery techniques include various implantable depot sources of the agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, the contents of each of which are incorporated by reference herein for this purpose.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., *Gene Therapeutics: Methods And Applications Of Direct Gene Transfer* (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. The contents of each of the foregoing are incorporated by reference herein for this purpose.

Therapeutic compositions containing a polynucleotide may be administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

Therapeutic polynucleotides and polypeptides can be delivered using gene delivery vehicles. The gene delivery vehicle can be of viral or non-viral origin (e.g., Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). The contents of each of the foregoing are incorporated by reference herein for this purpose. Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. The contents of each of the foregoing are incorporated by reference herein for this purpose.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581. The contents of each of the foregoing are incorporated by reference herein for this purpose.

It is also apparent that an expression vector can be used to direct expression of any of the protein-based immune checkpoint therapeutic agents (e.g., an immune checkpoint antibody). For example, peptide inhibitors that are capable of blocking (from partial to complete blocking) a cancer causing biological activity are known in the art.

In some embodiments, more than one immune checkpoint therapeutic agents, such as an antibody and a small molecule inhibitory compound, may be administered to a subject in need of the treatment. The agents may be of the same type or different types from each other. At least one, at least two, at least three, at least four, or at least five different agents may be co-administered. Generally immune checkpoint therapeutic agents for administration have complementary activities that do not adversely affect each other. Immune checkpoint therapeutic agents may also be used in conjunction with other agents that serve to enhance and/or complement the effectiveness of the agents.

Treatment efficacy can be predicted as described herein for a patient prior to a treatment. Alternatively or in addition to, treatment efficacy can be predicted and/or determined as described herein over the course of treatment (e.g., before, during, and after treatment). See, e.g., Example 3 below.

Combination Therapy

Compared to monotherapies, combinations of treatment approaches showed higher efficacy in many studies, but the choice of remedies to be combined and designing the combination therapy regimen remain speculative. Given that the number of possible combinations is now extremely high, there is great need for a tool that would help to select drugs and combinations of remedies based on objective information about a particular patient. Use of gene expression data as described herein for designing or electing a specific combination therapy establishes a scientific basis for choosing the optimal combination of preparations.

As noted above, also provided herein are methods of treating a cancer or recommending treating a cancer using any combination of immune checkpoint therapeutic agents or one or more anti-cancer therapeutic agents (e.g., chemotherapy) and one or more additional therapies (e.g., surgery and/or radiotherapy). The term combination therapy, as used herein, embraces administration of more than one treatment (e.g., an antibody and a small molecule or an antibody and radiotherapy) in a sequential manner, that is, wherein each therapeutic agent is administered at a different time, as well as administration of these therapeutic agents, or at least two of the agents or therapies, in a substantially simultaneous manner.

Sequential or substantially simultaneous administration of each agent or therapy can be affected by any appropriate route including, but not limited to, oral routes, intravenous routes, intramuscular, subcutaneous routes, and direct absorption through mucous membrane tissues. The agents or therapies can be administered by the same route or by different routes. For example, a first agent (e.g., a small molecule) can be administered orally, and a second agent (e.g., an antibody) can be administered intravenously.

As used herein, the term "sequential" means, unless otherwise specified, characterized by a regular sequence or order, e.g., if a dosage regimen includes the administration of an antibody and a small molecule, a sequential dosage regimen could include administration of the antibody before, simultaneously, substantially simultaneously, or after administration of the small molecule, but both agents will be administered in a regular sequence or order. The term "separate" means, unless otherwise specified, to keep apart one from the other. The term "simultaneously" means, unless otherwise specified, happening or done at the same time, i.e., the agents are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents or therapies described herein.

Combination therapy can also embrace the administration of the anti-cancer therapeutic agent (e.g., an antibody) in further combination with other biologically active ingredients (e.g., a vitamin) and non-drug therapies (e.g., surgery or radiotherapy).

It should be appreciated that any combination of anti-cancer therapeutic agents may be used in any sequence for treating a cancer. The combinations described herein may be selected on the basis of a number of factors, which include but are not limited to the effectiveness of altering gene expression data, reducing tumor formation or tumor growth, and/or alleviating at least one symptom associated with the cancer, or the effectiveness for mitigating the side effects of another agent of the combination. For example, a combined therapy as provided herein may reduce any of the side effects associated with each individual members of the combination, for example, a side effect associated with an administered anti-cancer agent.

Any anti-cancer therapy or anti-cancer therapeutic agent may be used in conjunction with an immune checkpoint blockade therapy in the methods and systems described herein. In some embodiments, an anti-cancer therapeutic agent is an antibody, an immunotherapy, a radiation therapy, a surgical therapy, and/or a chemotherapy.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, adoptive cell transfer, therapeutic cancer vaccines, oncolytic virus therapy, T-cell therapy, and immune checkpoint inhibitors.

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); Streptomyces family antibiotics (e.g., Bleomycin, Mitomycin C, Actinomycin, and Plicamycin); and ultraviolet light.

EXAMPLES

In order that the technology described herein may be more fully understood, the following examples are set forth. The examples described in this application are offered to illustrate the systems and methods provided herein and are not to be construed in any way as limiting their scope.

Materials and Methods

Datasets

Transcriptome data was downloaded in FASTQ format from the following repositories: Hugo dataset from SRA study SPR070710; Nathanson dataset from Google Cloud repository provided by authors of Nathanson et al.; SKCM17 dataset from Genomic Data Commons (dbGaP study id phs000178.v8.p7, Table S3); and Van Allen dataset from dbGaP study phs001041.v1.p1.

REFERENCES

Hugo et al., *Genomic and Transcriptomic Features of Response to Anti-PD-1 Therapy in Metastatic Melanoma.* Cell. 165, 35-44 (2016).

Nathanson et al., *Somatic Mutations and Neoepitope Homology in Melanomas Treated with CTLA-4 Blockade.* Cancer Immunol Res. 5(1):84-91 (2017).

Van Allen et al., *Genomic Correlates of Response to CTLA-4 Blockade in Metastatic Melanoma.* Science. 350(6257): 302-22 (2015).

Gene Expression Quantification

Quantification of gene expression was performed using the kallisto tool in TPM (transcripts per million) units. As a reference transcriptome, mRNA sequences of RefSeq release 80 database were used. RefSeq transcript (NM) identifies were mapped to HGNC gene symbols. Expression values were summarized for multiple transcript genes. Expression values were log-transformed to $\log_2(TPM+1)$ (log-transformed expressions).

Kallisto version 0.43.0 in the following command was used to build index: kallisto index -i index.dat refseq_80_NM only.fa. Kallisto version 0.43.0 in the following command was used to quantify transcript expressions: kallisto quant index.dat -o OUTPUT_DIR FASTQFILE_1.fastq.gz FASTQFILE_1.fastq.gz.

Constructing A Predictive Model

Principal component analysis (PCA) was performed on log-transformed expressions of 19,308 genes. Gene expressions were transformed into 10 components space using scipy package. Plots were created using matplotlib and seaborn. Gene expression ratios were calculated using pandas and numpy packages. Logistic regression models were constructed and evaluated by scikitlearn package. Kaplan-Meier curves were produced by lifelines.

Example 1: Evaluating Gene Expression Datasets

Figure 3A:
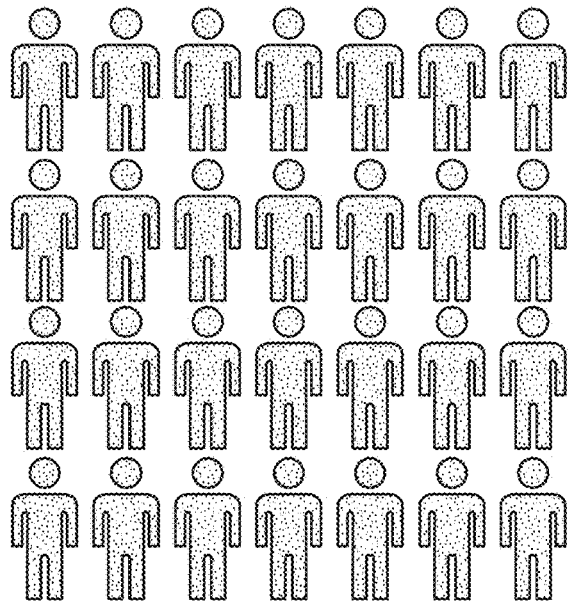
FIG. 3A is a graphic illustrating datasets of melanoma patient cohorts treated with an immune checkpoint blockade therapy, in accordance with some embodiments of the technology described herein.
Figure 3A:
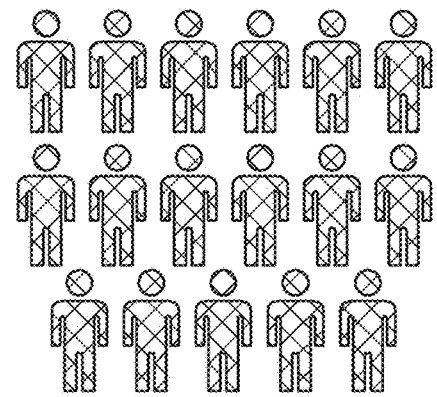
Figure 3A:
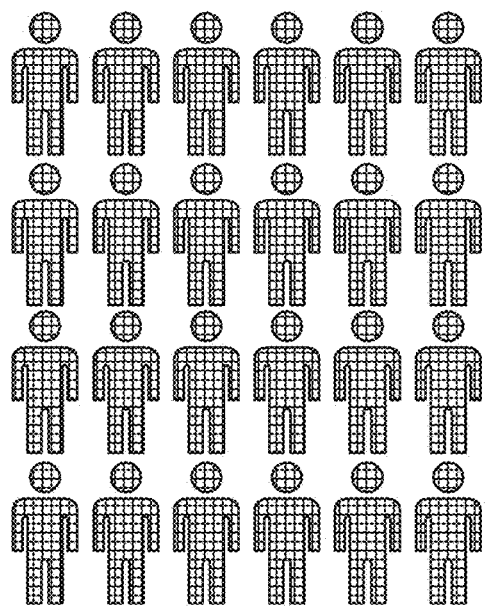
Figure 3A:
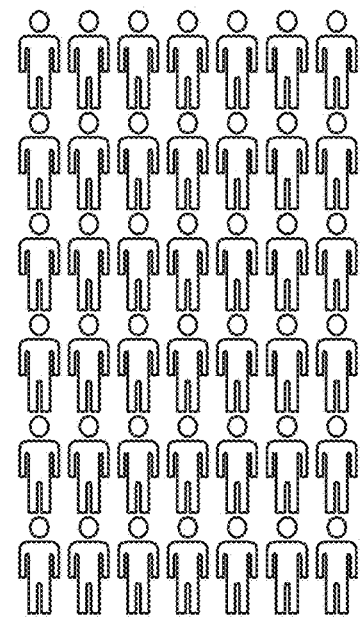

As described herein, gene expression data was evaluated in order to identify transcriptional signatures predictive of a patient's clinical response to immune checkpoint blockade (ICB) therapy. Gene expression data including a patient's pre-treatment tumor RNA-seq data and their response to therapy was obtained from the following datasets: (1) 42 patients with metastatic melanoma treated with anti-CTLA4 (Van Allen et al. dataset); (2) 28 melanoma patients treated with anti-PD1, (Hugo et al. dataset); (3) 24 patients treated with anti-CTLA4 (Nathanson et al. dataset); and (4) a subset of 17 TCGA patients treated with either anti-PD1 or anti-CTLA4 (SKCM17 dataset; Table 1). In total, 111 patient tumor samples were analyzed (FIG. 3A).

TABLE 1

Clinical Data for Melanoma Patients Treated with Immune Checkpoint Blockade Therapy in the TCGA SKCM Melanoma Dataset.

| Sample | Patient | Drug | Therapy type | Recist | Response |
| --- | --- | --- | --- | --- | --- |
| TCGA.DA.A3F2.06A | TCGA.DA.A3F2 | ipilimumab | aCTLA4 | PR | R |
| TCGA.DA.A3F5.06A | TCGA.DA.A3F5 | pembrolizumab | aPD1 | SD | R |
| TCGA.EE.A29C.06A | TCGA.EE.A29C | ipilimumab | aCTLA4 | SD | R |
| TCGA.EE.A2GS.06A | TCGA.EE.A2GS | ipilimumab | aCTLA4 | PD | NR |
| TCGA.EE.A3JI.06A | TCGA.EE.A3JI | ipilimumab | aCTLA4 | PD | NR |
| TCGA.FR.A3YN.06A | TCGA.FR.A3YN | ipilimumab | aCTLA4 | CR | R |
| TCGA.FR.A3YO.06A | TCGA.FR.A3YO | ipilimumab | aCTLA4 | SD | R |
| TCGA.FR.A8YD.06A | TCGA.FR.A8YD | ipilimumab | aCTLA4 | SD | R |
| TCGA.GF.A3OT.06A | TCGA.GF.A3OT | ipilimumab | aCTLA4 | PD | NR |
| TCGA.GN.A4U4.06A | TCGA.GN.A4U4 | ipilimumab | aCTLA4 | PR | R |
| TCGA.GN.A4U9.06A | TCGA.GN.A4U9 | ipilimumab | aCTLA4 | PR | R |
| TCGA.GN.A8LK.06A | TCGA.GN.A8LK | ipilimumab | aCTLA4 | PD | NR |
| TCGA.GN.A8LN.01A | TCGA.GN.A8LN | ipilimumab | aCTLA4 | PR | R |
| TCGA.QB.AA9O.06A | TCGA.QB.AA9O | ipilimumab | aCTLA4 | PD | NR |
| TCGA.WE.A8K5.06A | TCGA.WE.A8K5 | ipilimumab | aCTLA4 | PD | NR |
| TCGA.WE.A8ZN.06A | TCGA.WE.A8ZN | nivolumab | aPD1 | PD | NR |
| TCGA.WE.AAA0.06A | TCGA.WE.AAA0 | ipilimumab | aCTLA4 | PD | NR |

Figure 3B:
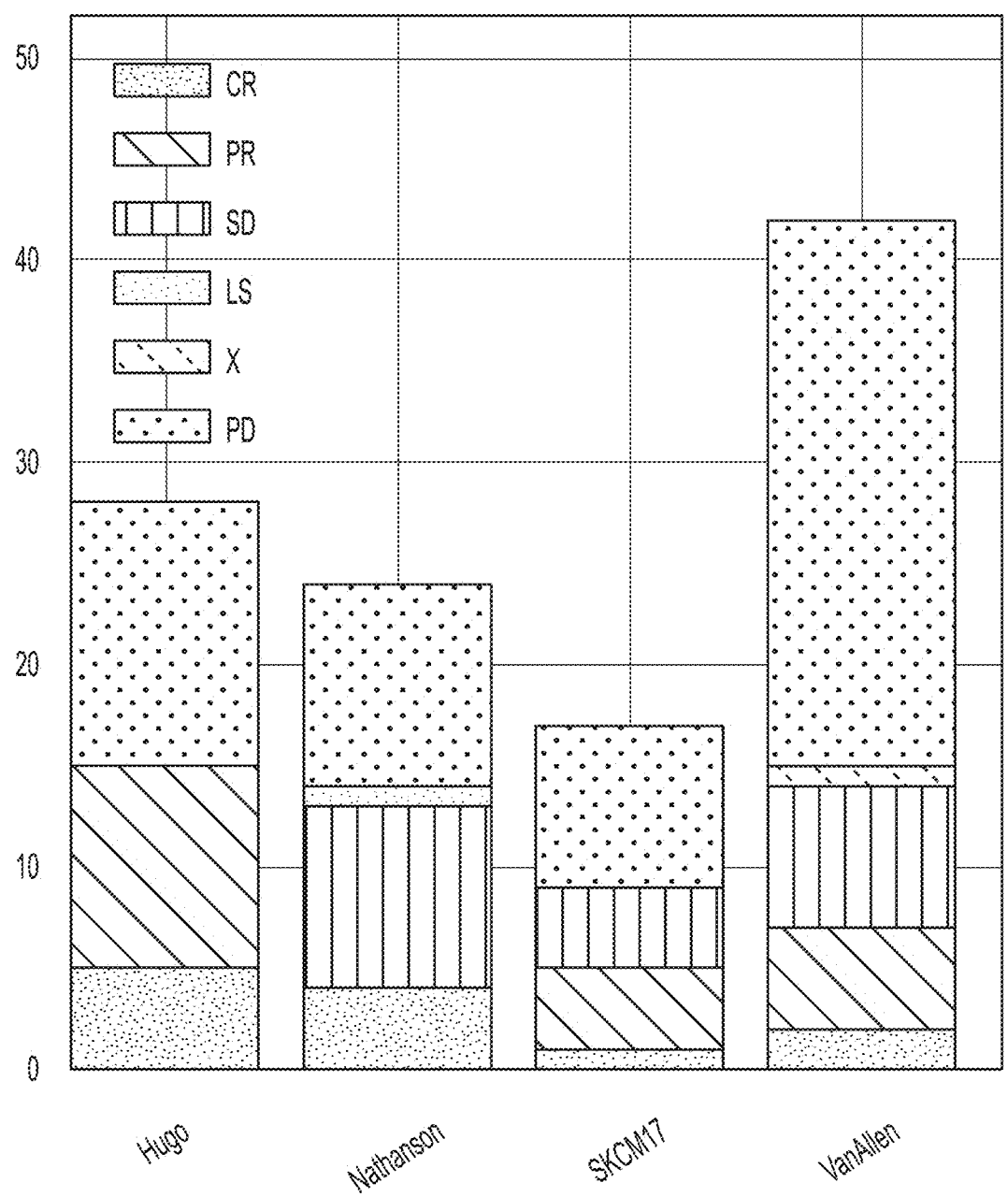
FIG. 3B is a graph showing patient response for each dataset illustrated in FIG. 3A, in accordance with some embodiments of the technology described herein.
Figure 3C:
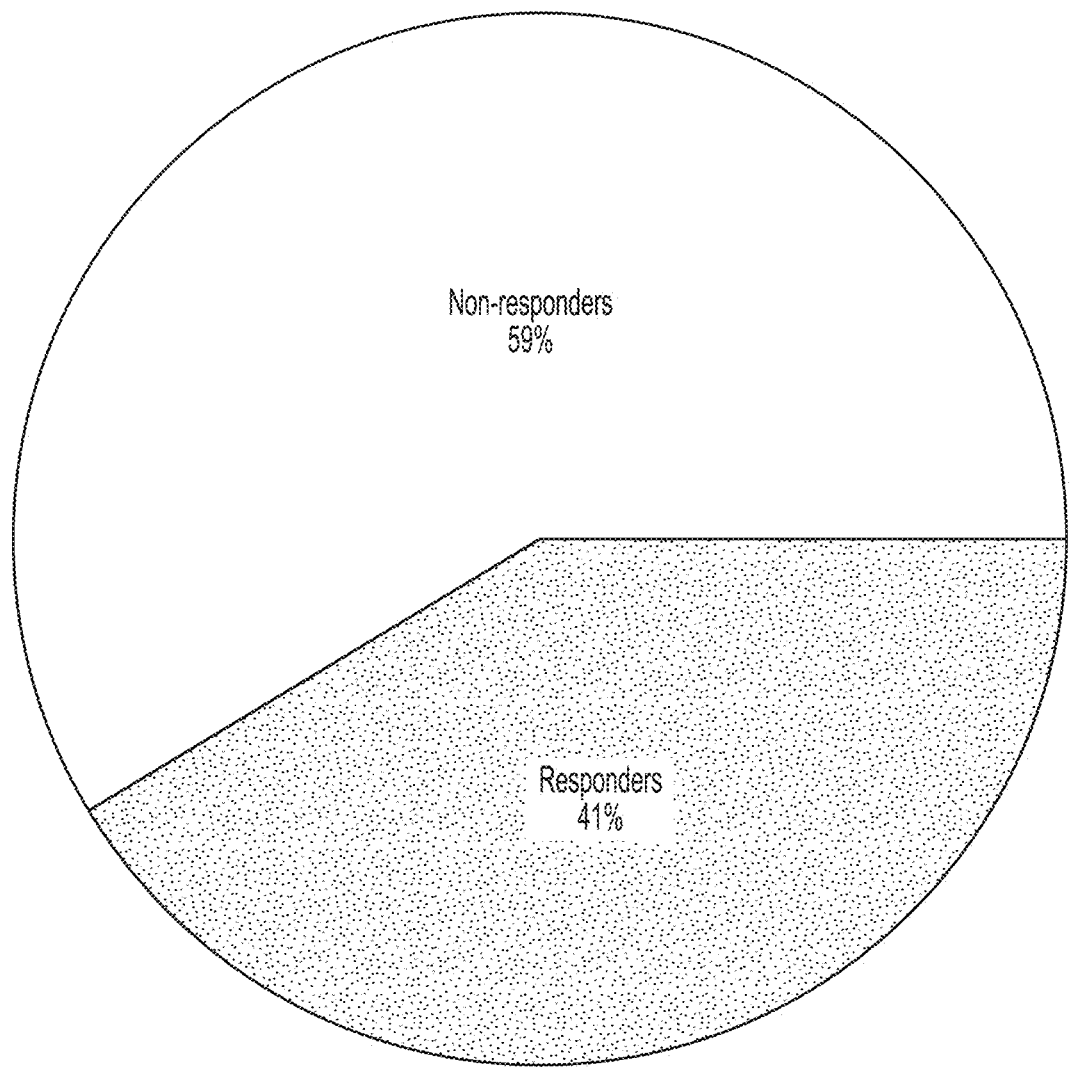
FIG. 3C is a graph showing overall patient response for merged datasets, in accordance with some embodiments of the technology described herein.
Figure 3F:
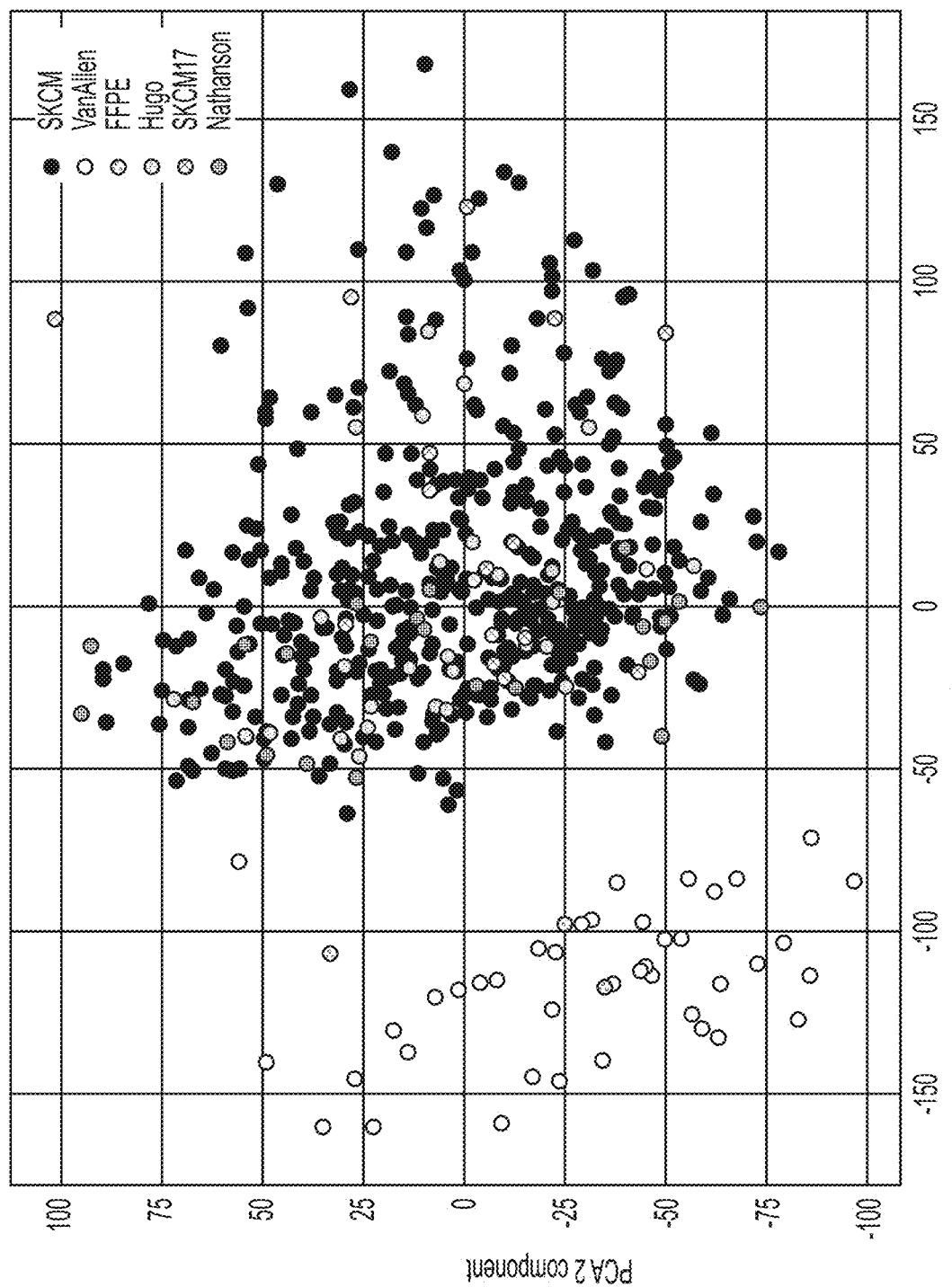
FIG. 3F shows data from a principal component analysis of merged datasets combined with non-immune checkpoint blockade treated TCGA samples for SKCM melanoma (453 samples, SKCM453) and formalin-fixed paraffin-embedded (FFPE) fixed samples from GSE66539 dataset, in accordance with some embodiments of the technology described herein.

Patients annotated with progressive disease (PD) were identified as non-responders, and patients annotated with stable disease (SD), partial response (PR), complete response (CR), long survival (LS) or unknown status of disease (X) were identified as responders (FIG. 3B). The fraction of responders in the Van Allen dataset was ~30%, which was lower than that of the other three datasets (~50% for each of the other datasets) (FIG. 3B). Patient response in FIG. 3B is abbreviated as follows: CR—complete response; PR—partial response; SD—stable disease; LS—long survival; PD—progressive disease; and X—unknown. Among the four datasets, about 40% of patients were identified as responders (FIG. 3C). In FIG. 3C, non-responders were defined as having progressive disease (PD), and non-responders were defined as having complete response (CR), partial response (PR), stable disease (SD), and long survival (LS). For each dataset, gene expression was profiled as 48 to 100 bp long paired RNA-seq reads with technical characteristics of sequencing comparable across datasets (Table 2). Coverage and alignment rate for each melanoma sample was analyzed (Table 3). Raw RNA-seq data was uniformly processed across datasets to obtain individual expression tables (supplementary files).

TABLE 2

Technical Characteristics of RNASeq Data.

| | Nathanson | Van Allen | Hugo | SKCM17 |
| --- | --- | --- | --- | --- |
| mRNA | total stranded RNA | RNA | mRNA stranded | . |
| RNA extraction | . | Qiagen AllPrep DNA/RNA Mini Kit | . | . |
| Library preparation kit | Illumina TruSeq mRNA Library Kit (v2) | Illumina's TruSeq Stranded Total RNA Sample Prep Kit | | Illumina mRNA TruSeq kit |
| Paired | + | + | + | + |
| Read length | 50 bp | 76 bp | 100 bp | 48 bp |
| Sequencer | HiSeq 2500 | HiSeq 2500 | HiSeq 2000 | HiSeq 2000 |
| Reads per sample | 47-85 million | 31-96 million | 12-105 million | 42-96 million |
| GC content | 47-52% | 45-56% | 46-52% | 48-56% |
| Duplications | 51-65% | 16-53% | 43-74% | 21-43% |
| Number of highly covered (>10 reads) genes | 16,585 | 16,875 | 16,756 | 16,265 |

TABLE 3

Coverage and Alignment Rate for Melanoma Samples.

| Dataset | Sample | Reads aligned | Total reads | Alignment rate |
|---|---|---|---|---|
| Hugo | SRR3184279 | 71,672,336 | 82,476,159 | 87% |
| Hugo | SRR3184280 | 43,931,224 | 50,084,443 | 88% |
| Hugo | SRR3184281 | 62,368,931 | 83,417,309 | 75% |
| Hugo | SRR3184282 | 68,685,225 | 72,397,468 | 95% |
| Hugo | SRR3184283 | 22,581,053 | 107,450,280 | 21% |
| Hugo | SRR3184284 | 44,128,122 | 59,031,115 | 75% |
| Hugo | SRR3184285 | 23,790,767 | 36,566,270 | 65% |
| Hugo | SRR3184286 | 68,488,552 | 85,492,431 | 80% |
| Hugo | SRR3184287 | 78,604,608 | 92,701,616 | 85% |
| Hugo | SRR3184288 | 49,352,255 | 66,594,303 | 74% |
| Hugo | SRR3184289 | 67,841,602 | 80,651,371 | 84% |
| Hugo | SRR3184290 | 88,953,368 | 105,392,870 | 84% |
| Hugo | SRR3184291 | 45,741,837 | 63,320,771 | 72% |
| Hugo | SRR3184292 | 41,664,437 | 60,266,273 | 69% |
| Hugo | SRR3184293 | 36,314,491 | 55,931,661 | 65% |
| Hugo | SRR3184294 | 8,986,341 | 47,901,563 | 19% |
| Hugo | SRR3184295 | 64,149,266 | 87,727,770 | 73% |
| Hugo | SRR3184296 | 48,644,657 | 76,472,375 | 64% |
| Hugo | SRR3184297 | 43,902,284 | 60,745,831 | 72% |
| Hugo | SRR3184298 | 69,633,194 | 92,289,809 | 75% |
| Hugo | SRR3184299 | 64,454,338 | 87,211,314 | 74% |
| Hugo | SRR3184300 | 40,839,482 | 47,512,085 | 86% |
| Hugo | SRR3184301 | 48,176,845 | 61,680,455 | 78% |
| Hugo | SRR3184302 | 39,553,816 | 58,770,657 | 67% |
| Hugo | SRR3184303 | 36,455,684 | 60,299,574 | 60% |
| Hugo | SRR3184304 | 48,398,033 | 61,696,400 | 78% |
| Hugo | SRR3184305 | 41,797,786 | 58,664,872 | 71% |
| Hugo | SRR3184306 | 43,235,175 | 62,472,286 | 69% |
| VanAllen | pat02 | 30,188,320 | 39,589,911 | 76% |
| VanAllen | pat03 | 72,337,690 | 104,100,502 | 69% |
| VanAllen | pat04 | 31,918,500 | 41,468,762 | 77% |
| VanAllen | pat06 | 41,865,345 | 59,007,541 | 71% |
| VanAllen | pat08 | 48,061,494 | 64,518,469 | 74% |
| VanAllen | pat118_re | 80,204,739 | 120,469,696 | 67% |
| VanAllen | pat119_re | 49,357,924 | 72,083,656 | 68% |
| VanAllen | pat123_re | 78,055,654 | 123,868,825 | 63% |
| VanAllen | pat126_re | 65,756,291 | 92,917,917 | 71% |
| VanAllen | pat14 | 42,726,951 | 57,040,038 | 75% |
| VanAllen | pat15 | 29,440,566 | 43,173,636 | 68% |
| VanAllen | pat16 | 21,853,322 | 32,138,345 | 68% |
| VanAllen | pat19 | 25,361,929 | 33,875,410 | 75% |
| VanAllen | pat20 | 32,588,374 | 43,836,426 | 74% |
| VanAllen | pat25 | 60,984,757 | 88,224,849 | 69% |
| VanAllen | pat27 | 55,593,667 | 70,803,929 | 79% |
| VanAllen | pat28 | 47,915,129 | 63,216,287 | 76% |
| VanAllen | pat29 | 41,087,798 | 57,895,713 | 71% |
| VanAllen | pat33 | 51,892,757 | 71,734,132 | 72% |
| VanAllen | pat36 | 44,611,664 | 65,259,199 | 68% |
| VanAllen | pat37 | 48,269,852 | 60,666,410 | 80% |
| VanAllen | pat38 | 55,614,898 | 74,187,557 | 75% |
| VanAllen | pat39 | 43,550,388 | 58,304,835 | 75% |
| VanAllen | pat40 | 43,185,487 | 55,885,806 | 77% |
| VanAllen | pat43 | 29,689,491 | 40,958,545 | 72% |
| VanAllen | pat44 | 43,092,641 | 60,309,282 | 71% |
| VanAllen | pat45 | 25,131,710 | 33,461,958 | 75% |
| VanAllen | pat46 | 33,917,697 | 46,460,369 | 73% |
| VanAllen | pat47 | 22,605,771 | 31,205,567 | 72% |
| VanAllen | pat49 | 61,505,632 | 85,121,041 | 72% |
| VanAllen | pat50 | 39,571,453 | 57,981,236 | 68% |
| VanAllen | pat79 | 31,926,224 | 41,996,993 | 76% |
| VanAllen | pat80 | 52,389,811 | 69,065,846 | 76% |
| VanAllen | pat81 | 35,577,908 | 47,986,804 | 74% |
| VanAllen | pat83 | 49,545,724 | 71,550,718 | 69% |
| VanAllen | pat85 | 46,905,314 | 62,571,197 | 75% |
| VanAllen | pat86 | 36,996,974 | 48,504,858 | 76% |
| VanAllen | pat88 | 60,411,904 | 84,927,259 | 71% |
| VanAllen | pat90 | 51,035,609 | 67,592,620 | 76% |
| VanAllen | pat91 | 32,328,634 | 42,780,460 | 76% |
| VanAllen | pat98 | 39,951,523 | 55,591,443 | 72% |
| SKCM17 | TCGA-DA-A3F2-06A | 36,193,907 | 73,189,481 | 49% |
| SKCM17 | TCGA-DA-A3F5-06A | 63,471,321 | 98,574,681 | 64% |
| SKCM17 | TCGA-EE-A29C-06A | 42,106,901 | 58,671,235 | 72% |
| SKCM17 | TCGA-EE-A2GS-06A | 75,467,030 | 106,193,891 | 71% |
| SKCM17 | TCGA-EE-A3JI-06A | 82,822,349 | 130,483,053 | 63% |
| SKCM17 | TCGA-FR-A3YN-06A | 77,212,284 | 125,432,957 | 62% |
| SKCM17 | TCGA-FR-A3YO-06A | 62,820,875 | 94,334,439 | 67% |

TABLE 3-continued

Coverage and Alignment Rate for Melanoma Samples.

| Dataset | Sample | Reads aligned | Total reads | Alignment rate |
|---|---|---|---|---|
| SKCM17 | TCGA-FR-A8YD-06A | 48,621,273 | 84,908,649 | 57% |
| SKCM17 | TCGA-GF-A3OT-06A | 75,562,700 | 104,584,553 | 72% |
| SKCM17 | TCGA-GN-A4U4-06A | 64,116,884 | 109,375,310 | 59% |
| SKCM17 | TCGA-GN-A4U9-06A | 52,387,354 | 86,570,993 | 61% |
| SKCM17 | TCGA-GN-A8LK-06A | 50,296,635 | 87,404,657 | 58% |
| SKCM17 | TCGA-GN-A8LN-01A | 47,366,833 | 80,531,332 | 59% |
| SKCM17 | TCGA-QB-AA9O-06A | 28,086,988 | 56,838,966 | 49% |
| SKCM17 | TCGA-WE-A8K5-06A | 59,286,015 | 96,010,909 | 62% |
| SKCM17 | TCGA-WE-A8ZN-06A | 33,627,214 | 71,681,690 | 47% |
| SKCM17 | TCGA-WE-AAA0-06A | 66,656,729 | 98,459,389 | 68% |
| Nathanson | pat0167 | 55,402,577 | 77,953,148 | 71% |
| Nathanson | pat0346 | 43,813,860 | 58,286,945 | 75% |
| Nathanson | pat1494 | 43,412,097 | 62,890,358 | 69% |
| Nathanson | pat1509 | 43,442,558 | 57,900,066 | 75% |
| Nathanson | pat1867 | 43,588,370 | 61,200,115 | 71% |
| Nathanson | pat2051 | 41,798,937 | 61,261,388 | 68% |
| Nathanson | pat2056 | 32,605,810 | 58,611,420 | 56% |
| Nathanson | pat3549 | 40,956,284 | 55,613,683 | 74% |
| Nathanson | pat4631 | 67,686,777 | 86,935,831 | 78% |
| Nathanson | pat4810 | 45,242,016 | 59,981,572 | 75% |
| Nathanson | pat4949 | 44,131,171 | 59,900,765 | 74% |
| Nathanson | pat5038 | 43,310,892 | 55,999,930 | 77% |
| Nathanson | pat5118 | 45,812,476 | 65,647,117 | 70% |
| Nathanson | pat5784 | 39,473,483 | 62,233,636 | 63% |
| Nathanson | pat6126 | 68,865,936 | 85,530,712 | 81% |
| Nathanson | pat6336 | 45,596,291 | 62,254,026 | 73% |
| Nathanson | pat6494 | 38,591,235 | 53,937,843 | 72% |
| Nathanson | pat7357 | 39,861,473 | 55,736,777 | 72% |
| Nathanson | pat7623 | 45,724,744 | 63,741,185 | 72% |
| Nathanson | pat8727 | 39,525,208 | 61,208,006 | 65% |
| Nathanson | pat9449 | 68,739,443 | 87,012,076 | 79% |
| Nathanson | pat9521 | 74,440,314 | 87,216,766 | 85% |
| Nathanson | pat9699 | 49,683,721 | | |
| Nathanson | pat9705 | 57,437,361 | | |

To evaluate consistency of gene expression profiles across the datasets, principal component analysis (PCA) on the merged dataset of 111 patients in log-normalized TPM gene expressions was performed. This analysis showed that the clustering of the Van Allen dataset was distinct from that of the other datasets (FIG. 3D). Cross-correlation between expression profiles was also different for the Van Allen dataset as compared to the other datasets (Table 4).

TABLE 4

Cross-Correlation Between Log-Transformed Gene Expression For Analyzed Datasets

| | Hugo | Van Allen | SKCM17 | Nathanson |
|---|---|---|---|---|
| Hugo | 1.00 | 0.89 | 0.99 | 6.99 |
| VanAllen | 0.89 | 1.00 | 0.88 | 0.90 |
| SKCM17 | 0.99 | 0.88 | 1.00 | 0.98 |
| Nathanson | 0.99 | 0.90 | 0.98 | 1.00 |

Clustering of the datasets of melanoma patients treated with an immune checkpoint blockade therapy was compared to clustering of a dataset of melanoma patients treated with a non-immune checkpoint blockade therapy (SKCM453 dataset). The Van Allen dataset also showed distinct clustering when plotted together with the SKCM453 dataset on a PCA plot (FIG. 3E).

The Van Allen dataset was generated using formalin-fixed paraffin-embedded (FFPE) samples and the other datasets were generated from fresh frozen samples. To determine whether sample preparation effects clustering, principal component analysis on three FFPE melanoma samples (GSE66539) was performed. These samples showed similar clustering to the Van Allen dataset (FIG. 1F). These results suggested that the different sample preparation of the Van Allen dataset was responsible for its distinct clustering. Therefore, the Van Allen dataset was excluded from further analysis.

Taken together, these results showed that the Hugo, Nathanson and SKCM17 datasets displayed comparable behavior, and accordingly these datasets were used for further analysis.

Example 2: Gene Expression Ratios Separated Responders and Non-Responders

Common predictive signatures that were shared between the datasets were identified as described below. First, differential expression between responding and non-responding subpopulations was performed for each dataset. This analysis yielded 803 differentially expressed genes in the Hugo dataset, 443 differentially expressed genes in the Nathanson dataset, and 636 differentially expressed genes in the SKCM17 dataset. Strikingly, only a few common differentially expressed genes (DESeq1, p-value <0.05) were identified among the Hugo, Nathanson, and SKCM17 datasets, with partial association to therapy response (FIG. 4A).

Gene expression analysis of single genes was not predictive of therapy response for the three datasets. Therefore, gene expression ratio analysis was performed as shown in FIG. 4B. For this analysis shown as process 400, 10,000 genes that were most expressed in the three datasets were selected in act 410. Next, 49,999,995 ratios were calculated for the 10,000 highly expressed genes in act 420. Ratios with the same directionality to patient response were retained in act 430. In other words, ratios that had positive fold changes or negative fold changes between responder and non-responder groups in each dataset were selected. This yielded 11,994,542 ratios that were then further analyzed to determine which ratios were most predictive of therapy response in each dataset.

Figure 4D:
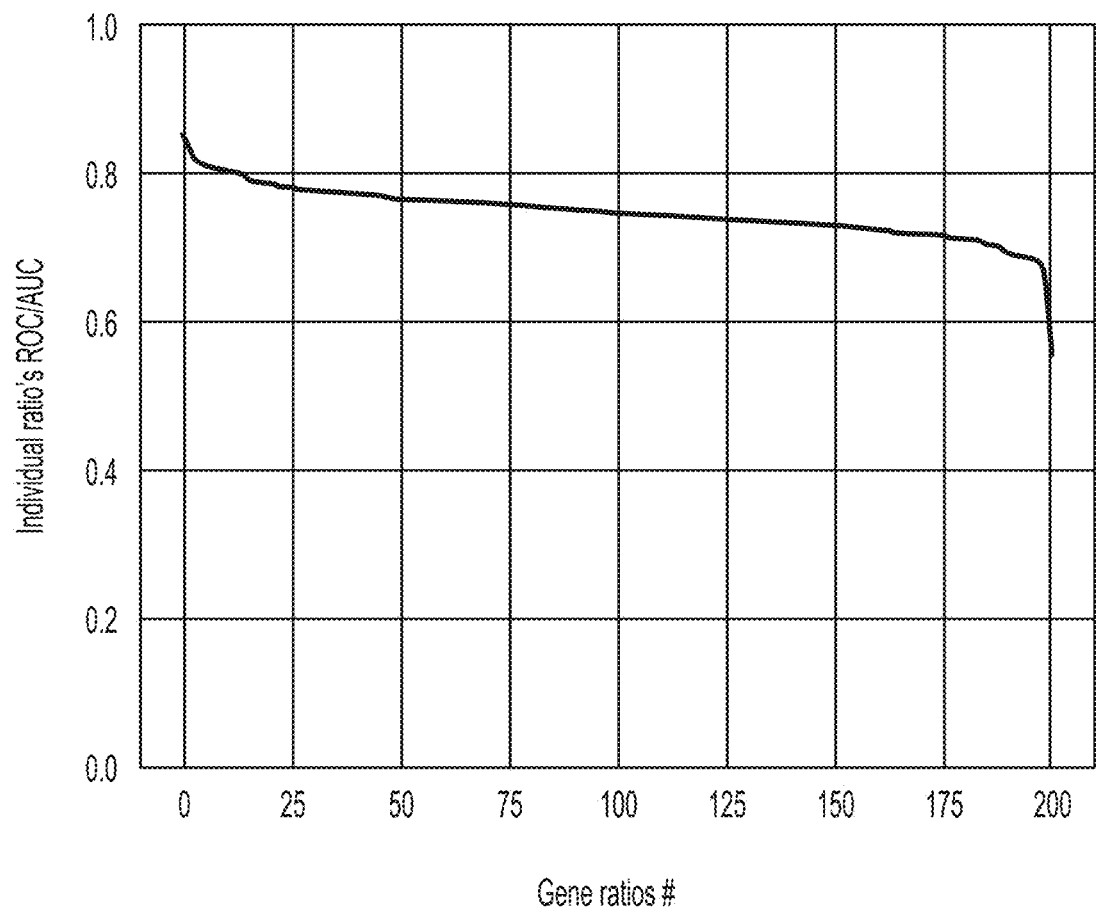
FIG. 4D is a graph showing individual ROC/AUC prediction scores for each gene ratio, in accordance with some embodiments of the technology described herein.
Figure 4F:
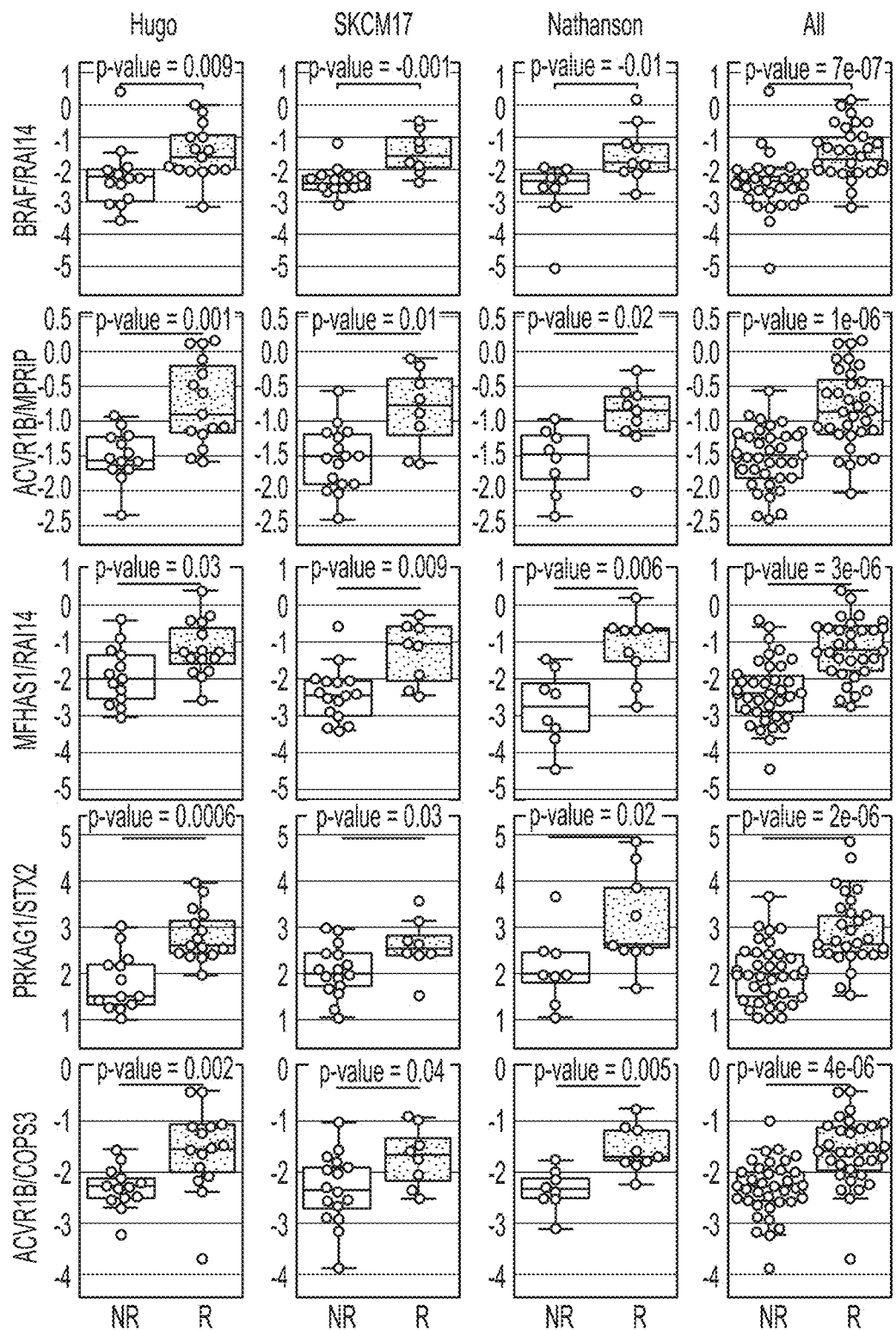
FIG. 4F shows boxplots for 5 gene ratios for each dataset and a merged dataset, in accordance with some embodiments of the technology described herein.

By applying the Mann-Whitney test, 404 ratios with FWER<0.05 in each dataset were identified in act 440. Ratios having outlying standard deviations (14 ratios) were filtered out, which resulted in 390 ratios in act 450. Highly correlated (Pearson correlation r>0.75 in TCGA SKCM cohort) ratios were removed by leaving a single ratio in each group, which resulted in 201 gene expression ratios in act 460. Individual ROC/AUC prediction scores were calculated for each of the 201 gene expression ratios (FIG. 4D). To simplify readout, numerator and denominator for ratios that are overexpressed in non-responders were swapped, thereby making the pro-response directionality the same for the ratios. The 201 gene expression ratios showed high power in separating responders and non-responders in both principal component analysis (FIG. 4C) and differential expression analysis (FIGS. 4E-4F).

Thus, these results demonstrated that gene expression ratio analysis separated patients that responded to an immune checkpoint blockade therapy from those that did not.

Example 3: Gene Expression Based Predictive Model Predicted Therapy Response

A logistic-regression model was constructed that defined linear combinations of gene expression ratios and corresponding intercept values that optimally classified samples in two classes by associated therapy response. Ratios for the model were selected by a greedy add algorithm, which iteratively extended the model by those new gene ratios that maximally increased the model's predicted ROC/AUC score (FIG. 5A). Scores were evaluated by 10-fold cross-validation. The model reached its maximal performance at 6 gene ratios (FIG. 5A).

Figure 5D:
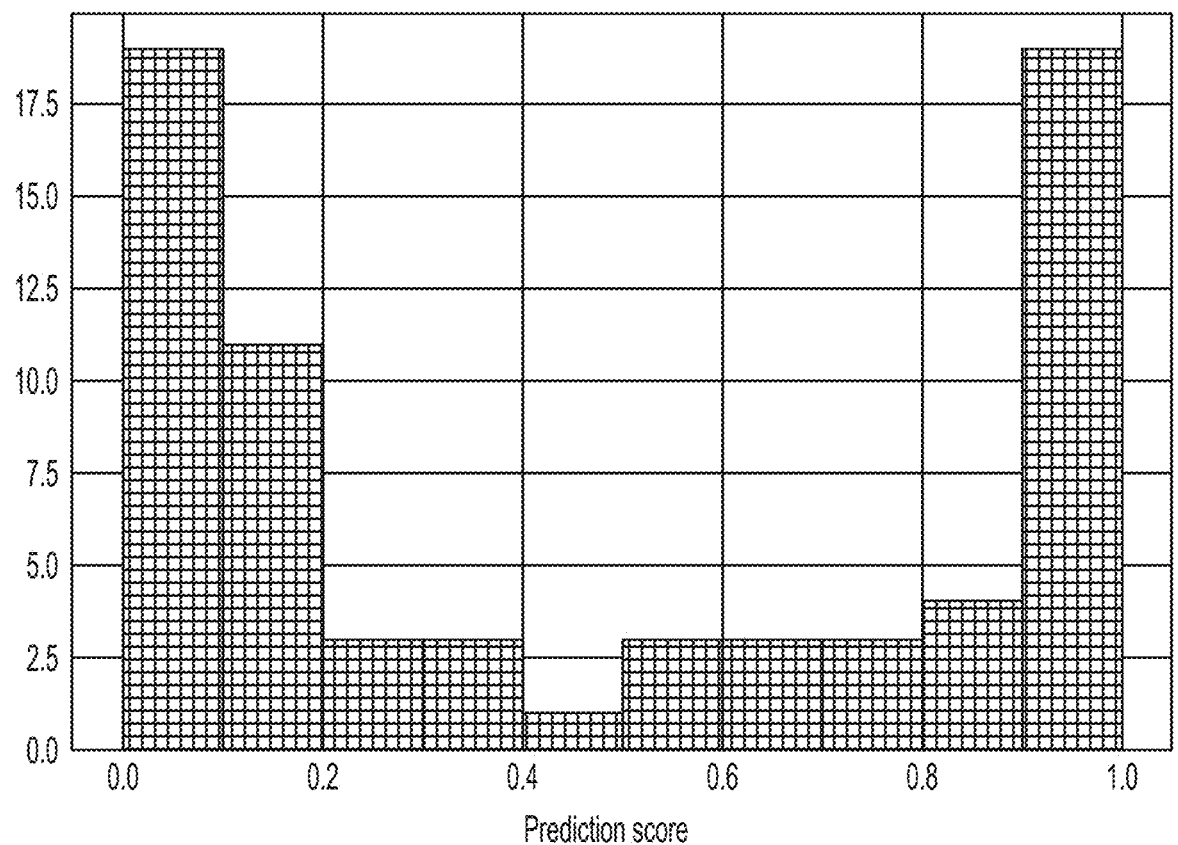
FIG. 5D is a graph showing distribution of predicted output scores of the statistical model for predicting whether a subject will response to an immune checkpoint blockade therapy over merged datasets, in accordance with some embodiments of the technology described herein.

The waterfall plot (FIG. 5B) showed high efficiency of the constructed predictive model and remarkable separation of responders and non-responders into two distinct groups with ROC/AUC=0.993 and F1 score=0.942. Such separation was also confirmed by a strongly bimodal form of the model's prediction score distribution for the entire melanoma cohort from TCGA (FIG. 5G) and the three immune checkpoint blockade treated cohorts (FIG. 5D).

Figure 5E:
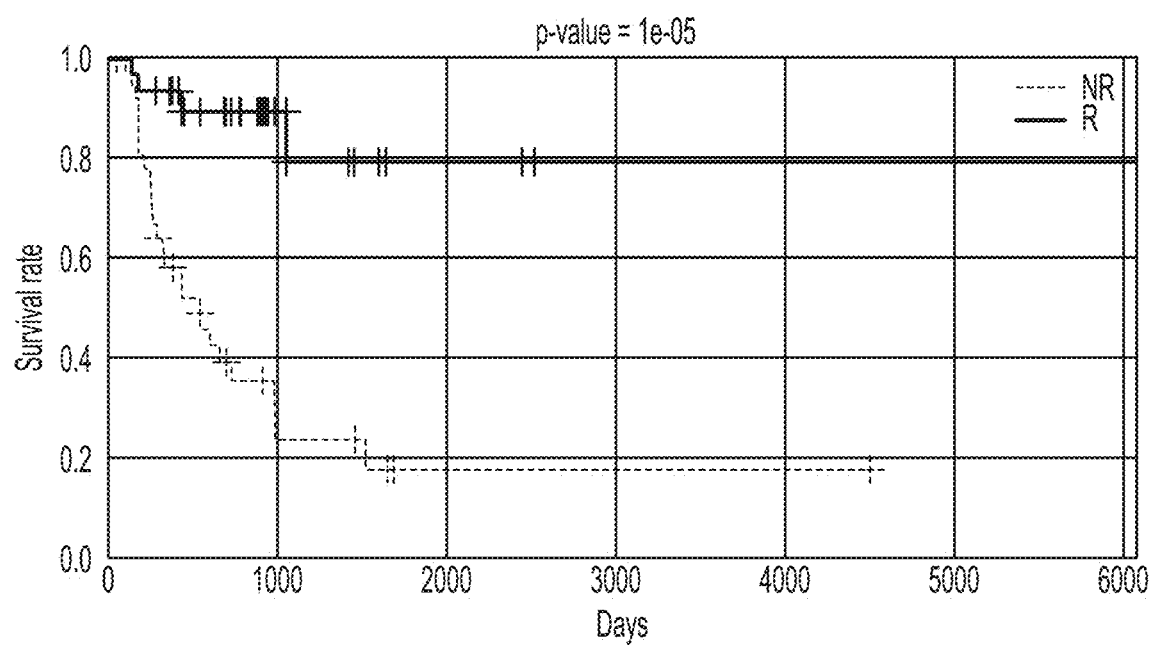
FIG. 5E shows Kaplan-Meier survival curves for likely responders (R) and non-responders (NR) predicted by the statistical model for predicting whether a subject will response to an immune checkpoint blockade therapy for merged datasets, in accordance with some embodiments of the technology described herein.
Figure 5F:
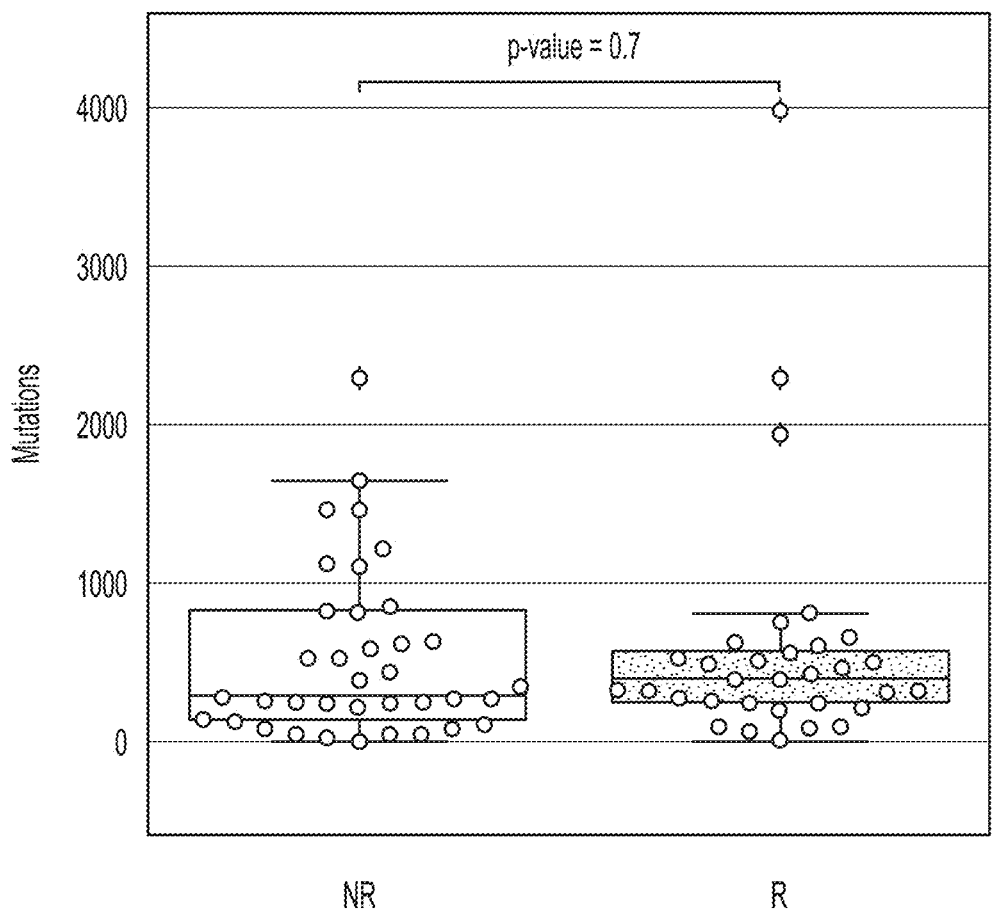
FIG. 5F shows boxplots for mutation load in likely responders (R) and non-responders (NR) predicted by the statistical model for predicting whether a subject will response to an immune checkpoint blockade therapy for merged datasets, in accordance with some embodiments of the technology described herein.
Figure 5G:
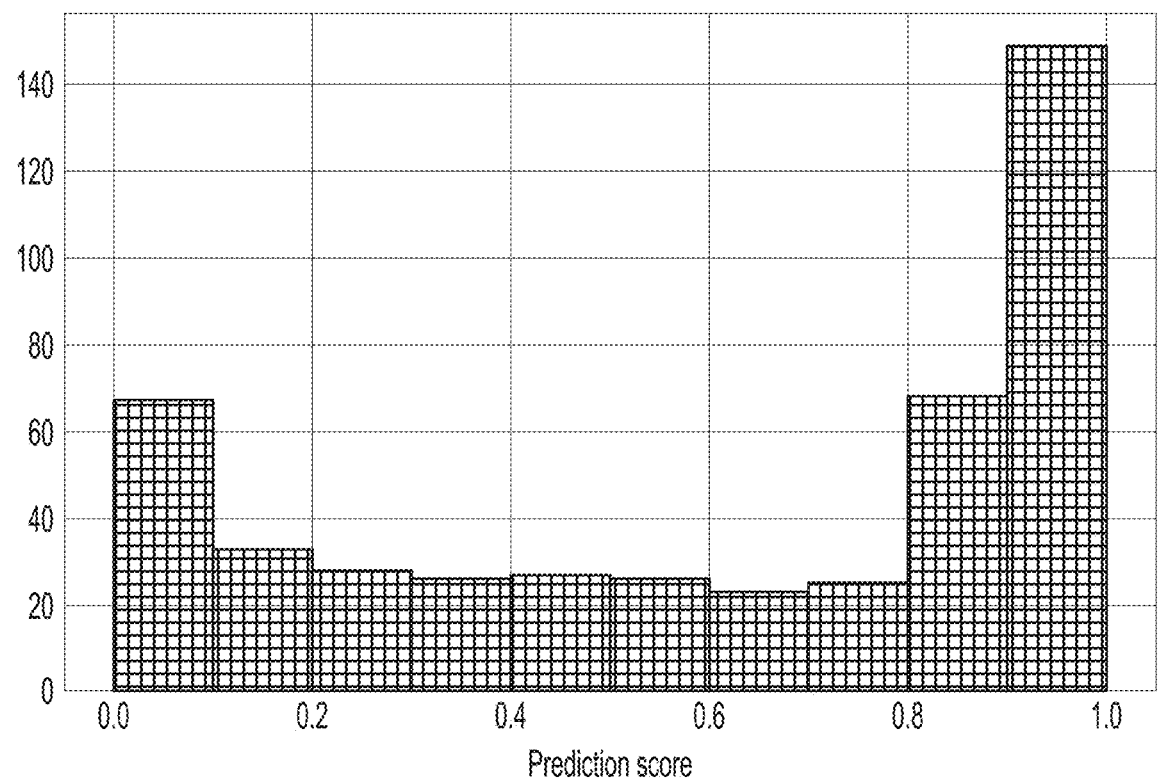
FIG. 5G shows distribution of prediction output scores calculated by the statistical model for predicting whether a subject will response to an immune checkpoint blockade therapy for the SKCM453 dataset, in accordance with some embodiments of the technology described herein.
Figure 5H:
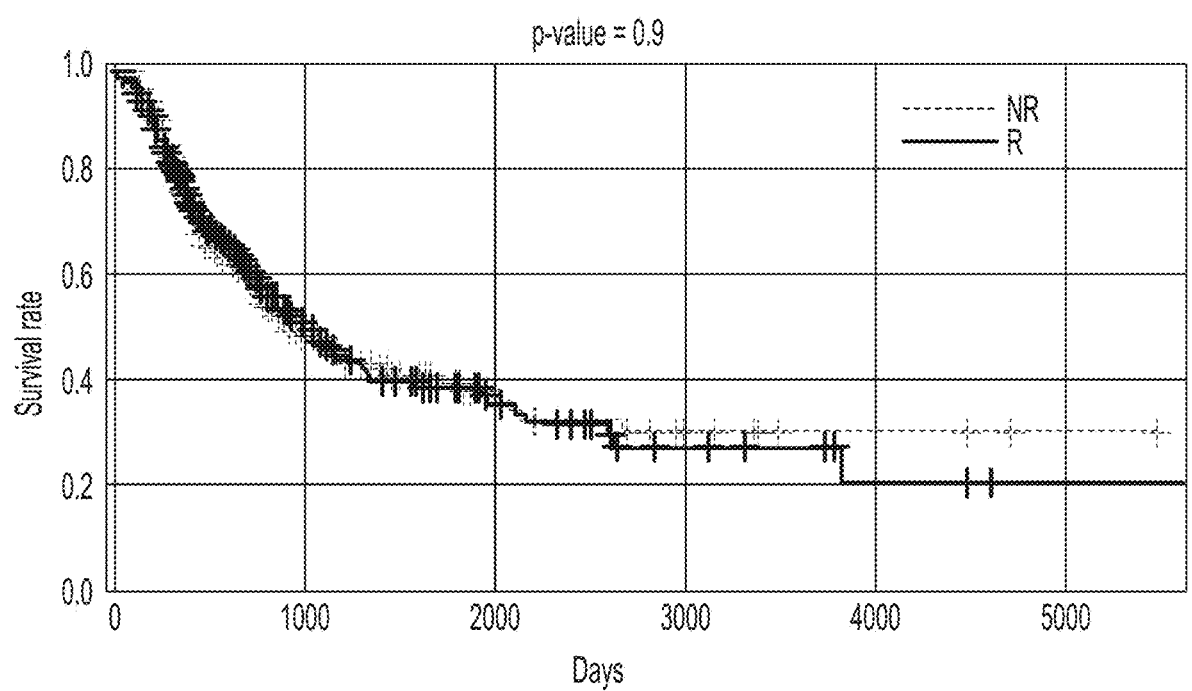
FIG. 5H shows Kaplan-Meier survival curves for likely responders (R) and non-responders (NR) predicted by the statistical model for predicting whether a subject will response to an immune checkpoint blockade therapy for the SKCM453 dataset, in accordance with some embodiments of the technology described herein.
Figure 5I:
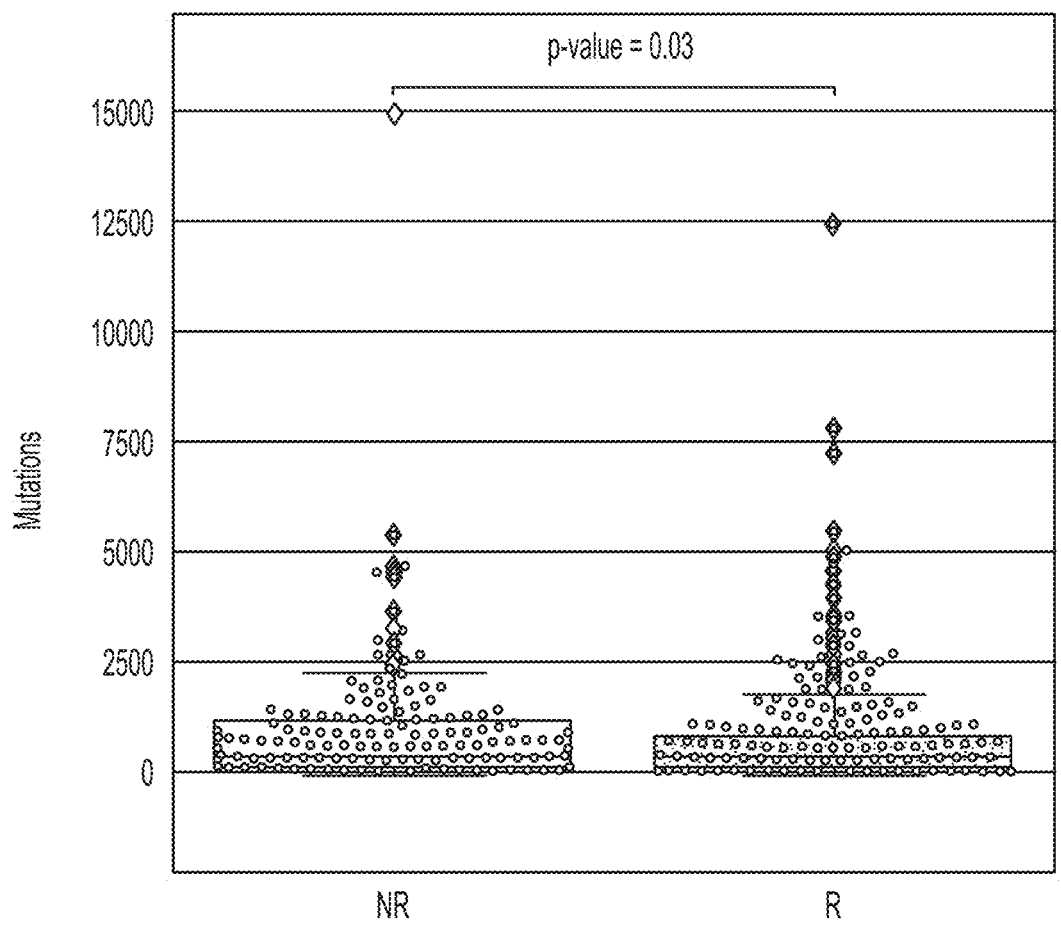
FIG. 5I shows boxplots for mutation load in likely responders (R) and non-responders (NR) predicted by the statistical model for predicting whether a subject will response to an immune checkpoint blockade therapy for the SKCM453 dataset, in accordance with some embodiments of the technology described herein.

The model was evaluated to determine whether it has a general prognostic function in melanoma. Analysis of survival profiles identified distinct survival profiles between predicted responders and non-responders in immune checkpoint blockade therapy treated cohorts (FIG. 5E) but not for the TCGA SKCM melanoma cohort (FIG. 5G). Thus, the constructed model accurately predicts a patient's response to immune checkpoint blockade therapy.

The constructed predictor model also separated two distinct groups of tumors. Prediction scores for tumor samples in both the immune checkpoint blockade treated cohort (FIG. 5D) and the entire TCGA SKCM cohort (FIG. 5G) followed a similar bi-modal distribution. Such uniformity suggests that the model has the capability to effectively distinguish likely responders and non-responders in other cohorts.

Thus, these results demonstrated that the gene expression based model predicts patient response to anti-CTLA4 and anti-PD1 checkpoint blockade therapies.

Example Embodiments

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with a checkpoint blockade therapy in the plurality of genes, wherein identifying the subset of genes associated with a checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is at least one non-transitory computer-readable storage medium storing processor-executable instructions that, when executed by at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with a checkpoint blockade therapy in the plurality of genes, wherein identifying the subset of genes associated with a checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is a method, comprising: using at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with a checkpoint blockade therapy in the plurality of genes, wherein identifying the subset of genes associated with a checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with a checkpoint blockade therapy in the plurality of genes, wherein identifying the subset of genes associated with a checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying predictor set of genes to include in the statistical model; estimating, using the expression data, parameters of the statistical model that are associated with the predictor set of genes; and storing the statistical model.

In one aspect provided herein is a system, comprising: at least one computer hardware processor; and at least one non-transitory computer-readable storage medium storing processor-executable instructions that, when executed by the at least one computer hardware processor, cause the at least one computer hardware processor to perform: accessing a statistical model, wherein the statistical model was obtained by: obtaining, for each subject in a plurality of subjects having responders to a checkpoint blockade therapy and non-responders to the checkpoint blockade therapy, expression data indicating expression levels for a plurality of genes; determining, for the plurality of genes, expression level differences between the responders and the non-responders using the expression data; identifying, using the determined expression level differences, a subset of genes associated with a checkpoint blockade therapy in the plurality of genes, wherein identifying the subset of genes associated with a checkpoint blockade therapy comprises identifying genes that are differentially expressed between the responders and non-responders with at least a threshold level of statistical significance; training, using the expression data, a statistical model for predicting efficacy of the checkpoint blockade therapy, the training comprising: identifying at least some of the subset of genes as a predictor set of genes to include in the statistical model; and estimating, using the expression data, parameters of the statistical model that are associated with the predictor set of genes; obtaining additional expression data for an additional subject; and determining, using the additional expression data and the statistical model, whether the additional subject is likely to respond positively to the checkpoint blockade therapy and/or whether the additional subject is not likely to respond positively to the checkpoint blockade therapy.

In some embodiments, the expression data is RNA expression data, DNA expression data, or protein expression data.

In some embodiments, training the statistical model comprises training a generalized linear model having a plurality of regression variables, the plurality of regression variables including a regression variable for each of the predictor set of genes.

In some embodiments, training the statistical model comprises training a logistic regression model having a plurality of regression variables, the plurality of regression variables including a regression variable for each of the predictor set of genes of genes.

In some embodiments, the logistic regression model comprises a respective plurality of weights for the plurality of regression variables, wherein estimating the parameters of the statistical model comprises: estimating the plurality of weights using the expression data for the plurality of subjects and information indicating which of the plurality of subjects responded to the checkpoint blockade therapy and/or which of the plurality of subjects did not respond to the checkpoint blockade therapy.

In some embodiments, training the statistical model comprises iteratively adding regression variables for respective genes to the statistical model.

In some embodiments, iteratively adding regression variables comprises: identifying a candidate gene in the subset of genes; augmenting a current statistical model with a regression variable for the candidate gene to obtain an augmented statistical model; evaluating performance of the augmented statistical model; and determining to add the regression variable for the candidate gene to the current statistical model based on results of evaluating the performance.

In some embodiments, evaluating performance of the augmented statistical model comprises obtaining an area under a receiver operating characteristic curve (ROC AUC) statistic.

In some embodiments, the checkpoint blockade therapy is selected from the group consisting of: a PD1 inhibitor and a CTLA4 inhibitor.

In some embodiments, the PD1 inhibitor is a molecule that inhibits PD1, PDL1, and/or PDL2. In some embodiments, the molecule that inhibits PD1, PDL1, and/or PDL2 is an antibody or antigen binding fragment thereof. In some embodiments, the molecule that inhibits PD1, PDL1, and/or PDL2 is atezolizumab, avelumab, durvalumab, nivolumab, pembrolizumab, pidilizumab, BGB-A317, BMS-936559, or analogs, derivatives, fragments, or salts thereof.

In some embodiments, the CTLA4 inhibitor is a molecule that inhibits CTLA4. In some embodiments, the molecule that inhibits CTLA4 is an antibody or antigen binding fragment thereof. In some embodiments, the molecule that inhibits CTLA4 is ipilimumab or tremelimumab.

In some embodiments, training the statistical model comprises training a generalized linear model having a plurality of regression variables, each of the plurality of regression variables representing a ratio of a pair of genes for respective pairs of members of the predictor set of genes.

In some embodiments, training the statistical model comprises training a logistic regression model having a plurality of regression variables, each of the plurality of regression variables representing a ratio of a pair of genes for respective pairs of members of the predictor set of genes.

In some embodiments, the logistic regression model comprises a respective plurality of weights for the plurality of regression variables, and estimating the parameters of the statistical model comprises: estimating the plurality of weights using the expression data for the plurality of subjects and information indicating which of the plurality of subjects responded to the checkpoint blockade therapy and/or which of the plurality of subjects did not respond to the checkpoint blockade therapy.

In some embodiments, training the statistical model comprises iteratively adding regression variables for respective genes to the statistical model. In some embodiments, iteratively adding regression variables comprises: identifying a candidate gene in the subset of genes; augmenting a current statistical model with a regression variable for the candidate gene to obtain an augmented statistical model; evaluating performance of the augmented statistical model; and determining to add the regression variable for the candidate gene to the current statistical model based on results of evaluating the performance. In some embodiments, evaluating performance of the augmented statistical model comprises obtaining an area under a receiver operating characteristic curve (ROC AUC) statistic.

In some embodiments, the statistical model comprises a first set of dependent variables, each representing a ratio of a pair of genes, wherein the genes are selected from: BRAF, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the statistical model comprises a first set of dependent variables, each representing a ratio of a pair of genes, wherein the genes are selected from: BRAF, PRKAG1, STX2, AGPAT3, FYN, CMIP, ROBO4, RAB40C, HAUS8, SNAP23, SNX6, XAGE1E, SERPINF1, RAI14, SIRPA, MT1X, NEK3, TGFB3, USP13, HLA-DRB4, IGF2, and MICAL1.

In some embodiments, the statistical model comprises a first set of dependent variables, each representing a ratio of a pair of genes, wherein the genes comprise: BRAF, RAI14, PRKAG1, STX2, AGPAT3, FYN, CMIP, ROBO4, RAB40C, HAUS8, SNAP23, and SNX6.

In some embodiments, the statistical model comprises a first set of dependent variables, each representing a ratio of a pair of genes, wherein the genes consist of: BRAF, RAI14, PRKAG1, STX2, AGPAT3, FYN, CMIP, ROBO4, RAB40C, HAUS8, SNAP23, and SNX6.

In some embodiments, the first set of dependent variables comprises at least two ratios selected from: BRAF:RAI14, ACVR1B:MPRIP, ACVR1B:COPS3, PRKAG1:STX2, NLRX1:ELAC2, MON1B:STX2, ARF3:MPRIP, ARPIN: MPRIP, SPRYD3:FLI1, TIRAP:MPRIP, GSE1:RAI14, POLR3K:HAUS8, RAB40C:HAUS8, PIGO:MPRIP, MFHAS1:USP13, GSE1:NPIPA1, DPH6:STX2, ERLIN2: RAI14, CES2:LHFP, and NAIF1:HAUS8.

In some embodiments, the first set of dependent variables comprises at least two ratios selected from: MON1B:STX2, FAM234A:LIN37, DPH6:STX2, BRAF:RAI14, ADCK2: C14ORF80, POLR3K:HAUS8, URB1:TMEM181, GCLC: NEK3, RAB40C:HAUS8, NLRX1:ELAC2, CMIP:ROBO4, NXT2:FBXO5, EIF3H:NEK3, EHHADH:SNX6, DMTN: RASD1, SLC46A1:RBM8A, ACVR1B:GTF2H2, NPEPPS: HDAC2, CXCL16:BASP1, MFHAS1:DYRK3, ACVR1B: USP13, DPH6:C14ORF166, CES2:LHFP, ACVR1B: DCP1B, NAIF1:HDGFRP2, ABCC1:TRIO, GPR107: STX2, ZDHHC7:USP13, PRKAG1:TSEN2, PC:HAUS8, LRBA:CEP192, POM121C:CNPY4, KAT14:SETD5, SLC35A5:SNX6, ATP6V1A:GTDC1, TXNL4B:AKAP8L, SLC36A1:HAUS8, PSAP:SH3BP5, CMIP:OLFML2B, TATDN3:NEK3, TASP1:DDX5, SDC4:FUT8, TMEM254: COPS3, ARF3:MPRIP, SLC46A1:PMF1-BGLAP, ATP6V1A:FBXO30, MFHAS1:C2CD5, ERAP1:SYNE1, F11R:FYN, RCHY1:RNF146, ATP6V1A:PDCD5, ACVR1B:ELAC2, CLN3:HAUS8, NAIF1:HAUS8, PRKAG1:SOCS4, HNRNPH2:USP13, TPD52:MTRF1L, ACVR1B:C14ORF80, IST1:NPIPA1, DPH6:TCEAL1, CSNK2A1:MRGBP, CXCL16:FILIP1L, AGK:USP13, MYO18A:FYN, SIRPA:FLII, C16ORF58:FLII, TRIM11: AKAP8L, MFHAS1:DMPK, JMJD8:AKAP8L, DIAPH1: SYNE1, BCKDHA:HAUS8, TMEM254:PSMC5, ACVR1B:HTRA2, MON1B:SYNE1, DCAKD:PMF1-BGLAP, VWA5A:RASD1, TPD52:TRA2A, ZMIZ1:STX2, NUB1:C2CD5, GSE1:RAI14, AGFG1:STX2, NXT2: TRA2A, ACSS1:NPIPA5, FBXW8:USP13, CMIP:TRIO, AGPAT3:FYN, PSMF1:PTOV1, CREG1:TARS, SLC46A1: CEP131, SIRPA:SERPINTF1, DNAJA2:HDAC2, ERLIN2: RAI14, FAM234A:ZNF428, CHMP1A:LIN37, FAM110A: TCF7, ACVR1B:COPS3, GSE1:DDX11, CREG1: ARFGAP3, BRPF3:USP13, MFHAS1:USP13, LAMP1: MAPK7, ACSS1:PMF1-BGLAP, SUFU:TRIO, ARF3: DAD1, NLRX1:TRA2A, NLRX1:SLC39A13, CMIP: SH3BP5, PPIF:HAUS8, ANKRD13A:SOCS4, F8:SYNE1, ATP6V1A:USP48, ACVR1B:MPRIP, TMEM141:HAUS8, TIRAP:MPRIP, ZDHHC12:HAUS8, SLC46A1:MED9, MFHAS1:NCAPD2, ERBB2:CENPL, JMJD7:PQBP1, PHKG2:AKAP8L, SLC36A1:SLC26A6, ATP6V1A: SPDL1, DCTN5:CEP89, IPPK:STX2, LAMB3:ADM, ARPIN:MPRIP, SLC46A1:FYN, ACVR1B:LTV1, GDE1: ZNF576, DMTN:GFPT2, LCMT2:RDH11, ACVR1B: CCDC66, ACVR1B:NEK3, SEC24B:MAP3K7, ZNF764: AKAP8L, CHMP1A:HAUS8, PIGO:USP13, ARF3: MAPK7, GSE1:CCDC66, ACVR1B:METTL17, C20ORF196:HAUS8, ARF3:CBY1, BRPF3:MPRIP, SLC46A1:PSMC5, CMTR2:MAP3K7, TASP1:CCDC66, BRPF3:PIP5K1A, PIGO:FLII, MYO18A:ACIN1, PSMF1: AKAP8L, FBXW11:LTV1, CXCL16:ADAMTS2, SPRYD3:FLII, DPH6:FRA10AC1, PDXK:HAUS8, ACVR1B:WDR45B, MON1B:SMIM10L1, LAT:PRRX1, WDR24:AKAP8L, EHHADH:CCDC174, ACVR1B:

CEP89, MFHAS1:ODF2, ALDH6A1:GOPC, GSE1:NBPF14, EHHADH:MEX3C, BRPF3:STX2, EHHADH:GTF2H2, PIGO:MPRIP, PRKAG1:STX2, EHHADH:SMIM10L1, SLC36A1:SH3PXD2A, ADCK2:STX2, SORD:PDCD5, ACVR1B:LLGL1, LAMTOR3:ZNF644, PIM1:MICAL2, CREG1:NPIPA1, GSE1:NPIPA1, PRR13:HAUS8, WDR55:RAD1, CMIP:NID2, DIAPH1:TARS, SNAP23:SNX6, GSE1:TSPYL2, C2ORF68:NPIPA1, MFHAS1:TRIO, DPH6:CGRRF1, KIF13B:STX2, PTK2B:TCF7, ATP2A2:STX2, ANKS1A:USP13, JRK:NEK3, LRBA:DDX5, IDH2:HAUS8, CCNF:HAUS8, CMIP:CHN1, STAU2:STX2, ACSS1:LHFP, GSR:STX2, IGF2R:FYN, CXCL16:ACVRL1.

In some embodiments, the first set of dependent variables consists of the ratios: BRAF:RAI14, PRKAG1:STX2, AGPAT3:FYN, CMIP:ROBO4, RAB40C:HAUS8, SNAP23:SNX6.

In some embodiments, the first set of dependent variables comprises at least three ratios, at least four ratios, at least five ratios, or at least six ratios.

In some embodiments, the predictor set of genes includes at least eight of the group of genes consisting of: BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the predictor set of genes includes at least eleven of the group of genes consisting of: BRAF, PRKAG1, STX2, AGPAT3, FYN, CMIP, ROBO4, RAB40C, HAUS8, SNAP23, SNX6, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the predictor set of genes comprises BRAF, PRKAG1, STX2, AGPAT3, FYN, CMIP, ROBO4, RAB40C, HAUS8, SNAP23, SNX6, XAGE1E, SERPINF1, RAI14, SIRPA, MT1X, NEK3, TGFB3, USP13, HLA-DRB4, IGF2, and MICAL1.

In some embodiments, the predictor set of genes consists of XAGE1E, SERPINF1, RAI14, SIRPA, MT1X, NEK3, TGFB3, USP13, HLA-DRB4, IGF2, and MICAL1.

In some embodiments, the expression data is obtained using one or more of the following techniques: whole transcriptome sequencing and mRNA sequencing.

In some embodiments, the system further comprises providing output to a user of whether the additional subject is likely to respond positively to the checkpoint blockade therapy and/or whether the additional subject is not likely to respond positively to the checkpoint blockade therapy.

In one aspect provided herein is a method for determining whether or not a subject is likely to respond to a checkpoint blockade therapy, the method comprising: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

In one aspect provided herein is a system for determining whether or not a subject is likely to respond to a checkpoint blockade therapy, the system comprising: at least one computer hardware processor; and at least one non-transitory computer readable storage medium storing processor-executable instructions that, when executed by the at least one computer hardware processor, causes the at least one computer hardware processor to perform: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

In one aspect provided herein is at least one non-transitory computer readable storage medium storing processor-executable instructions that, when executed at least one computer hardware processor, causes the at least one computer hardware processor to perform a method for determining whether or not a subject is likely to respond to a checkpoint blockade therapy: obtaining expression data for the subject; using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1; and determining, using the determined expression levels and a statistical model trained using expression data indicating expression levels for a plurality of genes for a plurality of subjects, whether or not the subject is likely to respond to the checkpoint blockade therapy, wherein the checkpoint blockade therapy is a PD1 inhibitor and/or a CTLA4 inhibitor.

In some embodiments, the expression data is used to determine expression levels for at least four genes, at least five genes, at least six genes, at least seven genes, at least eight genes, at least nine genes, or at least ten genes.

In some embodiments, the expression data is RNA expression data, DNA expression data, or protein expression data.

In some embodiments, the statistical model comprises a first set of dependent variables, each representing a ratio of a pair of genes, wherein the genes are selected from: BRAF, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the statistical model comprises a first set of dependent variables, each representing a ratio of a pair of genes, wherein the genes are selected from: BRAF, PRKAG1, STX2, AGPAT3, FYN, CMIP, ROBO4, RAB40C, HAUS8, SNAP23, SNX6, XAGE1E, SERPINF1, RAI14, SIRPA, MT1X, NEK3, TGFB3, USP13, HLA-DRB4, IGF2, and MICAL1.

In some embodiments, the statistical model comprises a first set of dependent variables, each representing a ratio of a pair of genes, wherein the genes comprise: BRAF, RAI14, PRKAG1, STX2, AGPAT3, FYN, CMIP, ROBO4, RAB40C, HAUS8, SNAP23, and SNX6.

In some embodiments, the statistical model comprises a first set of dependent variables, each representing a ratio of a pair of genes, wherein the genes consist of: BRAF, RAI14, PRKAG1, STX2, AGPAT3, FYN, CMIP, ROBO4, RAB40C, HAUS8, SNAP23, and SNX6.

In some embodiments, the first set of dependent variables comprises at least two ratios selected from: BRAF:RAI14, ACVR1B:MPRIP, ACVR1B:COPS3, PRKAG1:STX2, NLRX1:ELAC2, MON1B:STX2, ARF3:MPRIP, ARPIN:MPRIP, SPRYD3:FLI1, TIRAP:MPRIP, GSE1:RAI14, POLR3K:HAUS8, RAB40C:HAUS8, PIGO:MPRIP, MFHAS1:USP13, GSE1:NPIPA1, DPH6:STX2, ERLIN2:RAI14, CES2:LHFP, and NAIF1:HAUS8.

In some embodiments, the first set of dependent variables comprises at least two ratios selected from: MON1B:STX2, FAM234A:LIN37, DPH6:STX2, BRAF:RAI14, ADCK2:C14ORF80, POLR3K:HAUS8, URB1:TMEM181, GCLC:NEK3, RAB40C:HAUS8, NLRX1:ELAC2, CMIP:ROBO4, NXT2:FBXO5, EIF3H:NEK3, EHHADH:SNX6, DMTN:RASD1, SLC46A1:RBM8A, ACVR1B:GTF2H2, NPEPPS:HDAC2, CXCL16:BASP1, MFHAS1:DYRK3, ACVR1B:USP13, DPH6:C14ORF166, CES2:LHFP, ACVR1B:DCP1B, NAIF1:HDGFRP2, ABCC1:TRIO, GPR107:STX2, ZDHHC7:USP13, PRKAG1:TSEN2, PC:HAUS8, LRBA:CEP192, POM121C:CNPY4, KAT14:SETD5, SLC35A5:SNX6, ATP6V1A:GTDC1, TXNL4B:AKAP8L, SLC36A1:HAUS8, PSAP:SH3BP5, CMIP:OLFML2B, TATDN3:NEK3, TASP1:DDX5, SDC4:FUT8, TMEM254:COPS3, ARF3:MPRIP, SLC46A1:PMF1-BGLAP, ATP6V1A:FBXO30, MFHAS1:C2CD5, ERAP1:SYNE1, F11R:FYN, RCHY1:RNF146, ATP6V1A:PDCD5, ACVR1B:ELAC2, CLN3:HAUS8, NAIF1:HAUS8, PRKAG1:SOCS4, HNRNPH2:USP13, TPD52:MTRF1L, ACVR1B:C14ORF80, IST1:NPIPA1, DPH6:TCEAL1, CSNK2A1:MRGBP, CXCL16:FILIP1L, AGK:USP13, MYO18A:FYN, SIRPA:FLII, C16ORF58:FLII, TRIM11:AKAP8L, MFHAS1:DMPK, JMJD8:AKAP8L, DIAPH1:SYNE1, BCKDHA:HAUS8, TMEM254:PSMC5, ACVR1B:HTRA2, MON1B:SYNE1, DCAKD:PMF1-BGLAP, VWA5A:RASD1, TPD52:TRA2A, ZMIZ1:STX2, NUB1:C2CD5, GSE1:RAI14, AGFG1:STX2, NXT2:TRA2A, ACSS1:NPIPA5, FBXW8:USP13, CMIP:TRIO, AGPAT3:FYN, PSMF1:PTOV1, CREG1:TARS, SLC46A1:CEP131, SIRPA:SERPINTF1, DNAJA2:HDAC2, ERLIN2:RAI14, FAM234A:ZNF428, CHMP1A:LIN37, FAM110A:TCF7, ACVR1B:COPS3, GSE1:DDX11, CREG1:ARFGAP3, BRPF3:USP13, MFHAS1:USP13, LAMP1:MAPK7, ACSS1:PMF1-BGLAP, SUFU:TRIO, ARF3:DAD1, NLRX1:TRA2A, NLRX1:SLC39A13, CMIP:SH3BP5, PPIF:HAUS8, ANKRD13A:SOCS4, F8:SYNE1, ATP6V1A:USP48, ACVR1B:MPRIP, TMEM141:HAUS8, TIRAP:MPRIP, ZDHHC12:HAUS8, SLC46A1:MED9, MFHAS1:NCAPD2, ERBB2:CENPL, JMJD7:PQBP1, PHKG2:AKAP8L, SLC36A1:SLC26A6, ATP6V1A:SPDL1, DCTN5:CEP89, IPPK:STX2, LAMB3:ADM, ARPIN:MPRIP, SLC46A1:FYN, ACVR1B:LTV1, GDE1:ZNF576, DMTN:GFPT2, LCMT2:RDH11, ACVR1B:CCDC66, ACVR1B:NEK3, SEC24B:MAP3K7, ZNF764:AKAP8L, CHMP1A:HAUS8, PIGO:USP13, ARF3:MAPK7, GSE1:CCDC66, ACVR1B:METTL17, C200RF196:HAUS8, ARF3:CBY1, BRPF3:MPRIP, SLC46A1:PSMC5, CMTR2:MAP3K7, TASP1:CCDC66, BRPF3:PIP5K1A, PIGO:FLII, MYO18A:ACIN1, PSMF1:AKAP8L, FBXW11:LTV1, CXCL16:ADAMTS2, SPRYD3:FLII, DPH6:FRA10AC1, PDXK:HAUS8, ACVR1B:WDR45B, MON1B:SMIM10L1, LAT:PRRX1, WDR24:AKAP8L, EHHADH:CCDC174, ACVR1B:CEP89, MFHAS1:ODF2, ALDH6A1:GOPC, GSE1:NBPF14, EHHADH:MEX3C, BRPF3:STX2, EHHADH:GTF2H2, PIGO:MPRIP, PRKAG1:STX2, EHHADH:SMIM10L1, SLC36A1:SH3PXD2A, ADCK2:STX2, SORD:PDCD5, ACVR1B:LLGL1, LAMTOR3:ZNF644, PIM1:MICAL2, CREG1:NPIPA1, GSE1:NPIPA1, PRR13:HAUS8, WDR55:RAD1, CMIP:NID2, DIAPH1:TARS, SNAP23:SNX6, GSE1:TSPYL2, C2ORF68:NPIPA1, MFHAS1:TRIO, DPH6:CGRRF1, KIF13B:STX2, PTK2B:TCF7, ATP2A2:STX2, ANKS1A:USP13, JRK:NEK3, LRBA:DDX5, IDH2:HAUS8, CCNF:HAUS8, CMIP:CHN1, STAU2:STX2, ACSS1:LHFP, GSR:STX2, IGF2R:FYN, CXCL16:ACVRL1.

In some embodiments, the first set of dependent variables consists of the ratios: BRAF:RAI14, PRKAG1:STX2, AGPAT3:FYN, CMIP:ROBO4, RAB40C:HAUS8, SNAP23:SNX6.

In some embodiments, the first set of dependent variables comprises at least three ratios, at least four ratios, at least five ratios, or at least six ratios.

In some embodiments, the expression data to determine expression levels, in the subject, for at least eight genes from the group consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

In some embodiments, the expression data to determine expression levels, in the subject, for at least eleven genes from the group consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

Some embodiments further comprise administering a PD1 inhibitor, a CTLA4 inhibitor, or a PD1 inhibitor and a CTLA4 inhibitor.

In some embodiments, the statistical model comprises a generalized linear model. IN some embodiments, the statistical model comprises a logistic regression model.

In some embodiments, training the statistical model comprises training a generalized linear model having a plurality of regression variables, each of the plurality of regression variables representing a ratio of a pair of genes for respective pairs of the predictor set of genes.

In some embodiments, training the statistical model comprises training a logistic regression model having a plurality of regression variables, each of the plurality of regression variables representing a ratio of a pair of genes for respective pairs of the predictor set of genes.

In some embodiments, the logistic regression model comprises a respective plurality of weights for the plurality of regression variables, and estimating the parameters of the statistical model comprises: estimating the plurality of weights using the expression data for the plurality of subjects and information indicating which of the plurality of subjects responded to the checkpoint blockade therapy and/or which of the plurality of subjects did not respond to the checkpoint blockade therapy.

In some embodiments, training the statistical model comprises iteratively adding regression variables for respective genes to the statistical model, at least in part by: identifying a candidate gene in the subset of genes; augmenting a current statistical model with a regression variable for the candidate gene to obtain an augmented statistical model; evaluating performance of the augmented statistical model; and determining to add the regression variable for the candidate gene to the current statistical model based on results of evaluating the performance.

In some embodiments, the subject has melanoma.

Some embodiments further include providing, to a user, an indication of whether or not the subject is likely to respond to the checkpoint blockade therapy.

EQUIVALENTS AND SCOPE

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the technology described herein need not reside on a single computer or processor, but may be distributed in a modular fashion among different computers or processors to implement various aspects of the technology described herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the described methods and systems encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the systems and methods described herein (or aspects thereof) are referred to as comprising particular elements and/or features, certain embodiments of the systems and methods or aspects of the same consist, or consist essentially of, such elements and/or features. For purposes of simplicity, those embodiments have not been specifically set forth in haec verba herein.

It is also noted that the terms "including," "comprising," "having," "containing", "involving", are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the described systems and methods, to the tenth of the unit of the lower limit of the range, unless the context clearly dictates otherwise.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Additionally, as used herein the terms "patient" and "subject" may be used interchangeably. Such terms may include, but are not limited to, human subjects or patients. Such terms may also include non-human primates or other animals.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that fall within the prior art may be explicitly excluded from any one or more of the claims. Because such embodiments are deemed to be known to one of ordinary skill in the art, they may be excluded even if the exclusion is not set forth explicitly herein. Any particular embodiment of the systems and methods described herein can be excluded from any claim, for any reason, whether or not related to the existence of prior art.

Those skilled in the art will recognize or be able to ascertain using no more than routine experimentation many equivalents to the specific embodiments described herein.

The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. A method for administering a checkpoint blockade therapy to a subject, the method comprising:
    obtaining expression data for the subject;
    using the expression data to determine expression levels, in the subject, for at least three genes selected from the set of predictor genes consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1;
    determining, using the determined expression levels and a logistic regression model, that the subject is likely to respond to the checkpoint blockade therapy, wherein the checkpoint blockade therapy is a PD1 inhibitor and/or a CTLA4 inhibitor, wherein the logistic regression model comprises dependent variables each of which represents a respective ratio of a pair of genes, wherein the genes are selected from the set of predictor genes; and
    administering the PD1 inhibitor and/or the CTLA4 inhibitor to the subject based on output of the logistic regression model.

2. The method of claim 1, further comprising using the expression data to determine expression levels for at least six genes selected from the set of predictor genes.

3. The method of claim 1, wherein the expression data is RNA expression data, DNA expression data, or protein expression data.

4. The method of claim 1, wherein the dependent variables comprises at least two ratios selected from: MON1B: STX2, FAM234A:LIN37, DPH6:STX2, BRAF:RAI14, ADCK2:C14ORF80, POLR3K:HAUS8, URB1:TMEM181, GCLC:NEK3, RAB40C:HAUS8, NLRX1:ELAC2, CMIP: ROBO4, NXT2:FBXO5, EIF3H:NEK3, EHHADH:SNX6, DMTN:RASD1, SLC46A1:RBM8A, ACVR1B:GTF2H2, NPEPPS:HDAC2, CXCL16:BASP1, MFHAS1:DYRK3, ACVR1B:USP13, DPH6:C14ORF166, CES2:LHFP, ACVR1B:DCP1B, NAIF1:HDGFRP2, ABCC1:TRIO, GPR107:STX2, ZDHHC7:USP13, PRKAG1:TSEN2, PC:HAUS8, LRBA:CEP192, POM121C:CNPY4, KAT14: SETD5, SLC35A5:SNX6, ATP6V1A:GTDC1, TXNL4B: AKAP8L, SLC36A1:HAUS8, PSAP:SH3BP5, CMIP: OLFML2B, TATDN3:NEK3, TASP1:DDX5, SDC4:FUT8, TMEM254:COPS3, ARF3:MPRIP, SLC46A1:PMF1-BGLAP, ATP6V1A:FBXO30, MFHAS1:C2CD5, ERAP1: SYNE1, F11R:FYN, RCHY1:RNF146, ATP6V1A:PDCD5, ACVR1B:ELAC2, CLN3:HAUS8, NAIF1:HAUS8, PRKAG1:SOCS4, HNRNPH2:USP13, TPD52:MTRF1L, ACVR1B:C14ORF80, IST1:NPIPA1, DPH6:TCEAL1, CSNK2A1:MRGBP, CXCL16:FILIP1L, AGK:USP13, MYO18A:FYN, SIRPA:FLI1, C16ORF58:FLI1, TRIM11: AKAP8L, MFHAS1:DMPK, JMJD8:AKAP8L, DIAPH1:

SYNE1, BCKDHA:HAUS8, TMEM254:PSMC5, ACVR1B:HTRA2, MON1B:SYNE1, DCAKD:PMF1-BGLAP, VWA5A:RASD1, TPD52:TRA2A, ZMIZ1:STX2, NUB1:C2CD5, GSE1:RAI14, AGFG1:STX2, NXT2:TRA2A, ACSS1:NPIPA5, FBXW8:USP13, CMIP:TRIO, AGPAT3:FYN, PSMF1:PTOV1, CREG1:TARS, SLC46A1:CEP131, SIRPA:SERPINF1, DNAJA2:HDAC2, ERLIN2:RAI14, FAM234A:ZNF428, CHMP1A:LIN37, FAM110A:TCF7, ACVR1B:COPS3, GSE1:DDX11, CREG1:ARFGAP3, BRPF3:USP13, MFHAS1:USP13, LAMP1:MAPK7, ACSS1:PMF1-BGLAP, SUFU:TRIO, ARF3:DAD1, NLRX1:TRA2A, NLRX1:SLC39A13, CMIP:SH3BP5, PPIF:HAUS8, ANKRD13A:SOCS4, F8:SYNE1, ATP6V1A:USP48, ACVR1B:MPRIP, TMEM141:HAUS8, TIRAP:MPRIP, ZDHHC12:HAUS8, SLC46A1:MED9, MFHAS1:NCAPD2, ERBB2:CENPL, JMJD7:PQBP1, PHKG2:AKAP8L, SLC36A1:SLC26A6, ATP6V1A:SPDL1, DCTN5:CEP89, IPPK:STX2, LAMB3:ADM, ARPIN:MPRIP, SLC46A1:FYN, ACVR1B:LTV1, GDE1:ZNF576, DMTN:GFPT2, LCMT2:RDH11, ACVR1B:CCDC66, ACVR1B:NEK3, SEC24B:MAP3K7, ZNF764:AKAP8L, CHMP1A:HAUS8, PIGO:USP13, ARF3:MAPK7, GSE1:CCDC66, ACVR1B:METTL17, C20ORF196:HAUS8, ARF3:CBY1, BRPF3:MPRIP, SLC46A1:PSMC5, CMTR2:MAP3K7, TASP1:CCDC66, BRPF3:PIP5K1A, PIGO:FLII, MYO18A:ACIN1, PSMF1:AKAP8L, FBXW1:LTV1, CXCL16:ADAMTS2, SPRYD3:FLII, DPH6:FRA10AC1, PDXK:HAUS8, ACVR1B:WDR45B, MON1B:SMIM10L1, LAT:PRRX1, WDR24:AKAP8L, EHHADH:CCDC174, ACVR1B:CEP89, MFHAS1:ODF2, ALDH6A1:GOPC, GSE1:NBPF14, EHHADH:MEX3C, BRPF3:STX2, EHHADH:GTF2H2, PIGO:MPRIP, PRKAG1:STX2, EHHADH:SMIM10L1, SLC36A1:SH3PXD2A, ADCK2:STX2, SORD:PDCD5, ACVR1B:LLGL1, LAMTOR3:ZNF644, PIM1:MICAL2, CREG1:NPIPA1, GSE1:NPIPA1, PRR13:HAUS8, WDR55:RAD1, CMIP:NID2, DIAPH1:TARS, SNAP23:SNX6, GSE1:TSPYL2, C2ORF68:NPIPA1, MFHAS1:TRIO, DPH6:CGRRF1, KIF13B:STX2, PTK2B:TCF7, ATP2A2:STX2, ANKS1A:USP13, JRK:NEK3, LRBA:DDX5, IDH2:HAUS8, CCNF:HAUS8, CMIP:CHN1, STAU2:STX2, ACSS1:LHFP, GSR:STX2, IGF2R:FYN, CXCL16:ACVRL1.

5. The method of claim 1, further comprising using the expression data to determine expression levels, in the subject, for at least eight genes from the group consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

6. The method of claim 1, further comprising using the expression data to determine expression levels, in the subject, for at least eleven genes from the group consisting of BRAF, ACVR1B, MPRIP, PRKAG1, STX2, AGPAT3, FYN, CMIP, ROBO4, RAB40C, HAUS8, SNAP23, SNX6, ACVR1B, MPRIP, COPS3, NLRX1, ELAC2, MON1B, ARF3, ARPIN, SPRYD3, FLI1, TIRAP, GSE1, POLR3K, PIGO, MFHAS1, NPIPA1, DPH6, ERLIN2, CES2, LHFP, NAIF1, ALCAM, SYNE1, SPINT1, SMTN, SLCA46A1, SAP25, WISP2, TSTD1, NLRX1, NPIPA1, HIST1H2AC, FUT8, FABP4, ERBB2, TUBA1A, XAGE1E, SERPINF1, RAI14, SIRPA, MT1X, NEK3, TGFB3, USP13, HLA-DRB4, IGF2, and MICAL1.

7. The method of claim 1, wherein the logistic regression model comprises respective weights for the dependent variables, the method further comprising training the logistic regression model at least in part by:
estimating the weights using the expression data for a plurality of subjects and information indicating which of the plurality of subjects responded to the checkpoint blockade therapy and/or which of the plurality of subjects did not respond to the checkpoint blockade therapy.

8. The method of claim 7, wherein training the logistic regression model comprises iteratively adding dependent variables for respective genes to the logistic regression model, at least in part by:
identifying a candidate gene;
augmenting a current logistic regression model with a dependent variable for the candidate gene to obtain an augmented logistic regression model;
evaluating performance of the augmented logistic regression model; and
determining to add the dependent variable for the candidate gene to the current logistic regression model based on results of evaluating the performance.

9. The method of claim 1, wherein the subject has melanoma.

* * * * *

UNITED STATES PATENT AND TRADEMARK OFFICE
CERTIFICATE OF CORRECTION

PATENT NO. : 10,720,230 B2  
APPLICATION NO. : 16/006129  
DATED : July 21, 2020  
INVENTOR(S) : Feliks Frenkel et al.

Page 1 of 1

It is certified that error appears in the above-identified patent and that said Letters Patent is hereby corrected as shown below:

In the Claims

In Claim 4, Column 67, Line 24:  
C20ORF196:HAUS8, ARF3:CBY1, BRPF3:MPRIP,  
Should read:  
C20orf196:HAUS8, ARF3:CBY1, BRPF3:MPRIP, In Claim 4, Column 67, Line 27:  
AKAP8L, FBXW1:LTV1, CXCL16:ADAMTS2, SPRYD3:  
Should read:  
AKAP8L, FBXW11:LTV1, CXCL16:ADAMTS2, SPRYD3:

Signed and Sealed this  
Twenty-second Day of September, 2020

Andrei Iancu  
*Director of the United States Patent and Trademark Office*